(12) United States Patent
Gara et al.

(10) Patent No.: US 7,476,209 B2
(45) Date of Patent: Jan. 13, 2009

(54) METHOD AND APPARATUS FOR COLLECTING A BLOOD COMPONENT AND PERFORMING A PHOTOPHERESIS TREATMENT

(75) Inventors: Stephen Gara, Souderton, PA (US); Cynthia Star, Dresher, PA (US); Dennis Briggs, West Chester, PA (US); Michael Hutchinson, King of Prussia, PA (US); Tom Watters, Malvern, PA (US)

(73) Assignee: Therakos, Inc., Exton, PA (US)

( * ) Notice: Subject to any disclaimer, the term of this patent is extended or adjusted under 35 U.S.C. 154(b) by 384 days.

(21) Appl. No.: 11/304,092

(22) Filed: Dec. 15, 2005

(65) Prior Publication Data

US 2006/0155236 A1 Jul. 13, 2006

Related U.S. Application Data

(60) Provisional application No. 60/637,985, filed on Dec. 21, 2004.

(51) Int. Cl.
*A61M 37/00* (2006.01)
*B60G 17/052* (2006.01)
*F04B 43/08* (2006.01)
*F16K 3/24* (2006.01)
*C02F 1/44* (2006.01)

(52) U.S. Cl. .................. 604/6.01; 604/6.1; 210/90; 210/252; 417/477.9; 417/477.13; 137/627.5; 137/628

(58) Field of Classification Search ............... 604/4.01, 604/5.01, 6.01, 6.1, 6.11; 210/90; 422/44; 137/628; 417/477.2, 477.9, 477.13
See application file for complete search history.

(56) References Cited

U.S. PATENT DOCUMENTS

| | | | |
|---|---|---|---|
| 2,983,639 | A | 5/1961 | Jageman |
| 3,103,489 | A | 9/1963 | Pickles |
| 3,145,713 | A | 8/1964 | Latham, Jr. |
| 3,628,445 | A | 12/1971 | Webster |
| 3,678,964 | A | 7/1972 | Andrews |
| 3,861,972 | A | 1/1975 | Glover et al. |
| 4,056,224 | A | 11/1977 | Lolachi |
| 4,059,108 | A | 11/1977 | Latham, Jr. |
| 4,086,924 | A | 5/1978 | Latham, Jr. |
| 4,108,353 | A | 8/1978 | Brown |

(Continued)

FOREIGN PATENT DOCUMENTS

DE 3817664 A1 11/1989

(Continued)

OTHER PUBLICATIONS

Partial European Search Report, dated Mar. 31, 2006, for European Appln. No. EP 05257861.

*Primary Examiner*—Leslie R Deak
(74) *Attorney, Agent, or Firm*—Todd F. Volyn

(57) ABSTRACT

Methods and apparatus for collecting and treating blood component. An apparatus and methods for improvement of an extracorporeal photopheresis treatment is described. A cassette having flexible tubes inside its housing and on the bottom surface outside the cassette housing for ease of manufacturing is operated with a centrifuge bowl having an inlet and two outlets, pressure domes for measuring pressures in tubes, an improved irradiation plate, and a dual chamber bag in an extracorporeal photopheresis treatment.

11 Claims, 68 Drawing Sheets

U.S. PATENT DOCUMENTS

| | | |
|---|---|---|
| 4,109,852 A | 8/1978 | Brown et al. |
| 4,109,854 A | 8/1978 | Brown |
| 4,109,855 A | 8/1978 | Brown et al. |
| 4,113,173 A | 9/1978 | Lolachi |
| 4,114,802 A | 9/1978 | Brown |
| 4,120,448 A | 10/1978 | Cullis |
| 4,120,449 A | 10/1978 | Brown et al. |
| 4,164,318 A | 8/1979 | Boggs |
| 4,194,684 A | 3/1980 | Boggs |
| 4,204,537 A | 5/1980 | Latham, Jr. |
| 4,221,322 A | 9/1980 | Drago et al. |
| 4,230,263 A | 10/1980 | Westberg |
| 4,245,383 A | 1/1981 | Boggs |
| 4,261,507 A | 4/1981 | Baumler |
| 4,285,464 A | 8/1981 | Latham, Jr. |
| 4,300,717 A | 11/1981 | Latham, Jr. |
| 4,303,193 A | 12/1981 | Latham, Jr. |
| 4,344,560 A | 8/1982 | Iriguchi et al. |
| 4,372,484 A | 2/1983 | Larsson et al. |
| 4,389,206 A | 6/1983 | Bacehowski et al. |
| 4,407,295 A | 10/1983 | Steuer et al. |
| 4,417,884 A | 11/1983 | Schoendorfer et al. |
| 4,421,503 A | 12/1983 | Latham, Jr. et al. |
| 4,425,112 A | 1/1984 | Ito |
| 4,439,178 A | 3/1984 | Mulzet |
| 4,440,195 A | 4/1984 | van Dongeren |
| 4,459,169 A | 7/1984 | Bacehowski et al. |
| 4,517,404 A | 5/1985 | Hughes et al. |
| 4,540,397 A | 9/1985 | Lolachi et al. |
| 4,573,960 A | 3/1986 | Goss |
| 4,573,962 A | 3/1986 | Troutner |
| 4,578,056 A | 3/1986 | King et al. |
| 4,636,346 A | 1/1987 | Gold et al. |
| 4,692,136 A | 9/1987 | Feldman et al. |
| 4,708,712 A | 11/1987 | Mulzet |
| 4,710,161 A | 12/1987 | Takabayashi et al. |
| 4,734,089 A | 3/1988 | Cullis |
| 4,737,140 A | 4/1988 | Lee et al. |
| 4,767,396 A | 8/1988 | Powers |
| 4,775,794 A | 10/1988 | Behmann |
| 4,776,964 A | 10/1988 | Schoendorfer et al. |
| 4,778,444 A | 10/1988 | Westberg et al. |
| 4,806,252 A | 2/1989 | Brown et al. |
| 4,854,933 A | 8/1989 | Mull |
| 4,857,190 A | 8/1989 | Wada et al. |
| 4,859,333 A | 8/1989 | Panzani |
| 4,865,081 A | 9/1989 | Neumann et al. |
| 4,866,282 A | 9/1989 | Miripol et al. |
| 4,876,014 A | 10/1989 | Malson |
| 4,879,031 A | 11/1989 | Panzani |
| 4,889,524 A | 12/1989 | Fell et al. |
| 4,898,571 A | 2/1990 | Epper et al. |
| 4,911,833 A | 3/1990 | Schoendorfer et al. |
| 4,943,273 A | 7/1990 | Pages |
| 4,950,401 A | 8/1990 | Unger et al. |
| 4,963,131 A | 10/1990 | Wortrich et al. |
| D312,128 S | 11/1990 | Headley |
| 4,983,158 A | 1/1991 | Headley |
| 4,986,442 A | 1/1991 | Hinterreiter |
| 4,997,577 A | 3/1991 | Stewart |
| 5,039,401 A | 8/1991 | Columbus et al. |
| 5,053,127 A | 10/1991 | Schoendorfer et al. |
| 5,061,381 A | 10/1991 | Burd |
| 5,076,911 A | 12/1991 | Brown et al. |
| 5,078,671 A | 1/1992 | Dennehey et al. |
| 5,097,870 A | 3/1992 | Williams |
| 5,100,372 A | 3/1992 | Headley |
| 5,104,526 A | 4/1992 | Brown et al. |
| 5,147,290 A | 9/1992 | Jonsson |
| 5,160,310 A | 11/1992 | Yhland |
| 5,186,844 A | 2/1993 | Burd et al. |
| 5,217,426 A | 6/1993 | Bacehowski et al. |
| 5,217,427 A | 6/1993 | Cullis |
| 5,224,921 A | 7/1993 | Dennehey et al. |
| 5,240,614 A | 8/1993 | Ofsthun et al. |
| 5,254,248 A | 10/1993 | Nakamura |
| 5,273,517 A | 12/1993 | Barone et al. |
| 5,281,342 A | 1/1994 | Biesel et al. |
| 5,298,171 A | 3/1994 | Biesel |
| 5,305,799 A | 4/1994 | Dal Palu |
| 5,316,667 A | 5/1994 | Brown |
| 5,322,620 A | 6/1994 | Brown et al. |
| 5,332,500 A | 7/1994 | Seureau et al. |
| 5,360,542 A | 11/1994 | Williamson, IV et al. |
| 5,362,291 A | 11/1994 | Williamson, IV |
| 5,370,802 A | 12/1994 | Brown |
| 5,372,136 A | 12/1994 | Steuer et al. |
| 5,405,308 A | 4/1995 | Headley et al. |
| 5,427,509 A | 6/1995 | Chapman et al. |
| 5,427,695 A | 6/1995 | Brown |
| 5,437,598 A | 8/1995 | Antwiler |
| 5,443,451 A | 8/1995 | Chapman et al. |
| 5,445,506 A | 8/1995 | Afflerbaugh et al. |
| 5,445,593 A | 8/1995 | Biesel et al. |
| 5,460,493 A | 10/1995 | Deniega et al. |
| 5,462,416 A | 10/1995 | Dennehey et al. |
| 5,480,294 A | 1/1996 | Di Perna et al. |
| 5,482,440 A | 1/1996 | Dennehey et al. |
| 5,494,578 A | 2/1996 | Brown et al. |
| 5,494,592 A | 2/1996 | Lathan, Jr. et al. |
| 5,501,840 A | 3/1996 | Mantovani et al. |
| 5,505,685 A | 4/1996 | Antwiler |
| 5,514,069 A | 5/1996 | Brown et al. |
| 5,514,070 A | 5/1996 | Pages |
| 5,525,218 A | 6/1996 | Williamson, IV et al. |
| 5,527,467 A | 6/1996 | Ofsthun et al. |
| 5,527,472 A | 6/1996 | Bellotti et al. |
| 5,529,691 A | 6/1996 | Brown |
| 5,538,405 A | 7/1996 | Patno et al. |
| 5,549,834 A | 8/1996 | Brown |
| 5,551,942 A | 9/1996 | Brown et al. |
| 5,573,678 A | 11/1996 | Brown et al. |
| 5,591,113 A | 1/1997 | Darnell et al. |
| 5,591,643 A | 1/1997 | Schembri |
| 5,607,579 A | 3/1997 | Latham, Jr. et al. |
| 5,628,915 A | 5/1997 | Brown et al. |
| 5,632,893 A | 5/1997 | Brown et al. |
| 5,634,893 A | 6/1997 | Rishton |
| 5,637,082 A | 6/1997 | Pages et al. |
| 5,639,382 A | 6/1997 | Brown |
| 5,641,414 A | 6/1997 | Brown |
| 5,641,622 A | 6/1997 | Lake et al. |
| 5,643,193 A | 7/1997 | Papillon et al. |
| 5,651,766 A | 7/1997 | Kingsley et al. |
| 5,656,163 A | 8/1997 | Brown |
| 5,676,841 A | 10/1997 | Brown |
| 5,681,273 A | 10/1997 | Brown |
| 5,690,602 A | 11/1997 | Brown et al. |
| 5,690,835 A | 11/1997 | Brown |
| 5,693,232 A | 12/1997 | Brown et al. |
| 5,702,357 A | 12/1997 | Bainbridge et al. |
| 5,704,887 A | 1/1998 | Slowik et al. |
| 5,728,060 A | 3/1998 | Kingsley |
| 5,730,883 A | 3/1998 | Brown |
| 5,738,644 A | 4/1998 | Holmes et al. |
| 5,738,784 A | 4/1998 | Holm et al. |
| 5,750,039 A | 5/1998 | Brown |
| 5,759,147 A | 6/1998 | Bacehowski et al. |
| 5,759,413 A | 6/1998 | Brown |
| 5,769,811 A | 6/1998 | Stacey et al. |
| 5,779,660 A | 7/1998 | Kingsley et al. |
| 5,785,869 A | 7/1998 | Martinson et al. |
| 5,792,372 A | 8/1998 | Brown et al. |
| 5,804,079 A | 9/1998 | Brown |

| | | | | | | |
|---|---|---|---|---|---|---|
| 5,807,492 | A | 9/1998 | Brown et al. | 6,579,219 B2 | 6/2003 | Dolecek et al. |
| 5,833,866 | A | 11/1998 | Brown | 6,582,349 B1 | 6/2003 | Cantu et al. |
| 5,849,203 | A | 12/1998 | Brown et al. | 6,582,350 B2 | 6/2003 | Dolecek |
| 5,855,773 | A | 1/1999 | Lasota | 6,589,153 B2 | 7/2003 | Dolecek et al. |
| 5,868,695 | A | 2/1999 | Wolf, Jr. et al. | 6,589,155 B2 | 7/2003 | Dolecek |
| 5,870,805 | A | 2/1999 | Kandler et al. | 6,596,179 B2 | 7/2003 | Giesler et al. |
| 5,906,598 | A | 5/1999 | Giesler et al. | 6,596,180 B2 | 7/2003 | Baugh et al. |
| 5,916,743 | A | 6/1999 | Lake et al. | 6,596,181 B2 | 7/2003 | Dolecek et al. |
| 5,919,125 | A | 7/1999 | Berch | 6,605,223 B2 | 8/2003 | Jorgensen et al. |
| 5,921,909 | A | 7/1999 | Gustafsson | 6,607,473 B2 | 8/2003 | Collier |
| 5,935,051 | A | 8/1999 | Bell | 6,610,002 B2 | 8/2003 | Dolecek |
| 5,948,271 | A | 9/1999 | Wardwell et al. | 6,612,975 B2 | 9/2003 | Malcom et al. |
| 5,951,509 | A | 9/1999 | Morris | 6,616,589 B1 | 9/2003 | Maehans |
| 5,958,250 | A | 9/1999 | Brown et al. | 6,709,377 B1 | 3/2004 | Rochat |
| 5,961,842 | A | 10/1999 | Min et al. | 2001/0000185 A1 | 4/2001 | Keller et al. |
| 5,976,388 | A | 11/1999 | Carson | 2001/0004444 A1 | 6/2001 | Haser et al. |
| 5,980,757 | A | 11/1999 | Brown et al. | 2001/0024623 A1 | 9/2001 | Grimm et al. |
| 5,980,760 | A | 11/1999 | Min et al. | 2002/0032112 A1 | 3/2002 | Pages |
| 5,989,177 | A | 11/1999 | West et al. | 2002/0068674 A1 | 6/2002 | Hlavinka et al. |
| 5,993,370 | A | 11/1999 | Brown et al. | 2002/0068675 A1 | 6/2002 | Felt et al. |
| 5,996,634 | A | 12/1999 | Dennehey et al. | 2002/0091057 A1 | 7/2002 | Westberg et al. |
| 6,007,509 | A | 12/1999 | Kingsley et al. | 2002/0099319 A1 | 7/2002 | Saito et al. |
| 6,007,725 | A | 12/1999 | Brown | 2002/0142909 A1 | 10/2002 | Sakota |
| 6,027,655 | A | 2/2000 | Holm | 2002/0147094 A1 | 10/2002 | Dolecek |
| 6,027,657 | A | 2/2000 | Min et al. | 2003/0085185 A1 | 5/2003 | Kouba |
| 6,056,522 | A | 5/2000 | Johnson | 2003/0094425 A1 | 5/2003 | Brandt et al. |
| 6,059,979 | A | 5/2000 | Brown | 2003/0102272 A1 | 6/2003 | Brown |
| 6,071,421 | A | 6/2000 | Brown | 2003/0106858 A1 | 6/2003 | Elsom Sharpe |
| 6,071,423 | A | 6/2000 | Brown et al. | 2003/0114289 A1 | 6/2003 | Merino et al. |
| 6,080,322 | A | 6/2000 | Deniega et al. | 2003/0116506 A1 | 6/2003 | Lane |
| 6,102,883 | A | 8/2000 | Kingsley et al. | 2003/0116512 A1 | 6/2003 | Delbert Antwiler et al. |
| 6,123,655 | A | 9/2000 | Fell | 2003/0136739 A1 | 7/2003 | Kirkland et al. |
| 6,129,656 | A | 10/2000 | Blakeslee et al. | 2003/0146170 A1 | 8/2003 | Corbin, III et al. |
| 6,168,561 | B1 | 1/2001 | Cantu et al. | 2003/0155312 A1 | 8/2003 | Ivansons et al. |
| 6,179,801 | B1 | 1/2001 | Holmes et al. | 2003/0173274 A1 | 9/2003 | Corbin, III et al. |
| 6,183,407 | B1 | 2/2001 | Hallgren et al. | 2004/0124157 A1 * | 7/2004 | Briggs et al. ................ 210/787 |
| 6,183,651 | B1 | 2/2001 | Brown et al. | 2004/0127841 A1 | 7/2004 | Briggs |
| 6,186,752 | B1 | 2/2001 | Deniega et al. | | | |
| 6,196,987 | B1 | 3/2001 | Holmes et al. | FOREIGN PATENT DOCUMENTS | | |
| 6,197,202 | B1 | 3/2001 | Brown | DE | 4220232 A1 | 9/1994 |
| 6,200,287 | B1 | 3/2001 | Keller et al. | EP | 112990 A2 | 3/1984 |
| 6,207,063 | B1 | 3/2001 | Brown | EP | 268025 B1 | 5/1988 |
| 6,219,584 | B1 | 4/2001 | Lee | EP | 0297216 | 1/1989 |
| 6,228,017 | B1 | 5/2001 | Brown | EP | 608519 A2 | 8/1994 |
| 6,231,537 | B1 | 5/2001 | Holmes et al. | EP | 749771 A2 | 12/1996 |
| 6,248,053 | B1 | 6/2001 | Ehnstrom et al. | EP | 755708 A2 | 1/1997 |
| 6,251,056 | B1 | 6/2001 | Berger et al. | EP | 779077 A1 | 6/1997 |
| 6,261,065 | B1 | 7/2001 | Nayak et al. | EP | 799645 A1 | 10/1997 |
| 6,261,217 | B1 | 7/2001 | Unger et al. | EP | 1043071 A1 | 10/2000 |
| 6,273,849 | B1 | 8/2001 | Scherer | EP | 1138392 A2 | 10/2001 |
| 6,296,450 | B1 | 10/2001 | Westberg et al. | EP | 1241249 A1 | 9/2002 |
| 6,312,593 | B1 | 11/2001 | Petrie | EP | 1252918 A2 | 10/2002 |
| 6,312,607 | B1 | 11/2001 | Brown et al. | FR | 2305238 A1 | 9/1978 |
| 6,315,707 | B1 | 11/2001 | Smith et al. | JP | 09192215 | 7/1997 |
| 6,322,488 | B1 | 11/2001 | Westberg et al. | JP | 2001/070832 | 9/1999 |
| 6,334,842 | B1 | 1/2002 | Hlavinka et al. | WO | WO 93/12887 A1 | 7/1993 |
| 6,346,069 | B1 | 2/2002 | Collier | WO | WO 94/08687 A1 | 4/1994 |
| 6,348,031 | B1 | 2/2002 | Unger et al. | WO | WO 94/08688 A1 | 4/1994 |
| 6,348,156 | B1 | 2/2002 | Vishnoi et al. | WO | WO 94/15658 | 7/1994 |
| 6,352,499 | B1 | 3/2002 | Geigle | WO | WO 94/29722 A1 | 12/1994 |
| 6,379,322 | B1 | 4/2002 | Kingsley | WO | WO 96/25234 A1 | 8/1996 |
| 6,387,263 | B1 | 5/2002 | Bhaskar et al. | WO | WO 98/28938 A1 | 11/1998 |
| 6,464,624 | B2 | 10/2002 | Pages | WO | WO 99/02269 A1 | 1/1999 |
| 6,475,132 | B2 | 11/2002 | Zettier | WO | WO 99/23471 A1 | 5/1999 |
| 6,491,656 | B1 | 12/2002 | Morris | WO | WO 01/17651 A1 | 3/2001 |
| 6,511,411 | B1 | 1/2003 | Brown | WO | WO 01/17653 A1 | 3/2001 |
| 6,514,189 | B1 | 2/2003 | Hlavinka et al. | WO | WO 01/24848 A1 | 4/2001 |
| 6,524,231 | B1 | 2/2003 | Westberg et al. | WO | WO 02/40176 A1 | 5/2002 |
| 6,544,162 | B1 | 4/2003 | Van Wie et al. | WO | WO 03/000026 A2 | 1/2003 |
| 6,544,416 | B2 | 4/2003 | Helwig | WO | WO 03/013686 A1 | 2/2003 |
| 6,554,788 | B1 | 4/2003 | Hunley et al. | | | |
| 6,558,307 | B2 | 5/2003 | Headley | * cited by examiner | | |

IRDA Protocol Interface

FIG. 44
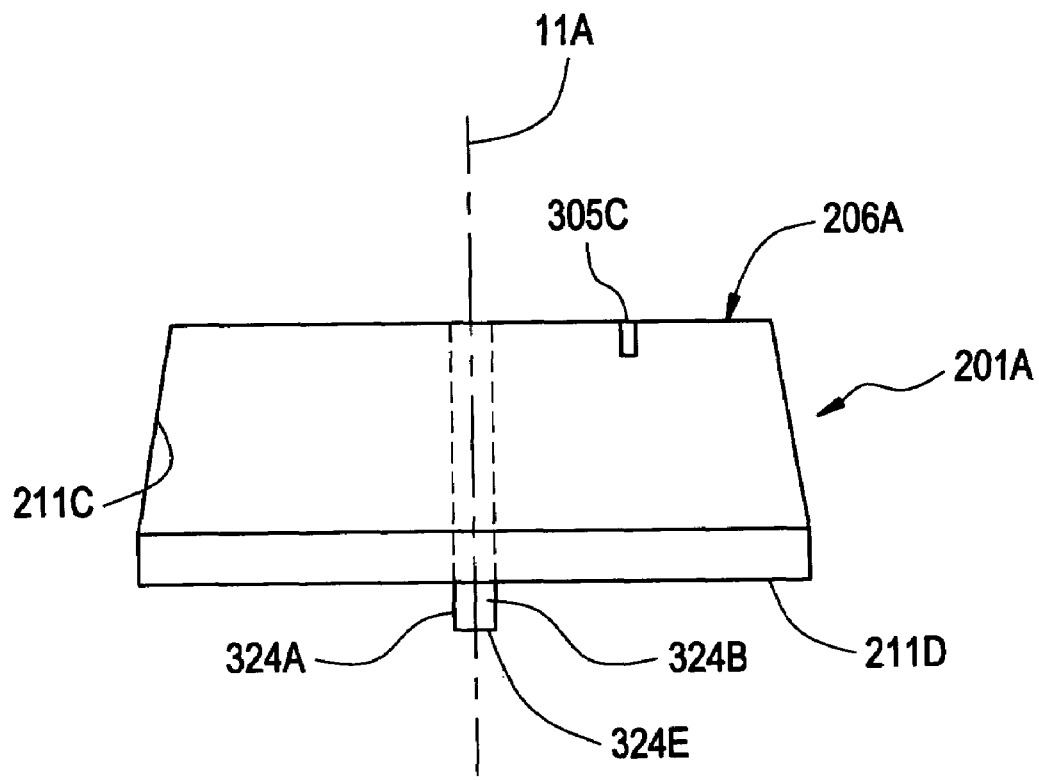
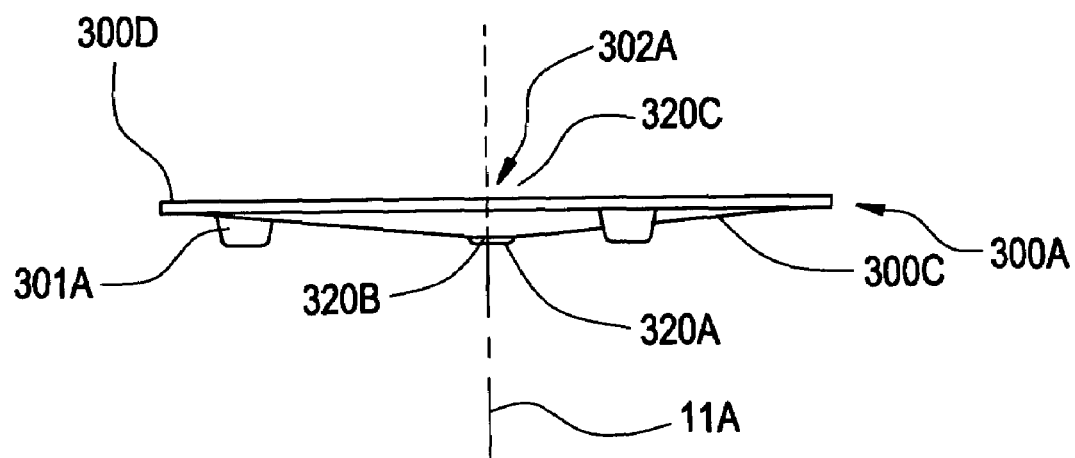

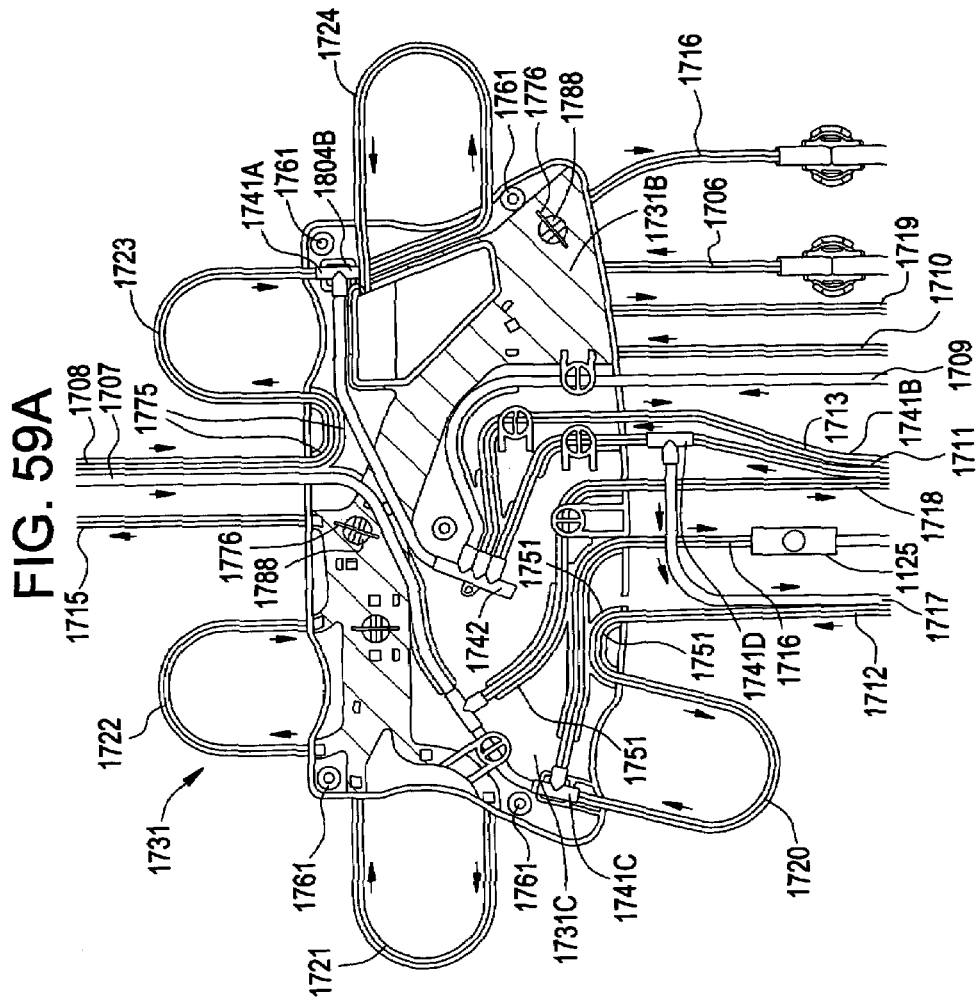

METHOD AND APPARATUS FOR COLLECTING A BLOOD COMPONENT AND PERFORMING A PHOTOPHERESIS TREATMENT

TECHNICAL FIELD OF THE INVENTION

This application claims the benefit of U.S. Provisional application 60/637,985 filed Dec. 21, 2004. The present invention relates generally to a disposable photopheresis kit and methods for separating whole blood into blood components and collecting a desired blood component, and specifically to methods of treating diseases with a photopheresis treatment.

BACKGROUND OF THE INVENTION

Several treatments for disease require the removal of blood from a patient, processing the one or more components of the blood, and return of the processed components for a therapeutic effect. Those extracorporeal treatments require systems for safely removing blood from the patient, separating it into components, and returning the blood or blood components to the patient. With the advance of medical sciences, it has become possible to treat a patient's blood in closed-loop processes, returning the patient's own treated blood back to him in one medical treatment. An example of such processes include external treatment methods for diseases in which there is a pathological increase of lymphocytes, such as cutaneous T-cell lymphoma or other diseases affecting white blood cells. In such methods, the patient's blood is irradiated with ultraviolet light in the presence of a chemical or an antibody. Ultraviolet light affects the bonding between the lymphocytes and the chemical or antibody that inhibits the metabolic processes of the lymphocytes.

Photopheresis systems and methods have been proposed and used which involve separation of buffy coat from the blood, addition of a photoactivatable drug, and UV irradiation of the buffy coat before re-infusion to the patient. Extracorporeal photopheresis may be utilized to treat numerous diseases including Graft-versus-Host disease, Rheumatoid Arthritis, Progressive Systematic Sclerosis, Juvenile Onset Diabetes, Inflammatory Bowel Disease and other diseases that are thought to be T-cell or white blood cell mediated, including cancer. Apheresis systems and methods have also been proposed and used which involve separation of blood into various components.

During one of these medical treatments, a centrifuge bowl, such as, for example, a Latham bowl, as shown in U.S. Pat. No. 4,303,193, expressly incorporated by reference in its entirety herein, is operated to separate whole blood into red blood cells ("RBCs"), plasma, and buffy coat. The Latham bowl is a blood component separator that has been used for some time in the medical apheresis market as well as in innovative medical therapies such as extracorporeal photopheresis (ECP). PCT Applications WO 97/36581 and WO 97/36634, and U.S. Pat. Nos. 4,321,919; 4,398,906; 4,428,744; and 4,464,166 provide descriptions of extracorporeal photopheresis, and are hereby expressly incorporated by reference in their entirety.

Latham bowl efficiency is often measured by the white blood cell ("WBC") "yield," which is typically about 50%. Yield is defined as the percentage of cells collected versus the number processed. When compared to other types of whole blood separators, this high yield enables the Latham bowl separator to collect much larger volumes of WBCs while processing much less whole blood from the donor patient. However, a major drawback to the Latham bowl separator is that the separation process must be repeatedly stopped to remove the packed RBCs and plasma once they fill the inside of the bowl, creating a "batch-type" treatment process. Although the Latham bowl separator has a high volume yield, the constant filling and emptying of this bowl wastes time; thus, the process is considered less efficient with respect to time.

Prior photopheresis and apheresis systems and methods usually require batch processes and therefore take several hours to treat a patient or to obtain a sufficient supply of separated blood fragments. Furthermore, the systems are very complex to manufacture. It is a constant objective to reduce the time it takes to perform a complete photopheresis treatment session. Another objective is to reduce the amount of blood that must be drawn form a patient and processed in closed-loop processes per photopheresis treatment session. Yet another objective to increase the amount of white blood cell yield or obtain a cleaner cut of buffy coat per volume of whole blood processed.

Additionally, apheresis systems and methods have also been proposed and used which involve separation of blood into various components, and also involve systems pumping and valving systems which are difficult to manufacture or operate. Prior photopheresis and apheresis systems and methods usually require batch processes and therefore take several hours to treat a patient or to obtain a sufficient supply of separated blood components. Furthermore, the systems are very complex to manufacture, especially the fluid flow controllers and valving systems.

In known photopheresis systems, a disposable kit is provided that is loaded into a permanent piece of hardware. The disposable kit contain complex tubing that is used to carry blood fluids to and from the various devices included in the kit, such as a centrifuge bowl, an irradiation chamber, and various bags for delivering and/or collecting blood fluids. Known disposable kits often contain a cassette, or other controller mechanism, for controlling the flow of blood fluids throughout the disposable kit and to and from the patient. Disposable kits are used only once and must be replaced or disposed after each treatment session. In performing a treatment process, the kit is connected to patient to form a closed-loop system and the various devices of the disposable kit are loaded into a permanent piece of equipment used to drive blood fluids throughout the disposable kit as necessary. Once loaded, the permanent blood drive system drives the blood fluids through the kit's fluid circuitry.

A very real advancement in photopheresis systems would result if the size, manufacturing complexity, manufacturing costs, and tubing within the disposable kit could be reduced, even at the cost of a more complex blood driving system. This is because the blood driving system represents permanent reusable equipment, whereas a new sterile disposable kit must be used each time.

Known disposable photopheresis kits are difficult and expensive to manufacture, especially the valving and pumping mechanisms within the cassette. Additionally, prior photopheresis and apheresis systems and methods usually require batch processes and therefore take several hours to treat a patient or to obtain a sufficient supply of separated blood fragments. It is a constant object to reduce the time it takes to perform a complete photopheresis or apheresis treatment session. Another object is to reduce the amount of blood that must be drawn form a patient and processed in closed-loop processes per photopheresis treatment session. Yet another object to increase the amount of white blood cell yield or obtain a cleaner cut of buffy coat per volume of whole blood processed. Still another object is to reduce the costs and complexity associated with making the disposable kits used.

DISCLOSURE OF THE INVENTION

The present invention provides for improved methods and apparatus of collecting blood components and for methods and apparatus for photopheresis treatment. The invention, in one aspect, comprises an apparatus for controlling movement of fluid and separated component of the fluid comprising a cassette having a housing formed by joining a rigid plastic cover and a rigid plastic base; said housing having a wall wherein the wall has a plurality of wall openings or slots; a plurality of first flexible tubings extending out of or entering the housing through the openings or slots; and a plurality of second flexible tubing extending through the wall openings or slots and are secured in a raceway located on a bottom surface of the base.

In another embodiment the invention provides for an apparatus for controlling movement of fluid and separated component of the fluid comprising a cassette having a housing formed by joining a rigid plastic cover and a rigid plastic base; said rigid plastic cover having a top surface, a bottom surface, and a wall having a plurality of openings; said rigid plastic base having a top surface, a bottom surface, and a wall having a plurality of openings adapted to overlap with the openings of the wall of the cover; and plurality of first flexible tubings extending out of or entering the housing; a plurality of second flexible tubing secured in a depressed raceway located on the bottom surface of the base, said second flexible tubing are located outside of the housing and extending through or entering the openings of the wall of the base.

In another embodiment the cassette comprises a rigid plastic cover having a top surface, a bottom surface, and a wall having a plurality of openings; said rigid plastic base having a top surface, a bottom surface, and a wall having a plurality of openings adapted to overlap with the openings of the wall of the cover; a plurality of first flexible tubings extending out of or entering the housing; a plurality of second flexible tubing secured in a depressed raceway located on the bottom surface of the base, said second flexible tubing are located outside of the housing and extending through or entering the openings of the wall of the base; and a plurality of apertures located on said base section and expose the first flexible tubings inside the housing so that fluid flow through the exposed section can be prevented when external pressure means is exerted on the exposed section through the apertures.

In another embodiment the invention provides for an apparatus for controlling movement of fluid and separated component of the fluid comprising a cassette having a housing formed by joining a rigid plastic cover and a rigid plastic base; said rigid plastic cover having a top surface, a bottom surface, and a wall having a plurality of openings; said rigid plastic base having a top surface, a bottom surface, and a plurality of apertures through the top and bottom surfaces, and a wall having a plurality of openings adapted to overlap with the openings of the wall of the cover; said top surface of the base comprises a first upper level and a first lower level, wherein the first lower level has a plurality of first flexible tubings, secured by raceways, for one or more of a) connecting to other tubings through multitube connectors, b) extending out of or entering the housing, or c) forming first flexible tube loops having one end extending out of the housing and one end entering the housing; said plurality of apertures are located on the first lower level and expose at least one section of the first flexible tubing inside the housing so that fluid flow through the exposed section can be prevented when external pressure means is exerted on the exposed section through the apertures; and said bottom surface of the base comprise a second upper level and a second lower level, wherein the second lower level has a plurality of second flexible tubing outside of the housing and secured by raceways on said second lower level for one or more of extending through or entering the openings of the wall of the base or forming second flexible tube loops having one end extending out of the wall and one end entering the wall of the base.

In another embodiment, the cassette further comprises a plurality of multi-tube connector located inside the housing adapted to connect sections of the first flexible tubings and from zero to three multitube connectors located outside of the housing adapted to connect to flexible tubing extending from or entering the housing.

In another embodiment, the cassette comprises a five-tube connector and two three-tube connector located inside the housing and one three-tube connector located outside of the housing.

In another embodiment, the cassette has a plurality of occluder bars located above the first lower level surface to close off an exposed section of the first flexible tubing located inside the housing by the external pressure means through the apertures and thereby prevent fluid flow; and a plurality of occluder bars located on the second lower level of the bottom surface of the base to close off a section of the second flexible tubing located outside of the housing by pressure means and thereby prevent fluid flow.

In a preferred embodiment the cassette has five apertures located on the first lower level five and five flexible tube loops wherein three of the five flexible tube loops are first flexible tube loops extends from inside the housing.

In another embodiment the cassette further comprises a filter in fluid communication with one first flexible tubing and one second flexible tubing, and in another preferred embodiment the cassette has a recordable smartcard on which are electronically recorded identification data.

In a preferred embodiment the apparatus for controlling movement of fluid and separated component of the fluid further comprises a pressure dome that is connected in series between the cassette and a centrifuge bowl for measuring a pressure of a fluid inside a flexible tubing connecting the cassette to the centrifuge bowl. In another preferred embodiment the apparatus further comprises a pressure dome that is connected in series between a blood donor or patient and the cassette for measuring a pressure of a blood or blood component in a flexible tubing connecting the patient to the cassette.

In an another preferred embodiment of the invention the apparatus comprising a cassette for controlling movement of blood and separated blood components, the cassette comprising: a housing formed by joining a rigid plastic cover and a rigid plastic base; said rigid plastic cover having a top surface, a bottom surface, and a wall having a plurality of openings; said rigid plastic base having a top surface, a bottom surface, and a plurality of apertures through the top and bottom surfaces, and a wall having a plurality of openings adapted to overlap with the openings of the wall of the cover; said top surface of the base comprises a first upper level and a first lower level, wherein the first lower level has a plurality of first flexible tubings, secured by raceways, for one or more of a) connecting to other tubings through multitube connectors, b) extending out of or entering the housing, or c) forming first flexible tube loops having one end extending out of the housing and one end entering the housing; said plurality of apertures are located on the first lower level and expose at least one section of the first flexible tubing inside the housing so that fluid flow through the exposed section can be prevented when an actuator exerts pressure on the exposed section through the apertures against a first occluder bar located above the first lower level surface;

said bottom surface of the base comprise a second upper level and a second lower level, wherein the second lower level has a plurality of second flexible tubing outside of the housing and secured by raceways on said second lower level for one or more of extending through or entering the openings of the wall of the base or forming second flexible tube loops having one end extending out of the wall and one end entering the wall of the base; and wherein fluid flowing through the second flexible tubing can be prevented when another actuator exerts pressure on the tubing against a second occluder bar located on the second lower level of the bottom surface of the base.

Another preferred embodiment of the cassette comprises a filter in fluid communication with one first flexible tubing and one second second flexible tubing, and a recordable smartcard on which are electronically recorded identification data.

Another embodiment of the cassette has three first tube loops extend from inside the housing, two second tube loops extends from the lower level of the bottom surface of the base and five apertures on the base.

In a preferred embodiment of the invention, the apparatus further comprises a pressure dome that is connected in series between the cassette and a centrifuge bowl for measuring a pressure of a fluid inside a flexible tubing connecting the cassette to the centrifuge bowl, and a pressure dome that is connected in series between a blood donor or patient and the cassette for measuring a pressure of a blood or blood component in a flexible tubing connecting the patient to the cassette; and said flexible tubings having fluid communications with said pressure domes.

In an embodiment of the invention the first separated fluid component comprises red blood cells. In another embodiment of the invention, the second separated fluid component comprises buffy coat.

In another preferred embodiment the apparatus further comprises a centrifuge bowl for separating the components of a fluid, and flexible tubes fluidly connecting between the bowl and the cassette, the bowl comprising an outer housing having a housing outlet, said outer housing adapted for rotation about a center axis; said outer housing containing a core providing a separation volume between said core and said outer housing; said core has a core end and is connected with said outer housing for rotation therewith, said core end having a lumen connector; a first lumen for providing fluid communication from the housing outlet through the lumen connector and then radially outward through the core to the fluid separation volume; a second lumen providing fluid communications from the housing outlet extending axially along center axis to housing floor; a connection sleeve which forms with the lumen connector a chamber and provide fluid communications between the housing outlet and the separation volume; and the flexible tubes comprising a first flexible tube for inflowing of the fluid from the cassette to the first bowl channel; a second flexible tube for removing a the first separated fluid component of the second bowl channel; and a third flexible tube for removing a second separated fluid component from the bowl chamber to the cassette. In an embodiment of the invention, the first separated fluid component comprises red blood cells, and in another embodiment of the invention, the second separated fluid component comprises buffy coat. In an embodiment of the invention, the connection sleeve is adapted to be secured to the centrifuge bowl near said housing outlet of said outer housing for rotation therewith, said connection sleeve adapted to fluidly connect a first bowl channel, a second bowl channel, and a bowl chamber.

In another embodiment of the invention, the extracorporeal photopheresis apparatus comprises an irradiation chamber having a first port connected to a flexible tube for carrying buffy coat from the cassette to the irradiation chamber; a second port connected to a flexible tube for carrying irradiated buffy coat from the irradiation chamber to the cassette; the irradiation chamber having a rigid first plate having a first surface and a second surface the second surface having a groove boundary formed by two ridges surrounding a plurality of groove partitions formed by two ridges; a rigid second plate having a first surface and a second surface, the second surface having a ridge boundary surrounding a plurality of ridge partitions; wherein the groove boundary and groove partitions of the second surface of the rigid first plate is contacted with the ridge boundary and ridge partitions of the second surface of the rigid second plate thereby forming a chamber; the chamber defined by a boundary formed by the joining of the groove boundary and the ridge boundary surrounding the plurality of partitions formed by the joining of the groove partitions and the ridge partition wherein a plurality of channels are formed by the partitions providing fluid communication with the first port and second port.

In another embodiment of the invention, the apparatus comprises a cassette having flexible tubes inside a cassette housing and on the bottom surface of the cassette housing, a saline inlet tube; a dual chamber bag having a treatment chamber and a plasma collection chamber, the plasma collection chamber having an inlet tube for flowing plasma from the cassette and an outlet tube for flowing plasma to the cassette; an anticoagulant inlet tube for flowing anticoagulant to the cassette and an outlet tube for flowing anticoagulant out to a multiport connector joining a tube for flowing blood from a patient to the cassette; an irradiation chamber having an inlet tube for flowing buffy coat from the cassette and an outlet tube for flowing irradiated buffy coat to the cassette; a separation bowl having one tube for flowing blood to the separation chamber and at least two tubes for flowing separate blood fragments from the separation chamber; means to withdraw blood from a patient comprising the tube for flowing blood from the patient to the cassette and means for connecting a needle; and means to return blood fractions to the patient comprising a tube from the cassette.

In another embodiment of the invention, the first and second flexible tube loops of the cassette comprise an anticoagulant pump loop, a whole blood pump loop, a return to patient pump loop, a red blood pump loop, and a buffy coat recirculation pump loop.

An aspect of the present invention is a method of collecting a desired lower density buffy coat or a higher density buffy coat component of blood comprising: providing a separator having an inlet, a first outlet, and a second outlet; drawing whole blood from a patient or a blood donor; adding an anticoagulant fluid to the whole blood in a predetermined ratio to form a mixture of whole blood and anticoagulant fluid; pumping the mixture of whole blood and anticoagulant fluid into the separator via the inlet at a selected inlet rate; separating the mixture into blood components of different densities; withdrawing plasma and red blood cells from the separator while continuing to pump the mixture of whole blood and anticoagulant fluid into the separator, the plasma and red blood cells being withdrawn at rates so as to build up buffy coat in the separator, the plasma being withdrawn via the first outlet and the red blood cells being withdrawn via the second outlet; and upon a predetermined amount of buffy coat building up in the separator, collecting the buffy coat from the separator by discontinuing the withdrawal of red blood cells from the second outlet, thereby causing the red blood cells to push the buffy coat out of the separator via the first outlet; rinsing the separator with a saline solution; pumping the collected buffy coat back to the separator via the inlet; and separating the collected buffy coat into a higher density buffy coat layer and a lower density buffy coat layer.

In another embodiment, the method of the invention further comprise collecting the higher density buffy coat layer by pumping out the higher density buffy coat layer through the second outlet and replacing the displaced volume of higher density buffy coat layer with saline through the inlet; and discontinuing collecting the higher density buffy coat layer after a desired volume of the higher density buffy coat layer has been collected.

In another embodiment, the method of the invention further comprise collecting the lower density buffy coat layer by pumping out the lower density buffy coat layer through the first outlet and replacing the displaced volume of lower density buffy coat layer with saline through the inlet; discontinuing collecting the lower density buffy coat layer after a desired volume of the lower density buffy coat layer has been collected.

Another embodiment of the invention comprises a method for collecting a desired lower density buffy coat component or a higher density buffy coat component comprising: providing a separator having an inlet, a first outlet, and a second outlet; drawing whole blood from a patient or blood donor; adding an anticoagulant fluid to the whole blood in a predetermined ratio to form a mixture of whole blood and anticoagulant fluid; pumping the mixture of whole blood and anticoagulant fluid into the separator via the inlet at a selected inlet rate; separating the mixture into blood components of different densities; withdrawing plasma and red blood cells from the separator while continuing to pump the mixture of whole blood and anticoagulant fluid into the separator, the plasma and red blood cells being withdrawn at rates so as to build up buffy coat in the separator, the plasma being withdrawn via the first outlet and the red blood cells being withdrawn via the second outlet; and discontinuing pumping the mixture of whole blood and anticoagulant fluid into the separator after a predetermined amount of buffy coat building up in the separator; withdrawing residual red blood cells from the second outlet until a bowl sensor has determined that the red blood cells have been removed from the bowl; and separating the predermined amount of buffy coat into a higher density buffy coat layer and a lower density buffy coat layer.

In another embodiment the method for collecting a desired higher density buffy coat component comprises collecting the higher density buffy coat layer by pumping out the higher density buffy coat layer through the second outlet and replacing the displaced volume of higher density buffy coat layer with saline through the inlet; and discontinuing collecting the higher density buffy coat layer after a desired volume of the higher density buffy coat layer has been collected.

In another embodiment the method for collecting a desired lower density buffy coat component comprises collecting the lower density buffy coat layer by pumping out the lower density buffy coat layer through the first outlet and replacing the displaced volume of lower density buffy coat layer with saline through the inlet; discontinuing collecting the lower density buffy coat layer after a desired volume of the lower density buffy coat layer has been collected.

In another embodiment of the invention, an extracorporeal photopheresis treatment is performed on a desired lower or higher density buffy coat component comprising injecting a photoactivation chemical into the collected higher or lower density buffy coat layer; and irradiating the collected higher or lower density buffy coat layer within an irradiation chamber until a predetermined amount of energy has been transferred to the collected higher or lower density buffy coat layer; passing the irradiated higher or lower density buffy coat layer through a filter; and returning the irradiated higher or lower buffy coat layer to the patient or blood donor.

BRIEF DESCRIPTION OF THE DRAWINGS

The invention is described in detail with respect to the accompanying drawings, which illustrate an embodiment of the inventive apparatus, assemblies, systems, and methods.

FIG. 44 shows an exploded side view of the bottom core and a lower plate of FIG. 43A.

FIG. 59A shows a top view of another cassette with the cover removed and showing internal tubular circuitry inside the housing of the cassette for use in photopheresis therapy embodying features of the present invention.

MODES FOR CARRYING OUT THE INVENTION

Features of the present invention are embodied in the permanent blood driving equipment, the disposable photopheresis kit, the various devices which make up the disposable kit, and the corresponding treatment process. The following written description is outlined as follows:

I. Disposable Photopheresis Kits
   A. Cassette for Controlling Fluid Flow
      1. Filter Assembly
      A1. Cassette 2 for Controlling Fluid Flow
   B. Irradiation Chambers
   C. Centrifuge Bowl
      1. Drive Tube II. Permanent Tower System
   A Photoactivation Chamber
   B. Centrifuge Chamber
   C. Fluid Flow Control Deck
      1. Cassette Clamping Mechanism
      2. Self-Loading Peristaltic Pumps
   D. Infra-Red Communication III. Photopheresis Treatment Processes The above-outline is included to facilitate understanding of the features of the present invention. The outline is not limiting of the present invention and is not intended to categorize or limit any aspect of the invention. The inventions are described and illustrated in sufficient detail that those skilled in this art can readily make and use them. However, various alternatives, modifications, and improvements should become readily apparent without departing from the spirit and scope of the invention. Specifically, while the invention is described in the context of a disposable kit and permanent blood drive system for use in photopheresis therapy, certain aspects of the invention are not so limited and are applicable to kits and systems used for rendering other therapies, such as apheresis or any other extracorporeal blood treatment therapy.

Disposable Photopheresis Kit

Figure 1:
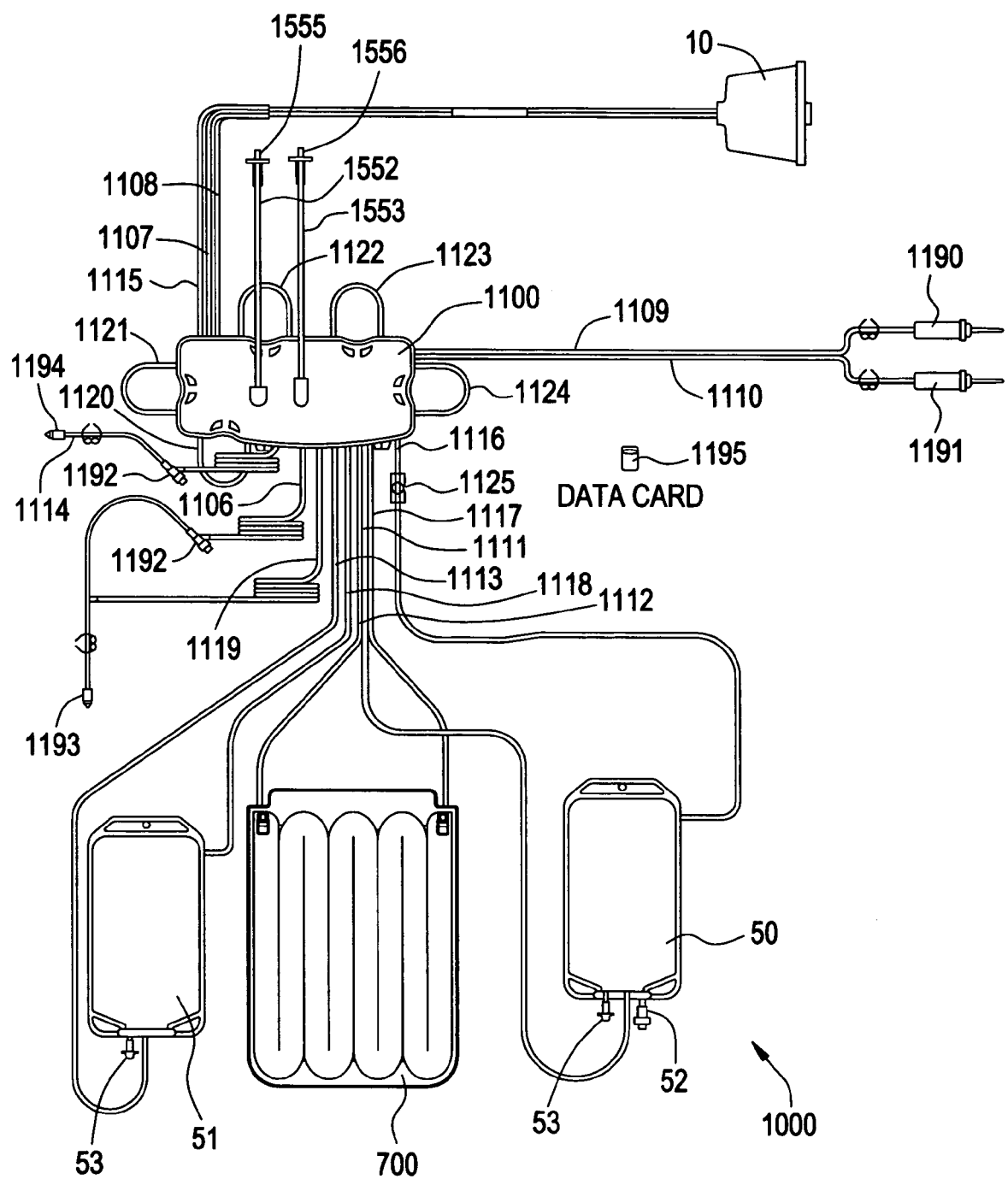
FIG. 1 is a schematic representation of an embodiment of a disposable kit for use in photopheresis therapy embodying features of the present invention.
Figure 17:
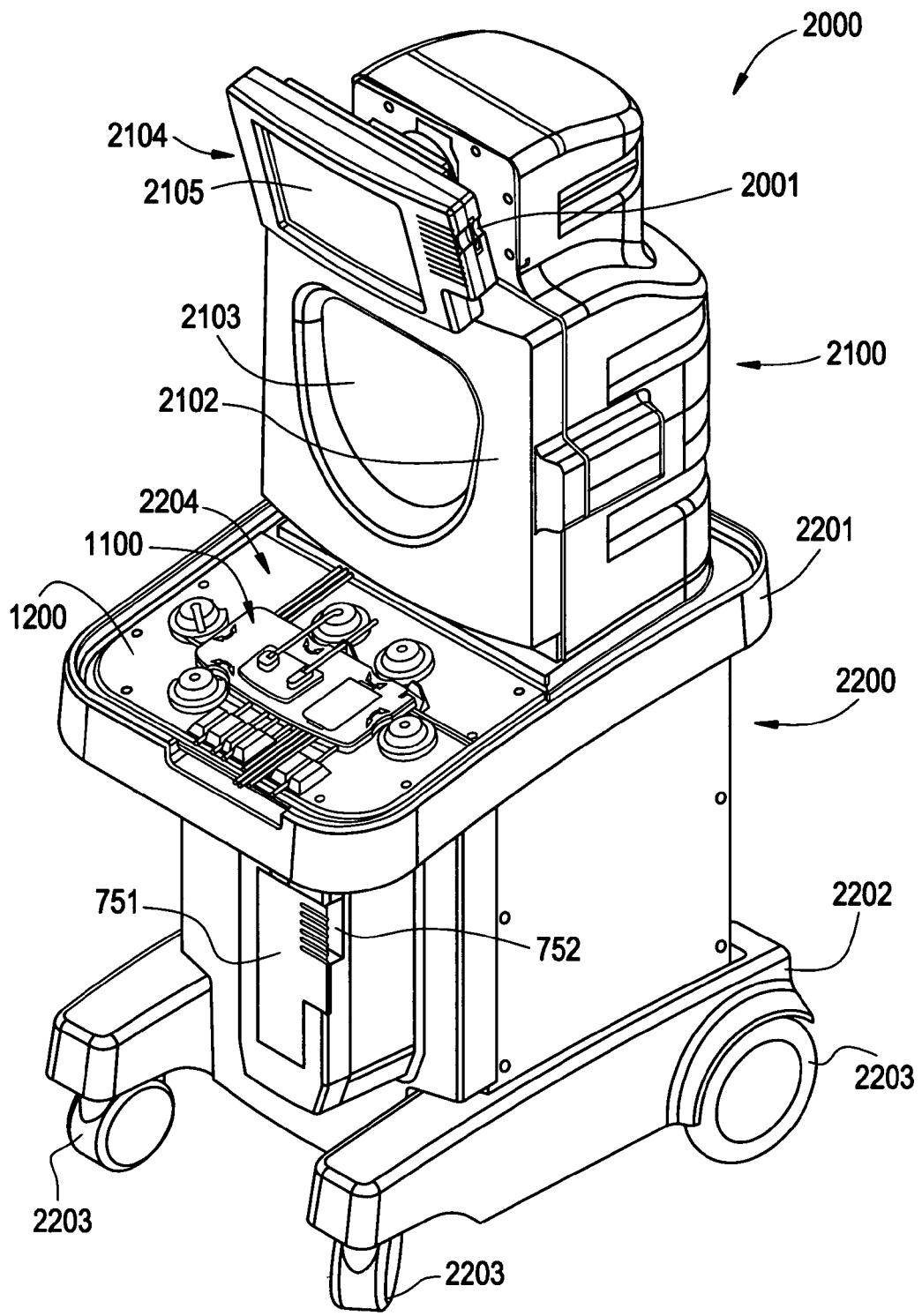
FIG. 17 is an elevated perspective view of an embodiment of a permanent tower system for use in conjunction with a disposable kit for facilitating a photopheresis therapy session.

FIG. 1 illustrates disposable photopheresis kit 1000 embodying features of the present invention. It is necessary that a new disposable sterile kit be used for each therapy session. In order to facilitate the circulation of fluids through photopheresis kit 1000, and to treat blood fluids circulating therethrough, photopheresis kit 1000 is installed in permanent tower system 2000 (FIG. 17). The installation of photopheresis kit 1000 into tower system 2000 is described in detail below.

Photopheresis kit 1000 comprises cassette 1100, centrifuge bowl 10, irradiation chamber 700, hematocrit sensor 1125, removable data card 1195, treatment bag 50, and plasma collection bag 51. Photopheresis kit 1000 further comprises saline connector spike 1190 and anticoagulant connector spike 1191 for respectively connecting saline and anticoagulant fluid bags (not shown). Photopheresis kit 1000 has all the necessary tubing and connectors to fluidly connect all devices and to route the circulation of fluids during a photopheresis treatment session. All tubing is sterile medical grade flexible tubing. Triport connectors 1192 are provided at various positions for the introduction of fluids into the tubing if necessary.

Needle adapters 1193 and 1194 are provided for respectively connecting photopheresis kit 1000 to needles for drawing whole blood from a patient and returning blood fluids to the patient. Alternatively, photopheresis kit 1000 can be adapted to use a single needle to both draw whole blood from the patient and return blood fluids to the patient. However, a two needle kit is preferred because of the ability to simultaneously draw whole blood and return blood fluids to the patient. When a patient is hooked up to photopheresis kit 1000, a closed loop system is formed.

Figure 10:
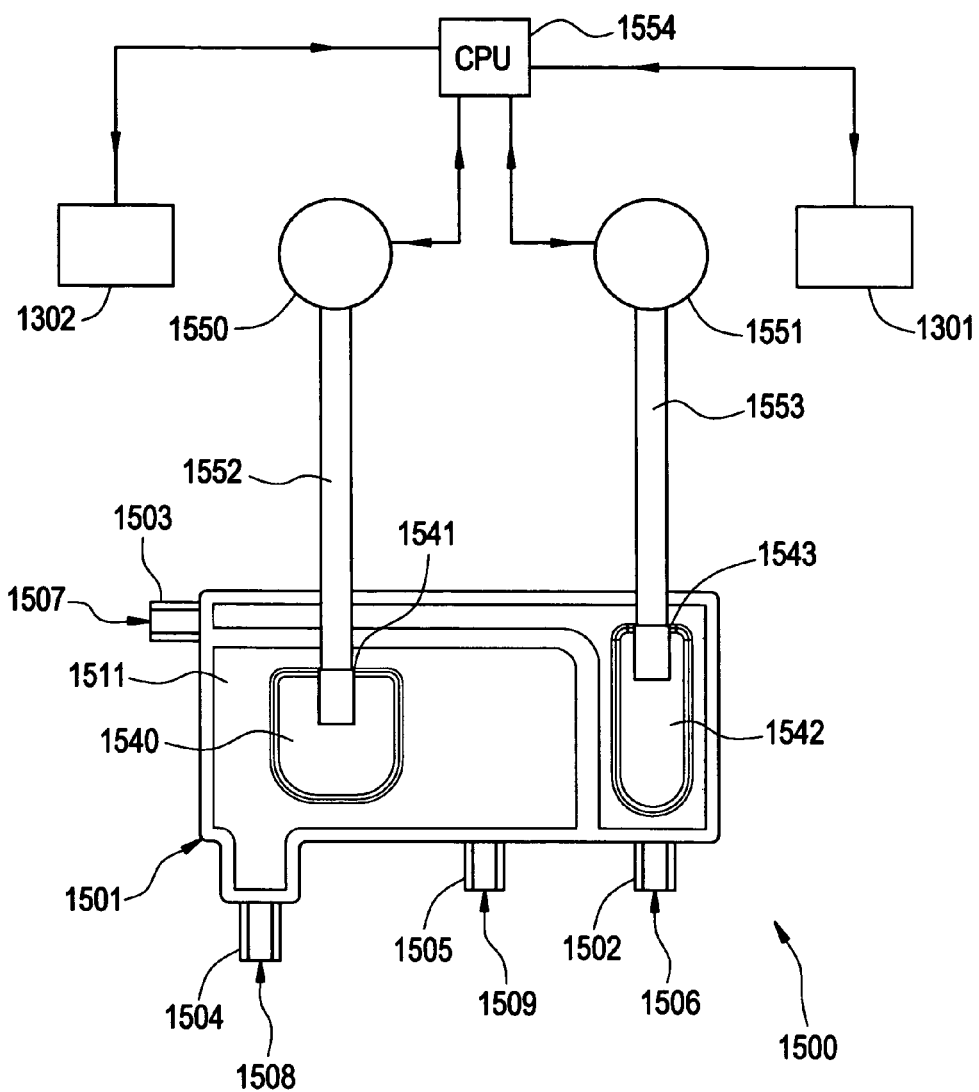
FIG. 10 is schematic representation of the filter assembly of FIG. 6 coupled to pressure sensors and a data processor.

Cassette 1100 acts both as a tube organizer and a fluid flow router. Irradiation chamber 700 is used to expose blood fluids to UV light. Centrifuge bowl 10 separates whole blood into its different components according to density. Treatment bag 50 is a 1000 mL three port bag. Straight bond port 52 is used to inject a photoactivatable or photosensitive compound into treatment bag 50. Plasma collection bag 51 is 1000 mL two port bag. Both treatment bag 50 and plasma collection bag 51 have a hinged cap spike tube 53 which can be used for drainage if necessary. Photopheresis kit 1000 further comprises hydrophobic filters 1555 and 1556 which are adapted to connect to pressure transducers 1550 and 1551 to filter 1500 via vent tubes 1552 and 1553 for monitoring and controlling the pressures within tubes connecting the patient (FIG. 10). Monitoring the pressure helps ensure that the kit is operating within safe pressure limits. The individual devices of photopheresis kit 1000, and their functioning, are discussed below in detail.

Disposable Photopheresis Kit 2

Figure 56A:
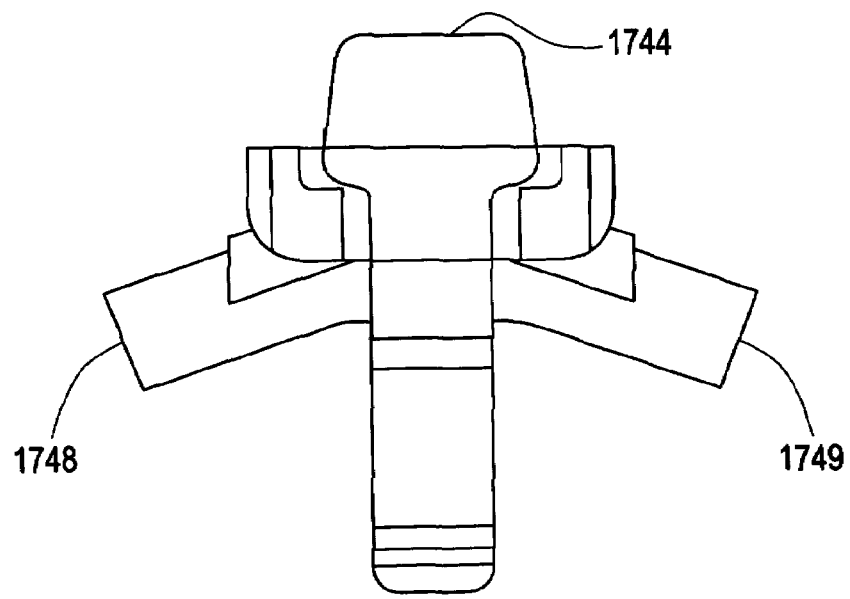
FIG. 56A shows a side view of a pressure dome
Figure 56:
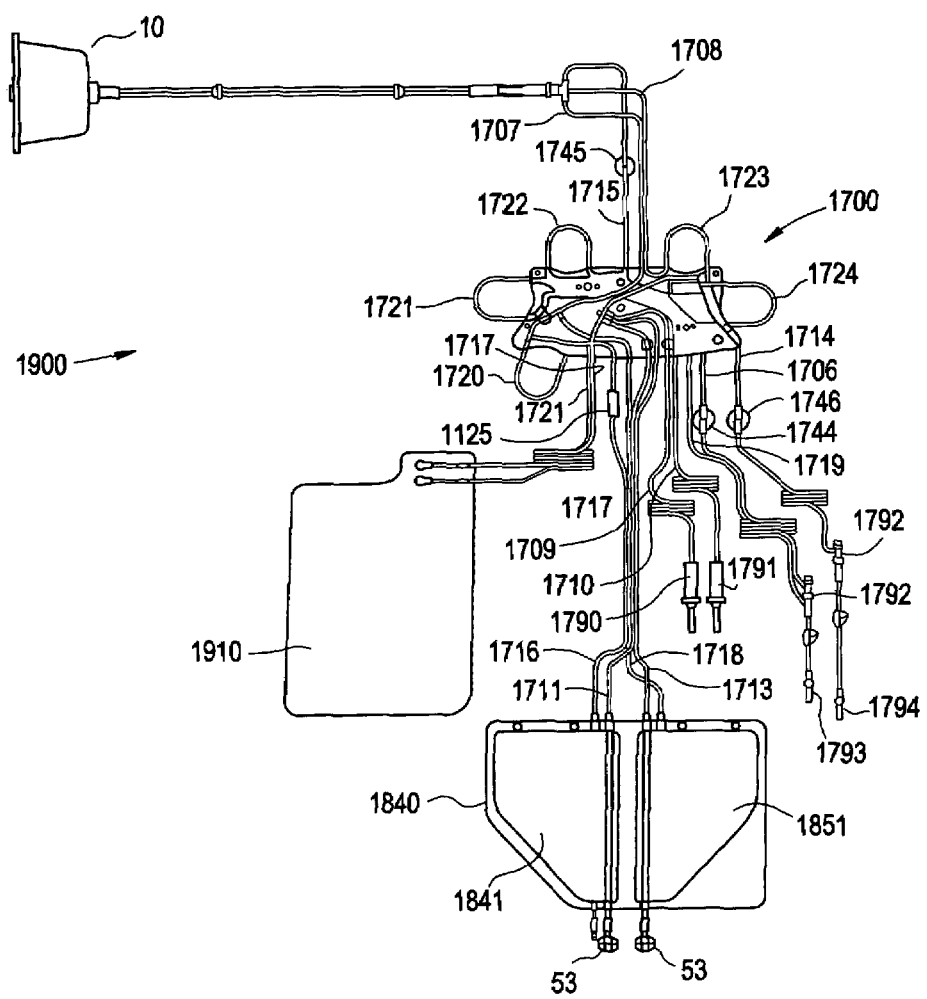
FIG. 56 is a schematic representation of another embodiment of a disposable kit for use in photopheresis therapy embodying features of the present invention.
Figure 66:
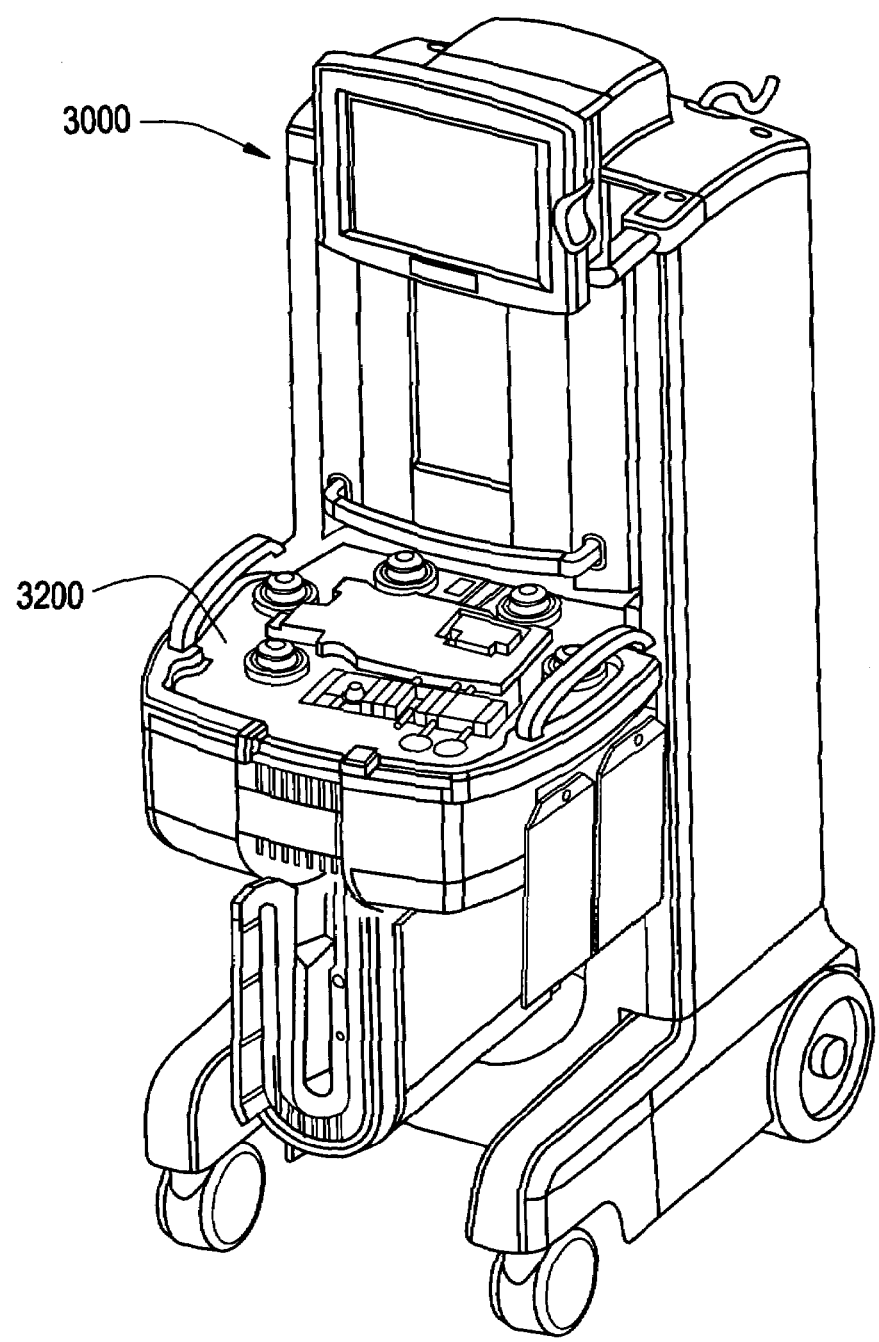
FIG. 66 is an elevated perspective view of another embodiment of a permanent tower system for use in conjunction with the disposable kit of FIG. 56 for facilitating a photopheresis therapy session.

FIG. 56 illustrates another disposable photopheresis kit 1900 embodying features of the present invention. The disposable photopheresis kit 1900 is contemplated to be used with another permanent tower system 3000. A new disposable sterile kit 1900 is installed in a permanent tower system 3000 (FIG. 66) for the extracorporeal photopheresis treatment of blood fluids, preferably the buffy coat component of blood. Photopheresis kit 1900 comprises cassette 1700, centrifuge bowl 10, irradiation chamber 1910, hematocrit sensor 1125, pressure domes 1744, 1745, and 1746, removable data card 1795, and a dual chamber bag 1840 having a treatment chamber 1841, and plasma collection chamber 1851. Photopheresis kit 1900 further comprises saline connector spike 1790 and anticoagulant connector spike 1791 for respectively connecting saline and anticoagulant fluid bags (not shown). Needle adapters 1793 and 1794 are preferably provided for respectively connecting photopheresis kit 1900 to needles for drawing whole blood from a patient and returning blood fluids to the patient. Alternatively, photopheresis kit 1900 can be adapted to use a single needle to both draw whole blood from the patient and return blood fluids to the patient. When a patient is hooked up to photopheresis kit 1900, a closed loop system is formed. Photopheresis kit 1900 has all the necessary tubing and connectors to fluidly connect all devices and to route the circulation of fluids during a photopheresis treatment session. All tubing is sterile medical grade flexible tubing. Multiport connectors 1792 and 1792A are provided at various positions for the introduction of fluids into the tubing if necessary.

Figure 57:
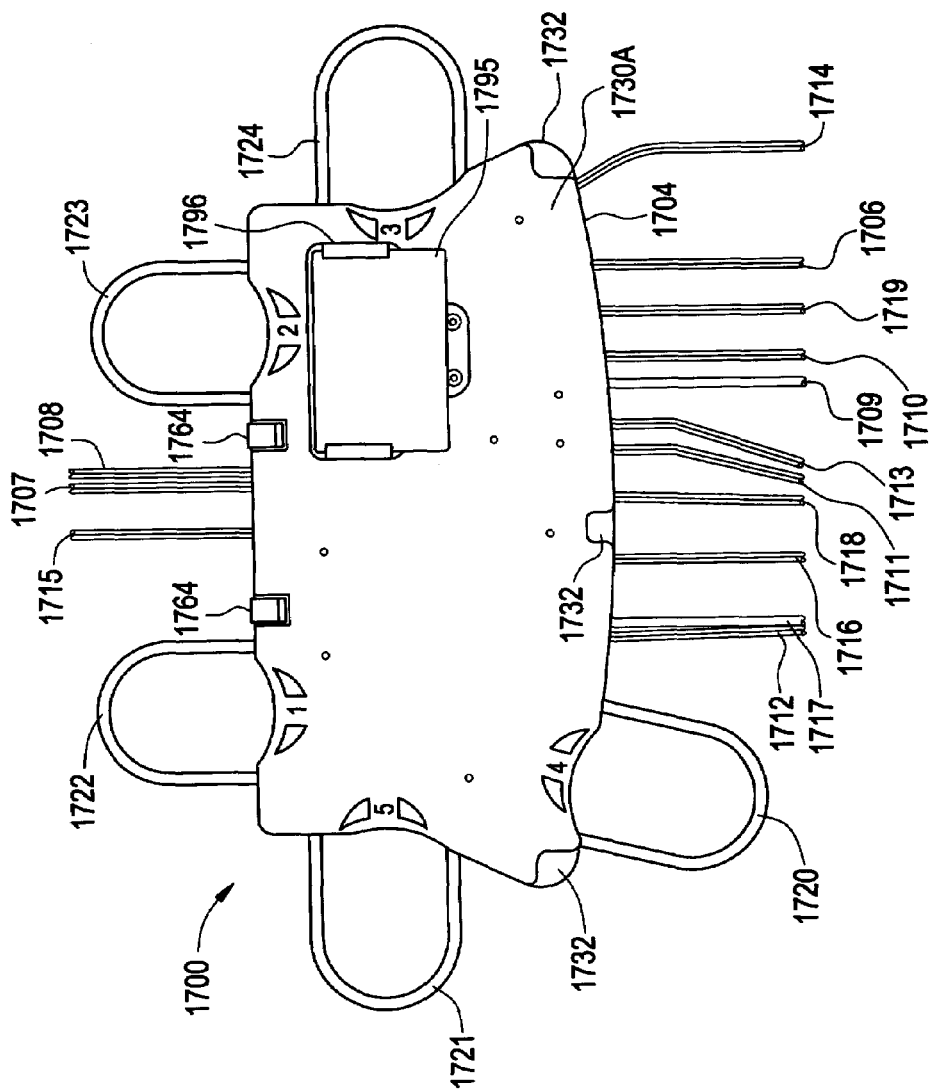
FIG. 57 shows a top view of another embodiment of a cassette for controlling fluid flow in the disposable photopheresis kit of FIG. 56.

Pressure domes 1744, 1745, and 1746 are for measurement of fluid pressures in the tubings. The pressure dome made of a biocompatible material, e.g., a polycarbonate plastic, comprises of a housing produced by a one-piece plastic injection molding. A representative pressure dome is pressure dome 1744 that transmits pressure signal via a flexible membrane (not shown) that is in fluid communication with the fluid inside tubing via an inlet port 1748 and an outlet port 1749 (FIG. 56A) to a reusable pressure sensor, e.g., pressure transducer 1754. The flexible membrane is prefererably made of a silicone material or some other suitable biocompatible material. The flexible silicone dome diaphragms apply a pressure to pressure sensors, e.g., piezoresistive transducers, 1754, 1755, and 1756 located in a housing on deck (FIG. 57). Examples of a pressure dome and a pressure transducer are the SP844 Physiological Pressure Transducer and the Domes manufactured by MEMSCAP.

Dual chamber bag 1840 comprises a 1900 mL four-port treatment chamber 1841 and a 1900 mL three-port plasma collection chamber 1851. Straight bond port 1846 is used to inject a photoactivatable or photosensitive compound into treatment chamber 1841. Both treatment chamber 1841 and plasma collection chamber 1851 have a hinged cap spike tube 53 which can be used for drainage if necessary. Having a dual chamber bag containing both a treatment chamber and a plasma collection chamber simplifies the assembly of photopheresis kit 1900.

In a photopheresis treatment, cassette 1700 is secured to deck 3200 of tower system 3000 by snap-in or others methods known to one skilled in the arts. It is preferable for cassette 1700 to have a unique identifier 1795 that can function similar to the data card 1195 of cassette 1100 described below.

Cassette for Controlling Fluid Flow

Figure 2:
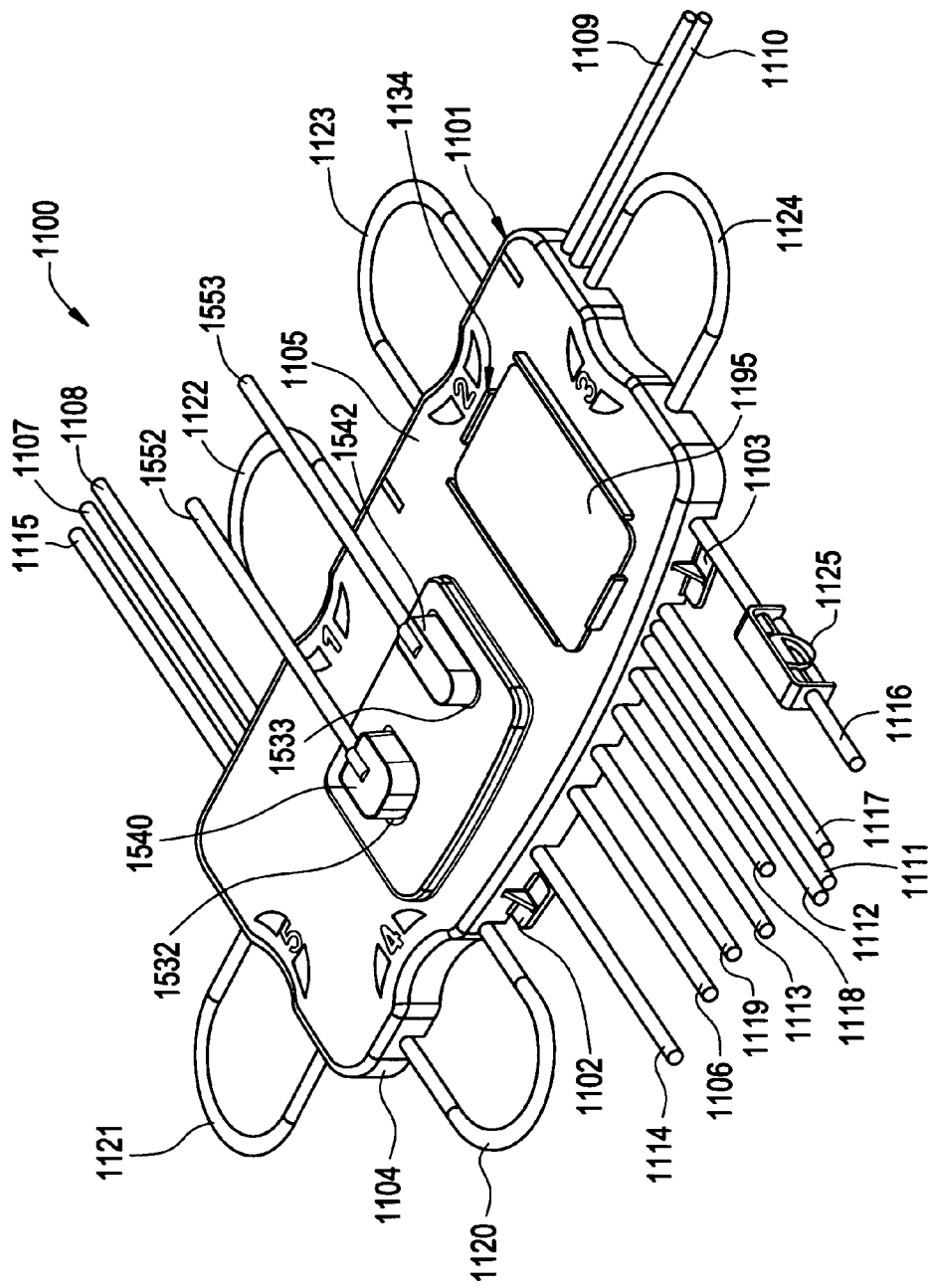
FIG. 2 is an elevated perspective view of an embodiment of a cassette for controlling fluid flow in the disposable photopheresis kit of FIG. 1.
Figure 25:
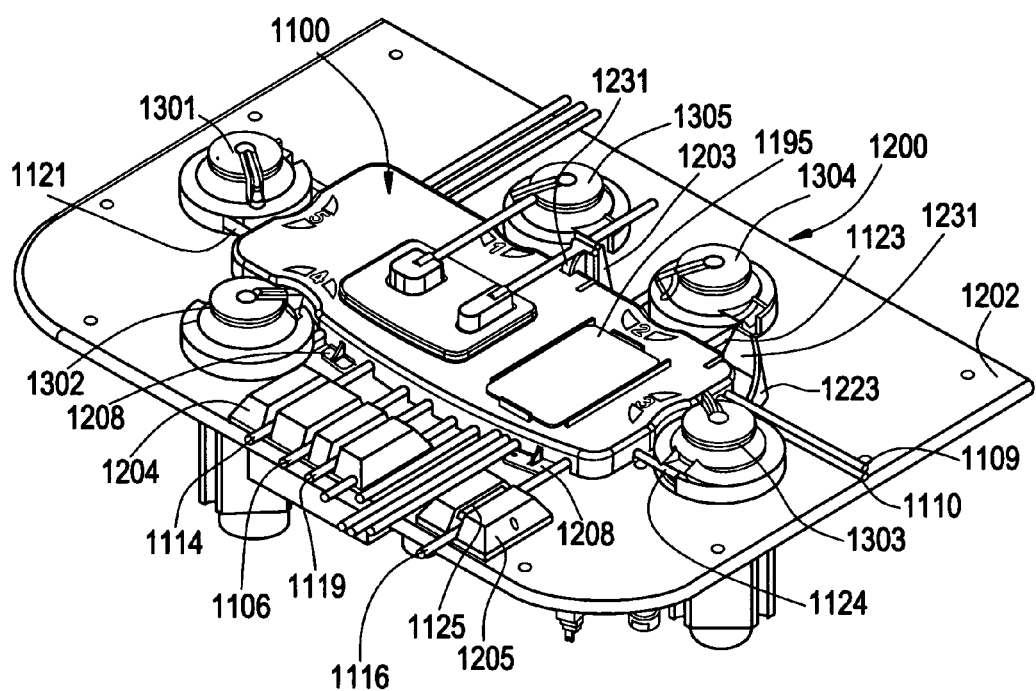
FIG. 25 is a top perspective view of the control deck of FIG. 22 with the cassette of FIG. 2 loaded thereon.

FIG. 2 shows a top perspective view of a disposable cassette 1100 for valving, pumping, and controlling the movement of blood fluids during a photopheresis treatment session. Cassette 1100 has housing 1101 that forms an internal space that acts as a casing for its various internal components and tubular circuitry. Housing 1101 is preferably made of hard plastic, but can be made of any suitably rigid material. Housing 1101 has side wall 1104 and top surface 1105. Side wall 1104 of housing 1101 has tabs 1102 and 1103 extending therefrom. During a photopheresis treatment, cassette 1100 needs to be secured to deck 1200 of tower system 2000, as is best illustrated in FIG. 25. Tabs 1102 and 1103 help position and secure cassette 1100 to deck 1200.

Figure 27:
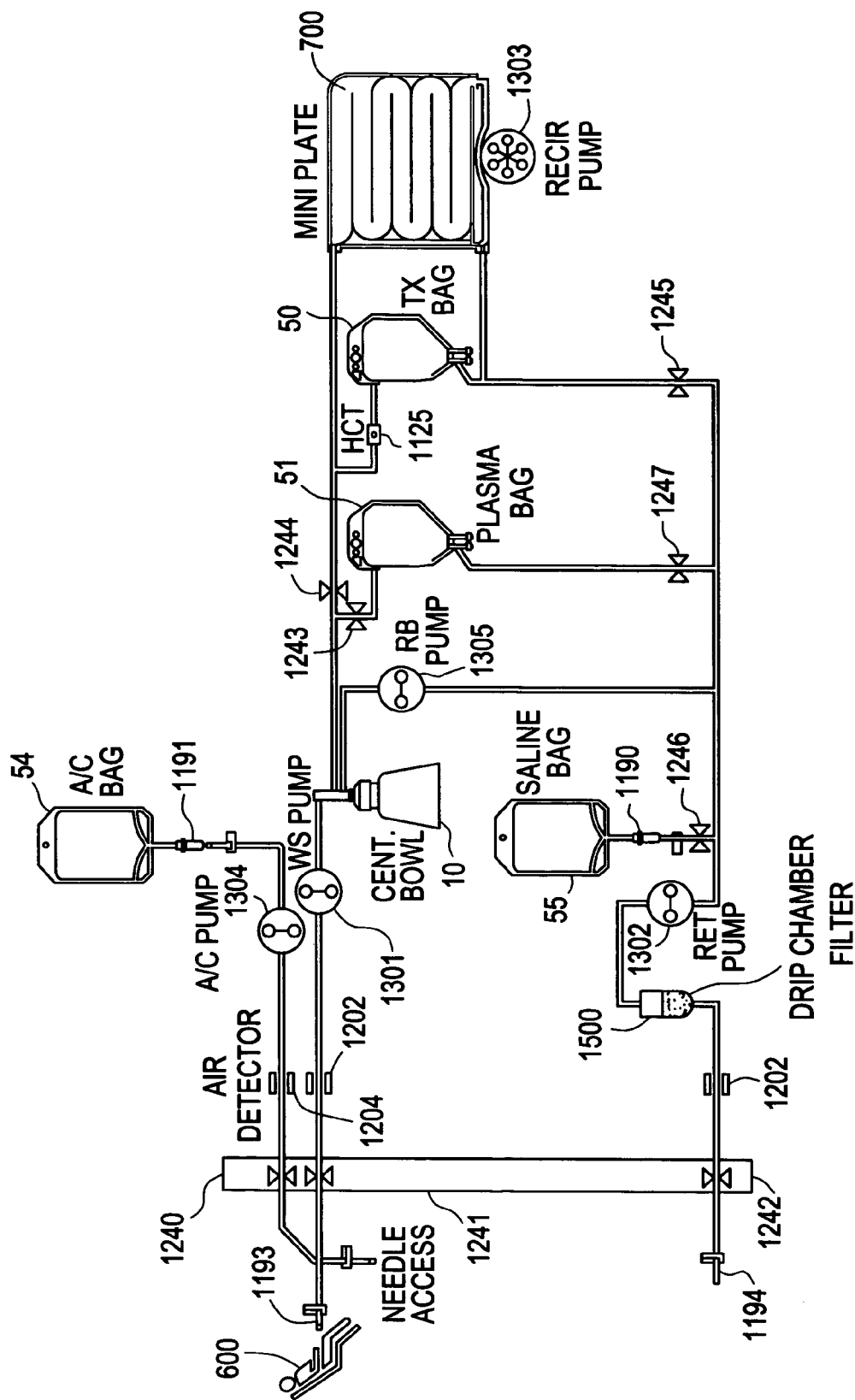
FIG. 27 is a schematic of an embodiment of the fluid flow circuit used in performing the treatment process of FIG. 26.

Cassette 1100 has fluid inlet tubes 1106, 1107, 1108, 1109, 1110, 1111, and 1112 for receiving fluids into cassette 1100, fluid outlet tubes 1114, 1115, 1116, 1117, 1118, and 1119 for expelling fluids from cassette 1100, and fluid inlet/outlet tube 1113 that can be used for both introducing and expelling fluids into and out of cassette 1100. These fluid input and output tubes fluidly couple cassette 1100 to a patient being treated, as well as the various devices of photopheresis kit 1000, such as centrifuge bowl 10, irradiation chamber 700, treatment bag 50, plasma collection bag 51, and bags containing saline, anticoagulation fluid to form a closed-loop extracorporeal fluid circuit (FIG. 27).

Figure 4:
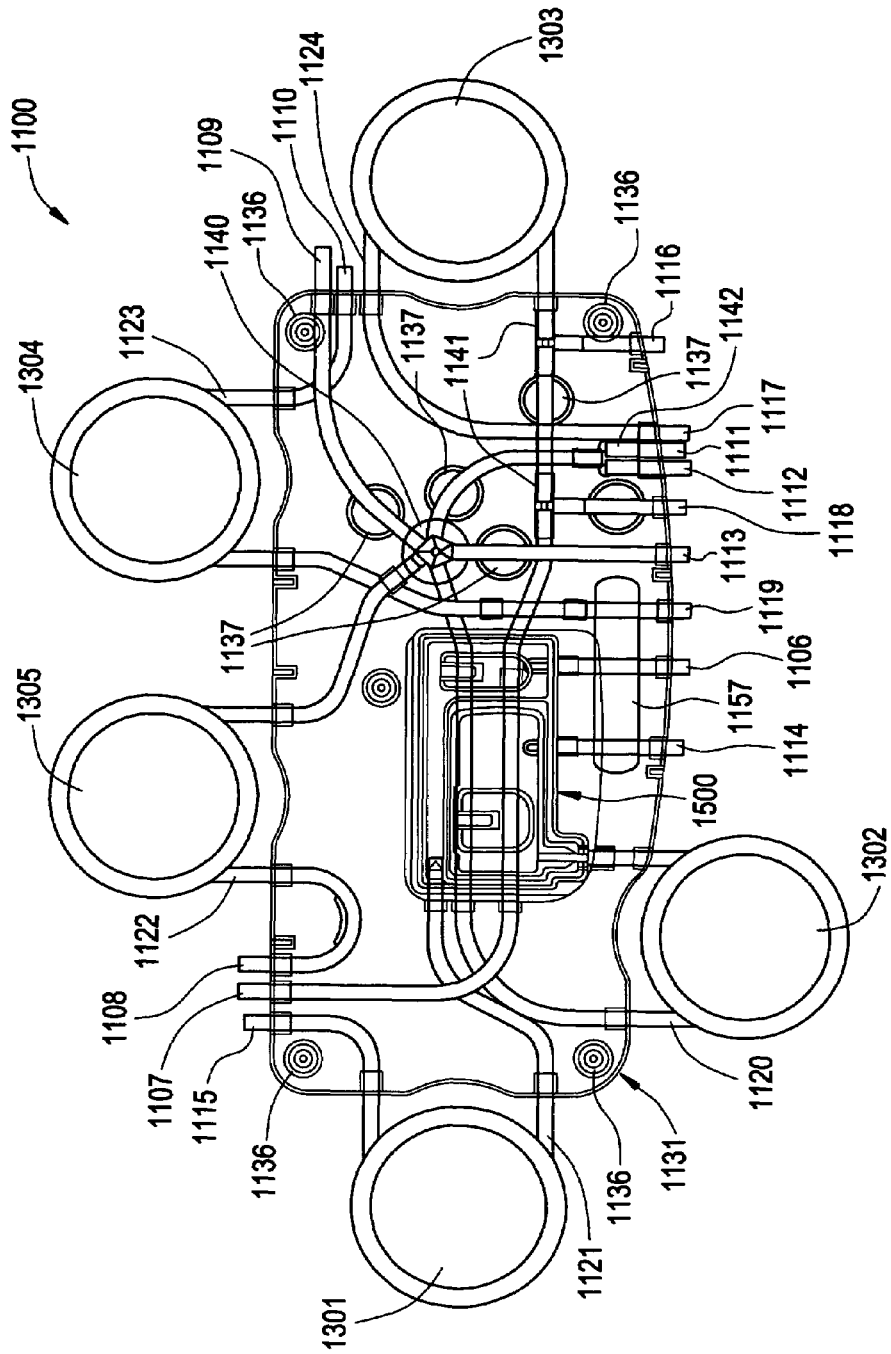
FIG. 4 is a top view of the cassette of FIG. 2 with the cover removed and showing internal tubular circuitry.

Pump tube loops 1120, 1121, 1122, 1123, and 1124 protrude from side wall 1104 of housing 1101. Pump tube loops 1120, 1121, 1122, 1123, and 1124 are provided for facilitating the circulation of fluids throughout photopheresis kit 1000 during therapy. More specifically, when cassette 1100 is secured to deck 1200 for operation, each one of said pump tube loops 1120, 1121, 1122, 1123, and 1124 are loaded into a corresponding peristaltic pump 1301, 1302, 1303, 1304, and 1305 (FIG. 4). Peristaltic pumps 1301, 1302, 1303, 1304, and 1305 drive fluid through the respective pump tube loops 1120, 1121, 1122, 1123, and 1124 in a predetermined direction, thereby driving fluid through photopheresis kit 1000 (FIG. 1) as necessary. The operation and automatic loading and unloading of peristaltic pumps 1301, 1302, 1303, 1304, and 1305 is discussed in detail below with respect to FIGS. 28-33.

Figure 3:
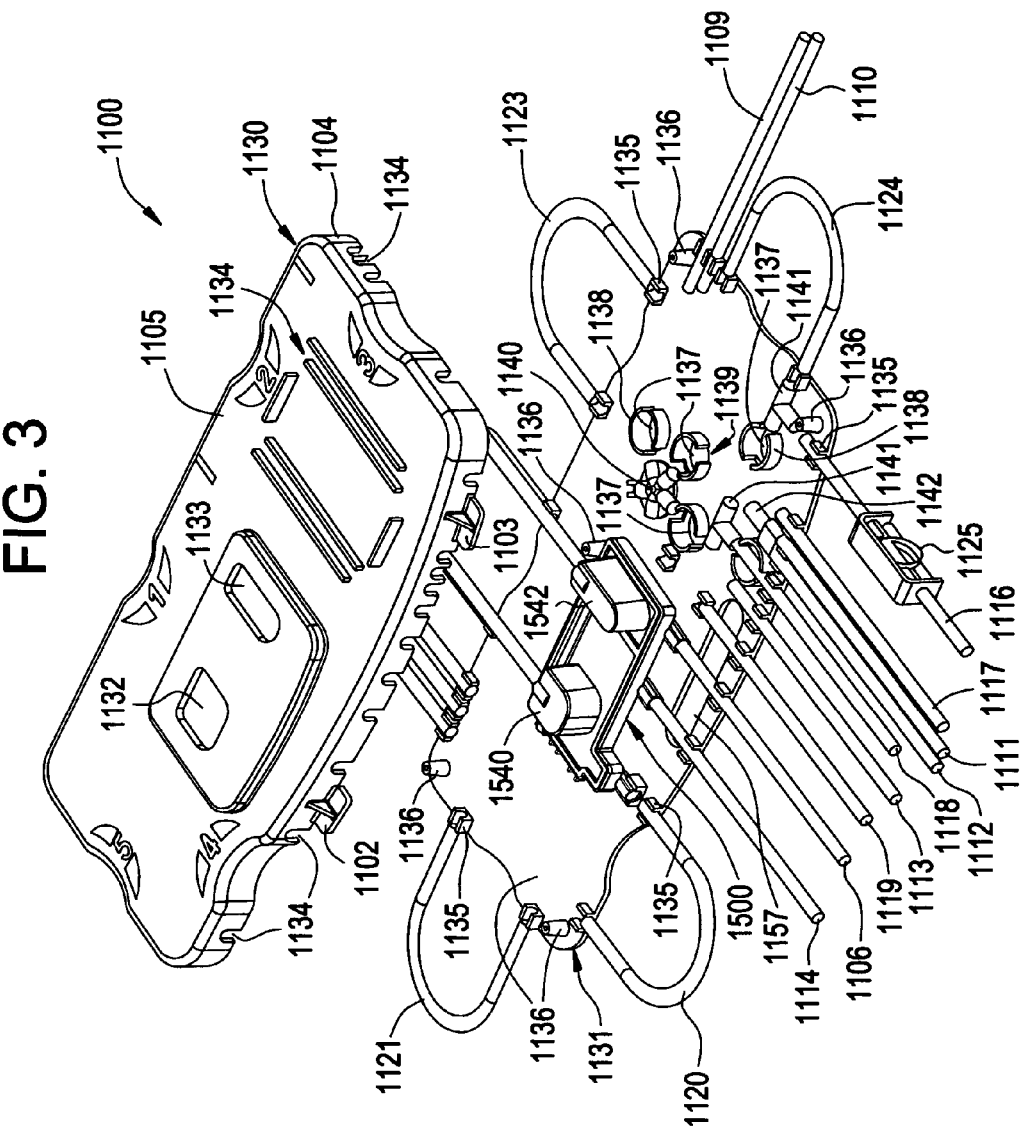
FIG. 3 is an exploded view of the cassette of FIG. 2.

Turning now to FIG. 3, cassette 1100 is shown with housing 1101 in an exploded state. For ease of illustration and description, the internal tubular circuitry within housing 1101 is not illustrated in FIG. 3. The internal tubular circuitry is illustrated in FIG. 4 and will be discussed in relation thereto. Cassette 1100 has filter assembly 1500 positioned therein and in fluid connection with inlet tube 1106, outlet tube 1114, and one end of each of pump tube loops 1120 and 1121. Filter assembly 1500 comprises vent chambers 1540 and 1542. Filter assembly 1500, and its functioning, is discussed in detail below with respect to FIGS. 6-10.

Figure 5:
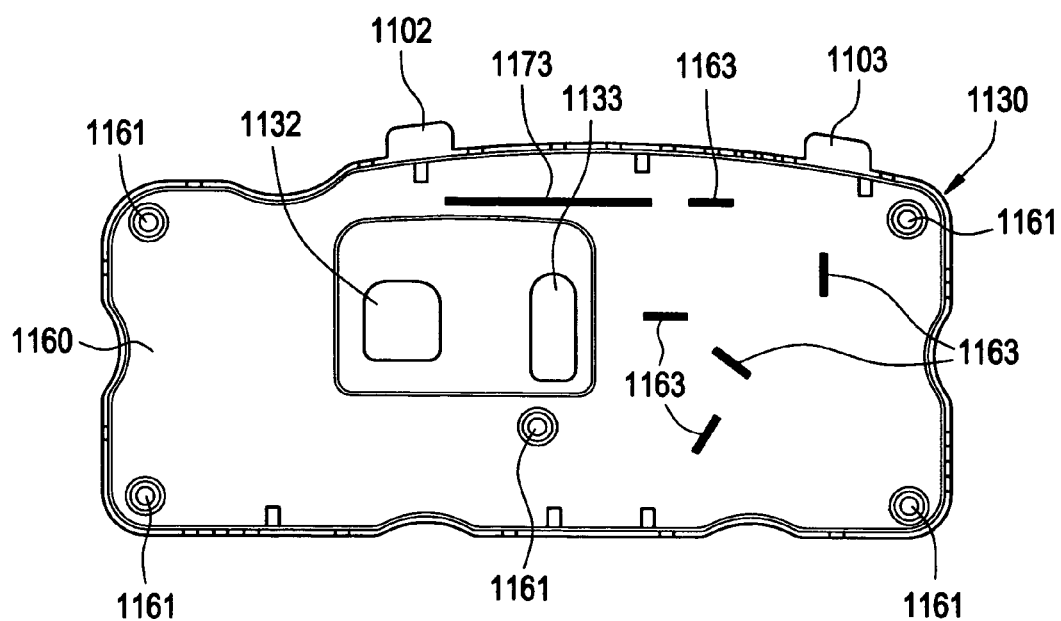
FIG. 5 is a bottom view of a cover of cassette of FIG. 2.

Housing 1101 comprises cover 1130 and base 1131. Cover 1130 has top surface 1105, a bottom surface 1160 (FIG. 5), and side wall 1104. Cover 1130 has openings 1132 and 1133 for allowing vent chambers 1540 and 1542 of filter assembly 1500 to extend therethrough. Side wall 1104 has a plurality of tube slots 1134 to allow the inlet tubes, outlet tubes, and pump loop tubes to pass into the internal space of housing 1101 for connection with the internal tubular circuitry located therein. Only a few tube slots 1134 are labeled in FIG. 3 to avoid numerical crowding. Tabs 1102 and 1103 are positioned on side wall 1104 so as not to interfere with tube slots 1134. Cover 1130 has occluder bars 1162 and 1162A extending from bottom surface 1160 (FIG. 5). Occluder bars 1162 and 1162A are preferably molded into bottom surface 1160 of cover 1130 during its formation.

Base 1131 has a plurality of U-shaped tube-holders 1135 extending upward from top surface 1136. U-shaped tube holders 1135 hold the inlet tubes, outlet tubes, pump loop tubes, filter assembly, and internal tubular circuitry in place. Only a few U-shaped holders 1135 are labeled in FIG. 3 to avoid numerical crowding. Preferably, a U-shaped holder 1135 is provided on base 1131 at each location where an inlet tube, an outlet tube, or a pump loop tube passes through a tube slot 1134 on side wall 1104. Male extrusions 1136 protrude from top surface 1136 of base 1131 for mating with corresponding female holes 1161 located on bottom surface 1160 of cover 1130 (FIG. 5). Preferably, a male protrusion 1136 is located at or near each of the four corners of base 1130 and near filter 1500. Male protrusions 1136 mate with the female holes 1161 to form a snap-fit and secure base 1131 to cover 1130.

Base 1131 further comprises a hub 1140. Hub 1140 is a five-way tube connector used to connect five tubes of the internal tubular circuitry. Preferably, three apertures 1137 are located near and surround three of the tubes leading into hub 1140. Hub 1140 acts as a centralized junction which can be used, in conjunction with compression actuators 1240-1247 (FIG. 22), to direct fluids through photopheresis kit 1000 and to and from the patient. In addition to hub 1140, appropriate tube connectors, such as T-connectors 1141 and Y-connector 1142, are used to obtain the desired flexible tubing pathways.

Figure 22:
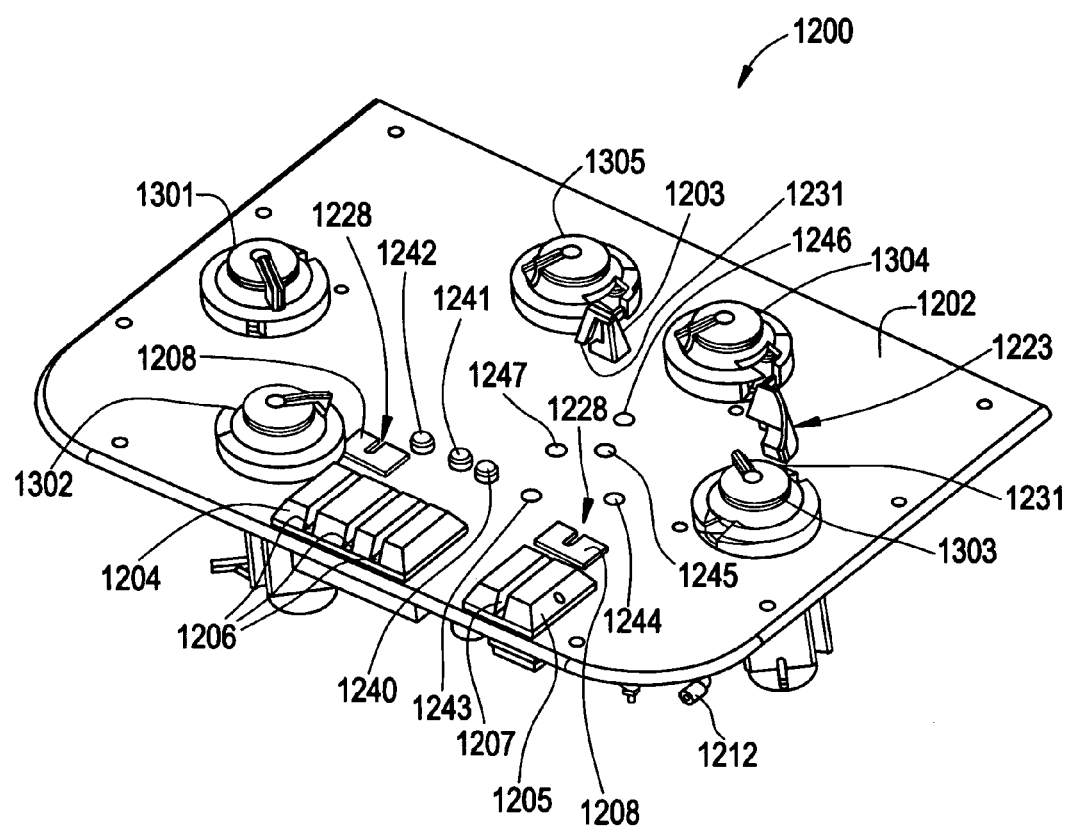
FIG. 22 is an elevated perspective view of an embodiment of the fluid flow control deck of the tower system of FIG. 17.

Five apertures 1137 are located on the floor of base 1130. Each aperture 1137 is surrounded by an aperture wall 1138 having slots 1139 for passing portions of the internal tubular circuitry therethrough. An elongated aperture 1157 is also provided on the floor of base 1131. Apertures 1137 are located on base 1131 to align with corresponding compression actuators 1243-1247 of deck 1200 (FIG. 22). Aperture 1157 is located on base 1131 to align with compression actuators 1240-1242 of deck 1200 (FIG. 22). Each aperture 1137 is sized so that a single compression actuator 1243-1247 can extend therethrough. Aperture 1157 is sized so that three compression actuators 1240-1242 can extend therethrough. Compression actuators 1240-1247 are used to close/occlude and open certain fluid passageways of the internal tubular circuitry in order to facilitate or prohibit fluid flow along a desired path. When it is desired to have a certain passageway open so that fluid can flow therethrough, the compression actuator 1240-1247 for that passageway is in a lowered position However, when it is desired to have a certain fluid passageway closed so that fluid can not flow therethrough, the appropriate compression actuator 1240-1247 is raised, extending the compression actuator 1240-1247 through aperture 1137 or 1157 and compressing a portion of the flexible tubular circuitry against bottom surface 1160 (FIG. 5) of cover 1130, thereby closing that passageway. Preferably, occluder bars 1163 and 1173 (FIG. 5) are positioned on bottom surface 1160 to align with the compression actuators 1240-1247 so that the portion of flexible tubing being occluded is compressed against occluder bar 1163 or 1173. Alternatively, the occluder bar can be omitted or located on the compression actuators themselves.

It is preferable for cassette 1100 to have a unique identifier that can communicate with and relay information to permanent tower system 2000. The unique identifier is provided to ensure that the disposable photopheresis kit is compatible with the blood drive equipment into which it is being loaded, and that the photopheresis kit is capable of running the desired treatment process. The unique identifier can also be used as a means to ensure that the disposable photopheresis kit is of a certain brand name or make. In the illustrated example, the unique identifier is embodied as data card 1195 (FIG. 2) that is inserted into data card receiving port 2001 of permanent tower system 2000 (FIG. 17). Data card 1195 has both read and write capabilities and can store data relating to the treatment therapy performed for future analysis. The unique identifier can also take on a variety of forms, including, for example, a microchip that interacts with the blood drive equipment when the kit is loaded, a bar code, or a serial number.

Cover 1130 has data card holder 1134 for holding data card 1195 (FIG. 1). Data card holder 1134 comprises four elevated ridges in a segmented rectangular shape for receiving and holding data card 1195 to cassette 1100. Data card holder 1134 holds data card 1195 in place via a snap-fit (FIG. 2).

Referring now to FIGS. 1 and 4, the internal tubular circuitry of cassette 1100 will now be discussed. At least a portion of the internal tubular circuitry is preferably made of flexible plastic tubing that can be pinched shut by the exertion of pressure without compromising the hermetic integrity of the tube. Base 1131 of cassette 1100 is illustrated in FIG. 4 so that the internal tubular circuitry can be viewed. Inlet tubes 1107 and 1108 and outlet tube 1115 are provided for coupling cassette 1100 to centrifuge bowl 10 (FIG. 1). More specifically, outlet tube 1115 is provide for delivering whole blood from cassette 1100 to centrifuge bowl 10, and inlet tubes 1107 and 1108 are respectively provide for returning a lower density blood components and higher density blood components to cassette 1100 for further routing through photopheresis kit 1000. The lower density blood components can include, for example, plasma, leukocytes, platelets, buffy coat, or any combination thereof. The higher density components can include, for example, red blood cells. Outlet tube 1117 and inlet tube 1112 fluidly couple cassette 1100 to irradiation chamber 700. More specifically, outlet tube 1117 is provided for delivering an untreated lower density blood component, for example buffy coat, to irradiation chamber 700 for exposure to photo energy, while inlet tube 1112 is provided for returning the treated lower density blood component to cassette 1100 for further routing.

Inlet tube 1111 and outlet tube 1116 couple treatment bag 50 to cassette 1100. Outlet tube 1116 is provided to deliver an untreated low density blood component, for example buffy coat, to treatment bag 50. Outlet tube 1116 has hematocrit ("HCT") sensor 1125 operably connected thereto to monitor for the introduction of a high density blood component, such as red blood cells. HCT sensor 1125 is a photo sensor assembly and is operably coupled to a controller. HCT sensor 1125 sends a detection signal to the controller when red blood cells are detected in outlet tube 1116 and the controller will take the appropriate action. Inlet tube 1111 is provided to return the untreated low density blood component from treatment bag 50 to cassette 1100 for further routing. Inlet tubes 1109 and 1110 are respectively connected to a saline and anticoagulant storage bags (not shown) via spikes 1190 and 1191 and are provided for delivering saline and an anticoagulant fluid to cassette 1100 for further routing to the patient.

Inlet/Outlet tube 1113 and outlet tube 1118 couple plasma collection bag 50 to cassette 1100. More specifically, outlet tube 1118 delivers a blood component, such as plasma, to plasma collection bag 51. Inlet/Outlet tube 1113 can be used to either deliver red blood cells to plasma collection bag 51 from cassette 1100 or return the blood component(s) that build up in plasma collection bag 51 to cassette 1100 for further routing. Inlet tube 1106 and outlet tubes 1119 and 1114 are coupled to a patient. Specifically, outlet tube 1114 is provided to return treated blood, saline, untreated blood components, treated blood components, and other fluids back to the patient. Inlet tube 1106 is provided for delivering untreated whole blood (and a predetermined amount of an anticoagulant fluid) from the patient to cassette 1100 for routing and treatment within photopheresis kit 1000. Outlet tube 1119 is specifically provided for delivering an anticoagulant fluid to inlet tube 1106. It is preferable that all tubing is disposable medical grade sterile tubing. Flexible plastic tubing is the most preferred.

Cassette 1100 has five pump tube loops 1120, 1121, 1122, 1123, and 1124 for driving blood fluids throughout cassette 1100 and photopheresis kit 1000. More specifically, pump tube loop 1121 loads into whole blood pump 1301 and respectively drives whole blood in and out of cassette 1100 via inlet tube 1106 and outlet tube 1115, passing through filter 1500 along the way. Pump loop tube 1120 loads into return pump 1302 and drives blood fluids through filter 1500 and back to the patient via outlet tube 1114. Pump loop tube 1122 loads into red blood cell pump 1305 and draws red blood cells from centrifuge bowl 10 and drives them into cassette 1100 via inlet line 1108. Pump loop tube 1123 loads into anticoagulant pump 1304 and drives an anticoagulant fluid into cassette 1100 via inlet tube 1124 and out of cassette 1100 to via outlet tube 1119, which connects with inlet tube 1106. Pump loop tube 1124 loads into recirculation pump 1303 and drives blood fluids, such as plasma, through treatment bag 50 and irradiation chamber 700 from cassette 1100.

Each of peristaltic pumps 1301-1305 are activated when necessary to perform the photopheresis treatment therapy according to an embodiment of the method of the present invention which is described below in relation to FIGS. 26-27. Peristaltic pumps 1301-1305 can be operated one at a time or in any combination. The pumps 1301-1305 work in conjunction with compression actuators 1240-1247 to direct fluids through desired pathways of photopheresis kit 1000. Apertures 1137 and 1157 are strategically located on base 1131 along the internal tubular circuitry to facilitate proper routing. Through the use of compression actuators 1240-1247, the fluids can be directed along any pathway or combination thereof.

The Filter Assembly

Figure 6:
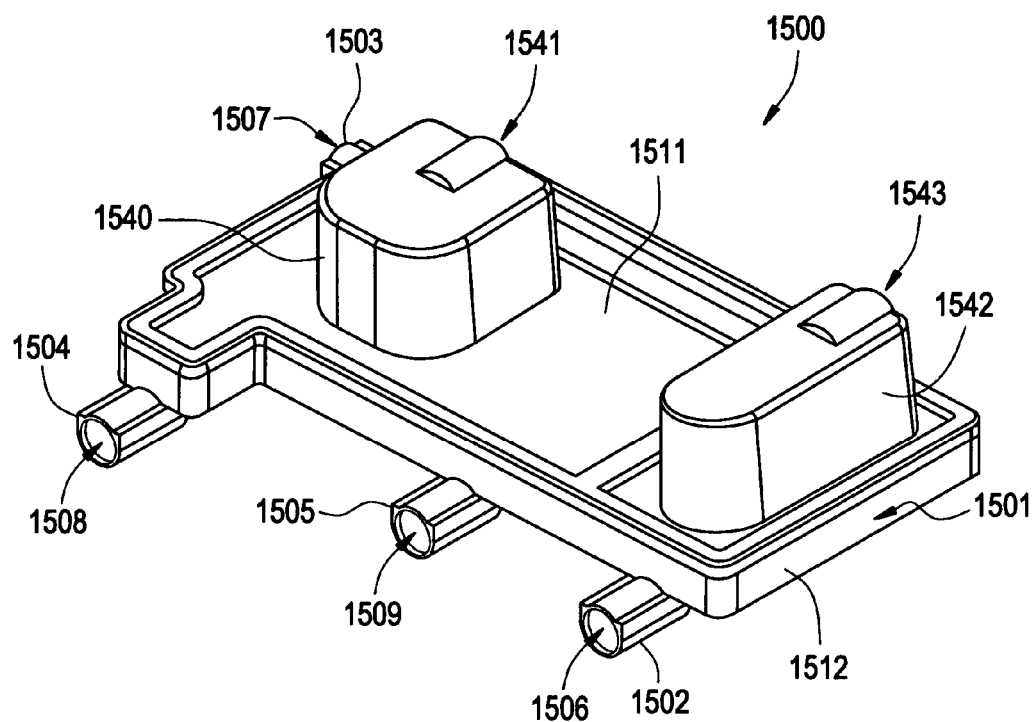
FIG. 6 is an elevated perspective view of an embodiment of a filter assembly.
Figure 7:
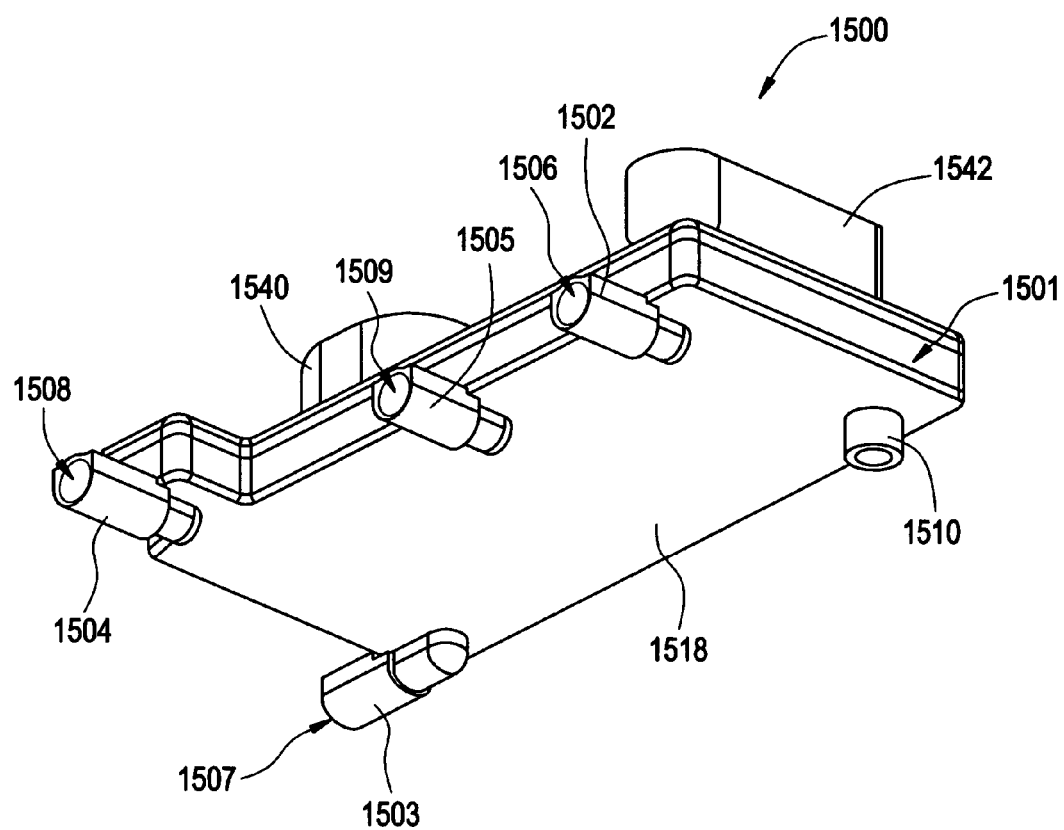
FIG. 7 is bottom perspective view of the filter assembly of FIG. 6.

Filter 1500, which is located within cassette 1100 as described above, is illustrated in detail in FIGS. 6-10. Referring first to FIGS. 6 and 7, filter 1500 is illustrated fully assembled. Filter 1500 comprises a filter housing 1501. Filter housing 1501 is preferably constructed of a transparent or translucent medical grade plastic. However, the invention is not so limited and filter housing 1501 can be constructed of any material that will not contaminate blood or other fluids that are flowing therethrough.

Filter housing 1501 has four fluid connection ports extruding therefrom, namely whole blood inlet port 1502, whole blood outlet port 1503, treated fluid inlet port 1504, and treated fluid outlet port 1505. Ports 1502-1505 are standard medical tubing connection ports that allow medical tubing to be fluidly connected thereto. Ports 1502-1505 respectively contain openings 1506, 1507, 1508 and 1509. Openings 1506, 1507, 1508 and 1509 extend through ports 1502, 1503, 1504 and 1505, forming fluid passageways into filter housing 1501 at the desired locations.

Ports 1502, 1503, 1504 and 1505 are also used to secure filter 1500 within cassette 1100. In doing so, ports 1502, 1503, 1504 and 1505 can engage U-shaped fasteners 1135 of cassette 1100 (FIG. 3). Filter housing 1501 also has a protrusion 1510 extending the bottom surface of housing floor 1518. Protrusion 1510 fits into a guide hole of base 1131 of cassette 1100 (FIG. 3).

Figure 8:
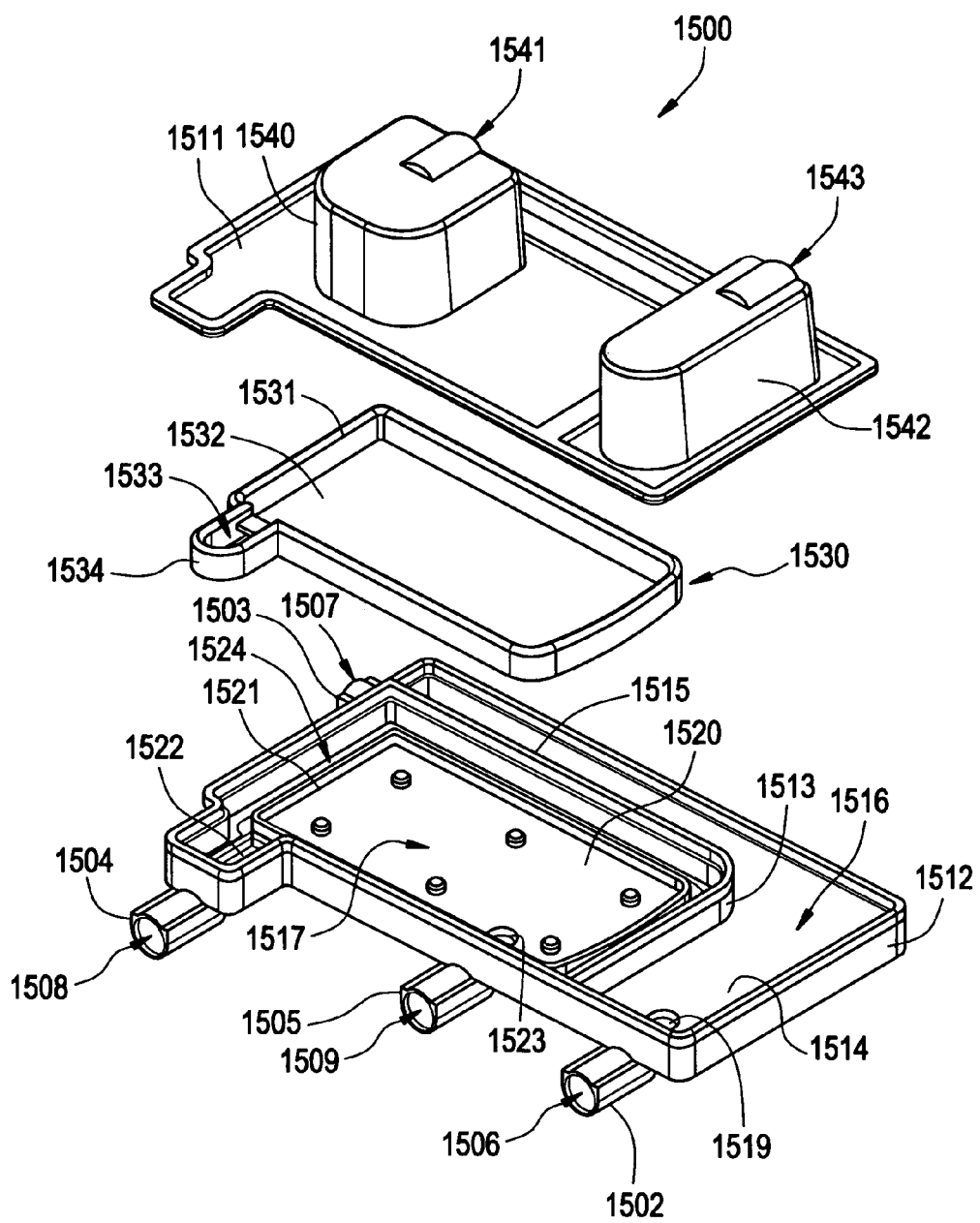
FIG. 8 is an exploded view of the filter assembly of FIG. 6.

Referring now to FIG. 8, filter 1500 is illustrated in an exploded state. Filter housing 1501 is a two-piece assembly comprising roof 1511 and base 1512. Roof 1511 is connected to base 1512 by any means known in the art, such as ultrasonic welding, heat welding, applying an adhesive, or by designing roof 1511 and base 1512 so that a tight fit results between the two. While filter housing 1501 is illustrated as a two-piece assembly, filter housing 1501 can be either a single piece structure or a multi-piece assembly.

Base 1512 has chamber separation wall 1513 extending upward from a top surface of housing floor 1518 (FIG. 7). When base 1512 and roof 1511 are assembled, top surface 1515 of chamber separation wall 1513 contacts the bottom surface of roof 1511, forming two chambers within the filter housing, whole blood chamber 1516 and filter chamber 1517. Fluid can not directly pass between whole blood chamber 1516 and filter chamber 1517.

Whole blood chamber 1516 is a substantially L-shaped chamber having floor 1514. Whole blood chamber 1516 has a whole blood inlet hole 1519 and a whole blood outlet hole (not illustrated) in floor 1514. Whole blood inlet hole 1519 and the whole blood outlet hole are located at or near the ends of the substantially L-shaped whole blood chamber 1516. Whole blood inlet hole 1519 forms a passageway with opening 1506 of inlet port 1502 so that a fluid can flow into whole blood chamber 1516. Similarly, the whole blood outlet hole (not illustrated) forms a passageway with opening 1507 of outlet port 1503 so that fluid can flow out of whole blood chamber 1516.

Filter chamber 1517 has floor 1520. Floor 1520 has elevated ridge 1521 extending upward therefrom. Elevated ridge 1521 is rectangular and forms a perimeter. While elevated ridge 1521 is rectangular in the illustrated embodiment, elevated ridge 1521 can be any shape so long as it forms an enclosed perimeter. The height of elevated ridge 1521 is less than the height of chamber separation wall 1513. As such, when roof 1511 and base 1512 are assembled, space exists between the top of elevated ridge 1521 and the bottom surface of roof 1511. Elevated ridge 1521 and chamber separation wall 1513 form a trench 1524 there between.

In order to facilitate fluid flow through filter chamber 1517, floor 1520 of filter chamber 1517 has treated fluid inlet hole 1522 and treated fluid outlet hole 1523. Treated fluid inlet hole 1522 is located exterior of the perimeter formed by elevated ridge 1521 and forms a passageway with opening 1508 of inlet port 1504 so that a fluid can flow into filter chamber 1517 from outside filter housing 1501. Treated fluid outlet hole 1523 is located interior of the perimeter formed by elevated ridge 1521 and forms a passageway with opening 1509 of outlet port 1505 so that a fluid can flow out of filter chamber 1517.

Filter 1500 further comprises filter element 1530. Filter element 1530 comprises frame 1531 having filter media 1532 positioned therein. Frame 1531 has a neck 1534 that forms a filter inlet hole 1533. Filter element 1530 is positioned in filter chamber 1517 so that frame 1531 fits into trench 1524 and neck 1534 surrounds treated blood inlet hole 1522. Filter inlet hole 1533 is aligned with treated fluid inlet hole 1522 so that incoming fluid can freely flow through holes 1522 and 1533 into filter chamber 1517. Frame 1531 of filter element 1530 forms a hermetic fit with elevated ridge 1521. All fluid that enters filter chamber 1517 through holes 1522 and 1533 must pass through filter media 1532 in order to exit filter chamber 1517 via treated fluid outlet hole 1523. Filter media 1532 preferably has a pore size of approximately 200 microns. Filter media 1532 can be formed of woven mesh, such as woven polyester.

Figure 9:
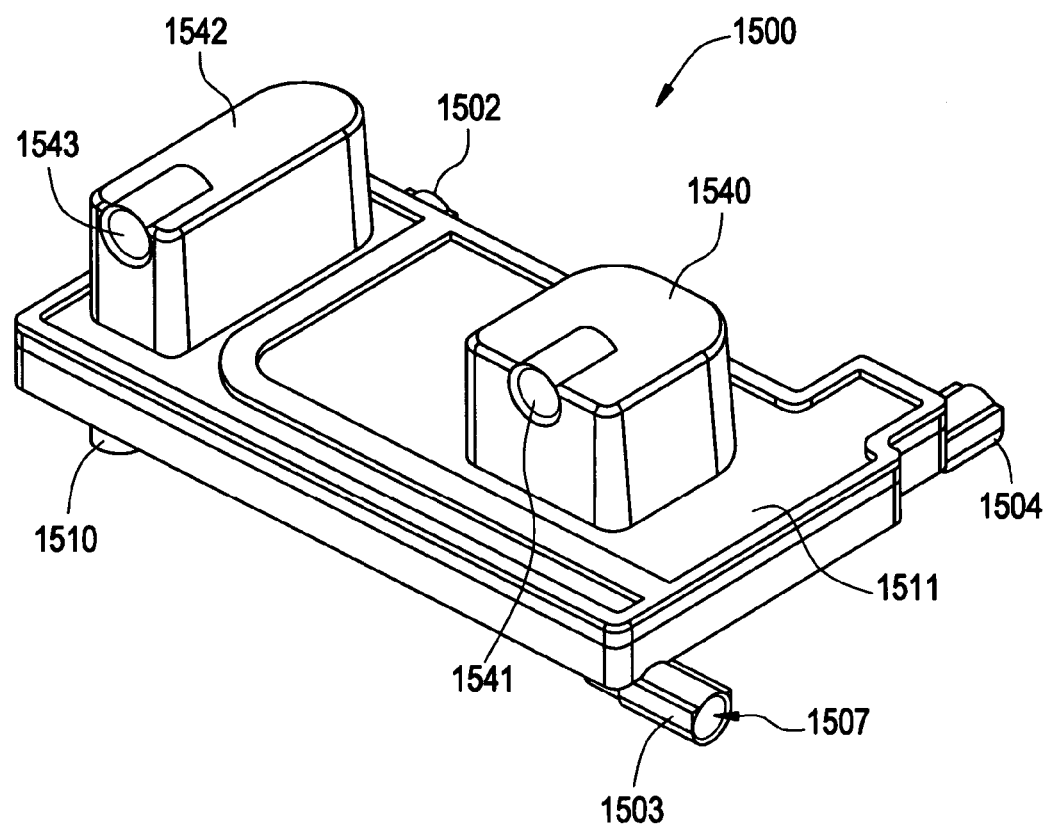
FIG. 9 is a rear perspective view of the filter assembly of FIG. 6.

Filter chamber 1517 further comprises filter vent chamber 1540 within roof 1511. Filter vent chamber 1540 has gas vent 1541 in the form of a hole (FIG. 9). Because gas vent 1541 opens into filter vent chamber 1540 which in turn opens into filter chamber 1517, gases that build-up within filter chamber 1517 can escape through gas vent 1541. Similarly, whole blood chamber 1516 comprises blood vent chamber 1542 within roof 1511. Blood vent chamber 1541 has gas vent 1543 in the form of a hole. Because gas vent 1543 opens into blood vent chamber 1542 which in turn opens into whole blood chamber 1517, gases that build-up in whole blood chamber 1516 can escape via gas vent 1543.

FIG. 10 is a top view of filter 1500 having pressure sensors 1550 and 1551 connected to gas vents 1541 and 1543. Pressure sensors 1550 and 1551 are preferably pressure transducers. Pressure sensor 1550 is connected to gas vent 1541 via vent tubing 1552. Vent tubing 1552 fits into gas vent 1541 so as to form a tight fit and seal. Because gas vent 1541 opens into filter vent chamber 1540 which in turn opens into filter chamber 1517, the pressure in vent tubing 1552 is the same as in filter chamber 1517. By measuring the pressure in vent tubing 1552, pressure sensor 1550 also measures the pressure within filter chamber 1517. Similarly, pressure sensor 1551 is connected to gas vent 1543 via vent tubing 1553. Vent tubing 1553 fits into gas vent 1543 so as to form a tight fit and seal and pressure sensor 1551 measures the pressure within whole blood chamber 1516. Filter vent chamber 1540 and blood vent chamber 1542 extend through openings 1132 and 1133 of cassette 1100 when filter 1500 is positioned therein (FIG. 2). This allows the pressure within chambers 1516 and 1517 to be monitored while still protecting filter chamber 1500 and the fluid connections thereto.

Pressure sensors 1550 and 1551 are coupled to controller 1554, which is a properly programmed processor. Controller 1554 can be a main processor used to drive the entire system or can be a separate processor coupled to a main processor. Pressure sensors 1550 and 1551 produce electrical output signals representative of the pressure readings within chambers 1517 and 1516 respectively. Controller 1554 receives on a frequent or continuous basis data representing the pressure within chambers 1516 and 1517. Controller 1554 is programmed with values representing desired pressures within chambers 1516 and 1517. Controller 1554 continuously analyzes the pressure data it receives from pressure sensors 1550 and 1551 to determine whether the pressure readings are within a predetermined range from the desired pressure for chambers 1517 and 1516. Controller 1554 is also coupled to whole blood pump 1301 and return pump 1302. In response to the pressure data received from pressure sensors 1551 and 1550, controller 1554 is programmed to control the speed of whole blood pump 1301 and return pump 1302, thereby adjusting the flow rates through the pumps 1301 and 1301. Adjusting these flow rates in turn adjust the pressure within whole blood chambers 1516 and filter chamber 1517 respectively. It is in this way that the pressure within the lines drawing and returning blood to and from the patient is maintained at acceptable levels.

The functioning of filter 1500 during a photopheresis therapy session will now be discussed in relation to FIGS. 1, 6, and 10. While the functioning of filter 1500 will be described in detail with respect to drawing whole blood from a patient and returning a component of said whole blood back into the patient after it is treated, the invention is not so limited. Filter 1500 can be used in connection with almost any fluid, including red blood cells, white blood cells, buffy coat, plasma, or a combination thereof.

Whole blood pump 1601 draws whole blood from a patient who is connected to photopheresis kit 1000 via a needle connected to port 1193. The rotational speed of whole blood pump is set so that the pressure of the line drawing the whole blood from the patient is at an acceptable level. Upon being drawn from the patient, the whole blood passes into cassette 1100 via inlet tube 1106. Inlet tube 1106 is fluidly connected to inlet port 1502 of filter 1500. The whole blood passes through opening 1506 of inlet port 1502 and into L-shaped whole blood chamber 1516. The whole blood enters chamber 1516 through inlet hole 1519 which is located on floor 1514. As more whole blood enters chamber 1516, the whole blood spills along floor 1514 until it reaches the whole blood outlet hole (not illustrated) at the other end of L-shaped whole blood chamber 1516. As discussed above, the whole blood outlet whole forms a passageway with opening 1507 of outlet port 1503. The whole blood that is within chamber 1516 flows across floor 1514, through the whole blood outlet hole, into outlet port 1503, and out of filter 1500 through opening 1507.

As the whole blood passes through whole blood chamber 1516, gases that are trapped in the whole blood escape. These gases collect in blood vent chamber 1542 and then escape via gas vent 1543. Pressure sensor 1551 continuously monitors the pressure within blood chamber 1516 through vent tube 1553 and transmits corresponding pressure data to controller 1554. Controller 1554 analyzes the received pressure data and if necessary adjusts the speed of whole blood pump 1301, thereby adjusting the flow rate and pressure within chamber 1516 and inlet tube 1106. Controller 1554 adjust the pump speed to ensure that the pressure is within the desired pressure range.

The whole blood then exits filter 1500 through outlet port 1503 and passes out of cassette 1100 via outlet tube 1115. The whole blood is then separated into components and/or treated as described in detail below. Before being returned to the patient, this treated fluid (i.e. treated blood or blood components) must be filtered. Untreated fluids such as red blood cells also must be filtered and will subjected to the below filtering process. The treated fluid is fed into filter chamber 1517 through opening 1508 of inlet port 1504. Inlet port 1504 is fluidly connected to pump loop tube 1120. The treated fluid enters filter chamber 1517 through inlet hole 1522 and passes through filter inlet hole 1533 of filter element 1530. The treated fluid fills filter chamber 1517 until it spills over frame 1531 of filter element 1530, which is secured to elevated ridge 1521. The treated fluid passes through filter media 1532. Filter media 1532 removes contaminants and other undesired materials from the treated fluid while at the same facilitating the release of trapped gases from the treated fluid. The treated fluid that passes through filter media 1532 gathers on floor 1520 of filter chamber 1517 within the perimeter formed by elevated ridge 1521. This treated fluid then passes into treated fluid outlet hole 1523 and out of filter 1500 through opening 1506 of outlet port 1502. The treated fluid is then returned to the patient via outlet tube 1114, which is fluidly connected to outlet port 1502. The treated fluid is driven through filter chamber 1517 and outlet tube 1114 by return pump 1302.

Gases that are trapped in the treated fluid escape and collect in filter vent chamber 1540 as the treated fluid flows through filter chamber 1517. These gases then escape filter 1500 via gas vent 1541. Pressure sensor 1550 continuously monitors the pressure within filter chamber 1517 through vent tube 1552 and transmits corresponding pressure data to controller 1554. Controller 1554 analyzes the received pressure data and compares it to the desired pressure value and range. If necessary, controller 1554 adjusts the speed of return pump 1302, thereby adjusting the flow rate and pressure within chamber 1517 and outlet tube 1114.

Cassette 2 for Controlling Fluid Flow

Figure 58:
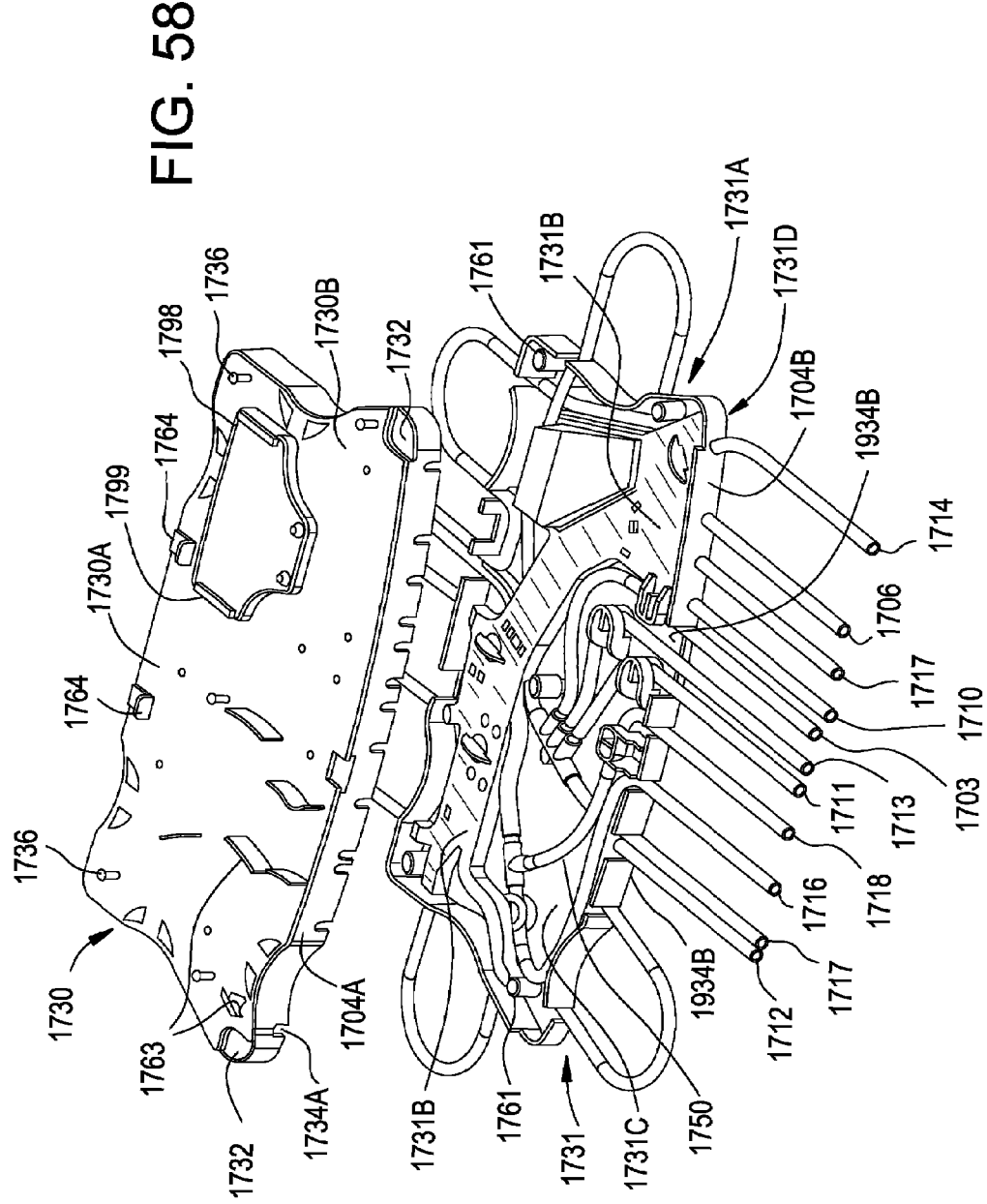
FIG. 58 shows an exploded view of the cassette of FIG. 56.
Figure 61:
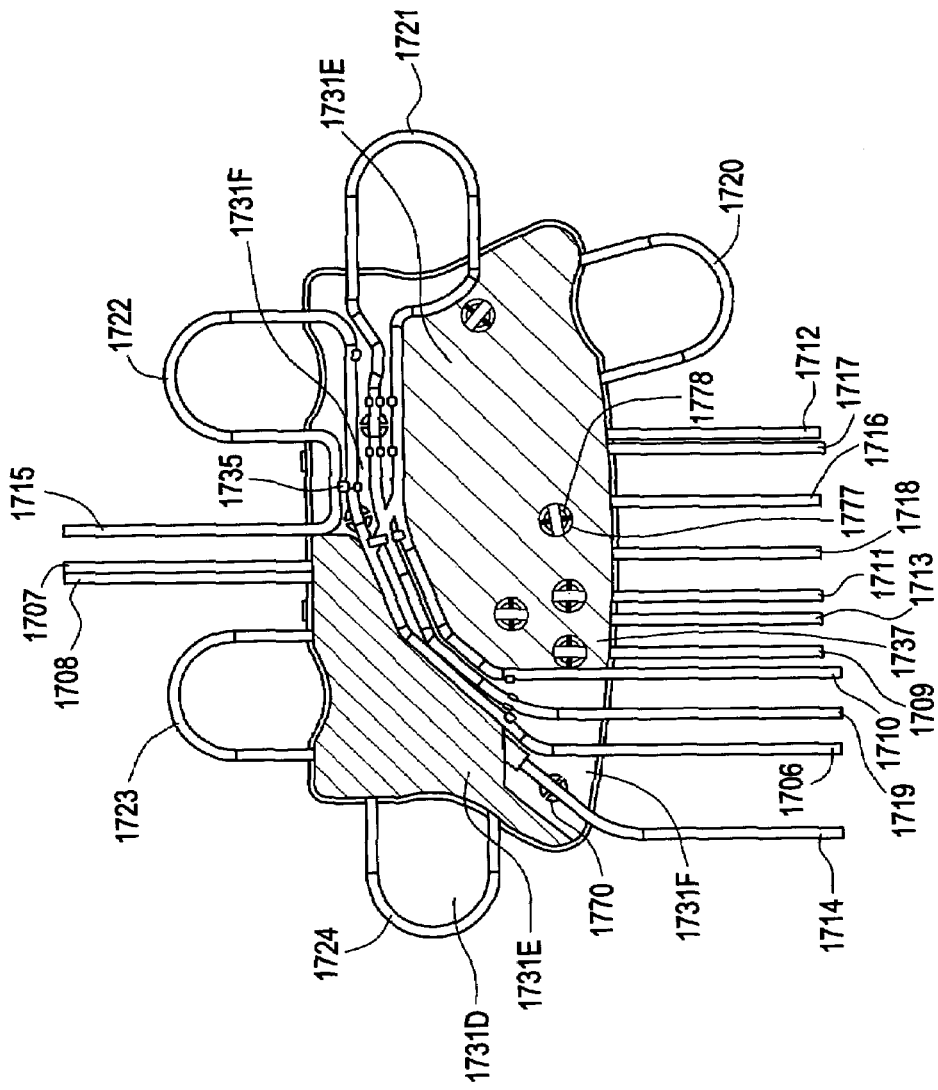
FIG. 61 is a bottom view of the cassette of FIG. 56 showing external tubular circuitry outside the housing of the cassette.

Cassette 1700 functions both as a tube organizer and fluid flow router and is preferably constructed of a transparent or translucent medical grade plastic or any material that will not contaminate blood or other fluids that are flowing therethrough. The inside or interior of cassette 1700 is the space inside housing 1901 formed by the joining of the cover 1730 and base 1731 (FIG. 58). Parts of inlet tubings and outlet tubings are located both inside of cassette 1700 and on the bottom surface of the base outside of cassette 1700 (FIG. 61). An advantage of having tubings located inside and on the bottom surface of base 1731 outside of cassette 1700 is the reduction of the number of crisscrossing of tubings inside cassette 1700 which in turn facilitates the manufacturing of the cassette. In Cassette 1700 tubings located on the bottom surface of the base outside of cassette 1700 are for purposes including for incoming whole blood and for mixing AC or priming fluid, e.g. saline, with whole blood and for returning blood components or priming fluid back to a subject. Tubings inside housing 1901 are for purposes including the pumping process associated with peristaltic pumps, collecting buffy coat from bowl 10, routing buffy coat, plasma to and from irradiation chamber 1910, and filtering blood components.

FIGS. 57 and 58 show a top view and an exploded view of a disposable cassette 1700 for valving, pumping, and controlling the movement of blood fluids during a photopheresis treatment session. Cover 1730 and base 1731 are preferably made of hard plastic, but can be made of any suitably rigid material. Housing 1901 has side wall 1704 formed by the overlapping of sidewall 1704A of cover 1730 and sidewall 1704B of base 1731.

Cover 1730 has a top surface 1730A, a bottom surface 1730D, and side wall 1704A having a plurality of tube slots 1734A to allow the inlet tubes, outlet tubes, and pump loop tubes to pass into the internal space of housing 1901 for connection with the internal tubular circuitry located therein. Top surface 1730A of cover 1730 has data card holder 1796 which is slightly elevated above surface 1730A and comprises an elevated ridge 1798, two side wings 1799 for receiving and holding data card 1795 to cassette 1700 by a snap-fit (FIG. 57). Top surface 1730A also has indentations 1732 and tabs 1764 attached to sidewall 1704A for receiving catches 1733 and 1765 located on deck 3200 respectively. For securing the cover to the base by a snap-fit, a plurality of male extrusions 1736 protrude from bottom surface 1730B of cover 1730 for mating with corresponding female holes 1761 located on top surface 1731C of base 1731 (FIG. 58). Preferably, a male protrusion 1736 is located at or near the center and each of the four corners of cover 1730. Extending perpendicular from the bottom surface 1730B of cover 1730 are vertical tabs 1763 that keeps tubings in raceways 1750 on top surface of base 1731 or keep tubings and connectors in appropriate locations. Vertical tabs 1763, having a height less than that of side wall 1704, may be curved or straight or have a T-shape for securing T-connectors 1741 on top surface of base 1731.

Base 1731 has a top surface 1731A, a bottom surface 1731D (FIG. 58), and side wall 1704B having a plurality of wall opening or tube slot 1934B. When cassette 1700 is fully assembled, the overlapping of sidewall 1704A of cover 1730 and sidewall 1704B of base 1731 forms sidewall 1704 of cassette 1700 having a plurality of opening 1734 to allow for pump loop tubes, and fluid inlet and outlet tubes to pass inside housing 1901 of cassette 1700. Top surface 1731A of base 1731 comprises two levels, an upper level 1731B and a lower level 1731C. On lower lever 1731C are a plurality of raceways 1750 formed by vertical walls 1751 extending perpendicularly from surface 1731C to secure tubings inside housing 1901. The edge 1731G joining upper level 1731B and lower level 1731C may form part of a raceway. In addition to securring tubings in place, raceway 1750 may also be adapted to secure T-connectors in place by having appropriate opening for one branch of the T-connector to pass through. A tubing inside housing 1901 may also crisscross another tubing or be situated outside of a raceway to exit out of the cassette housing or to connect to another tubing or connector.

Bottom surface 1731D of base 1731 also comprises two levels, an upper level 1731E and a lower level 1731F (FIG. 61). The raceways 1750 for securing tubings in place on bottom surface 1731D are located on lower level 1731F and extend perpendicularly therefrom. The edge joining upper level 1731E and lower level 1731F may also form part of a raceway. Tube-holders 1735 extending upward from bottom surface 1731D act in conjunction with raceways 1750 to hold tubings outside of housing 1901 in place. Opening or tube slot 1934B of sidewall 1704B allows for pump loop tubes, and fluid inlet and outlet tubes extend onto bottom surface 1731F of base 1731 and be secured in raceway 1750.

Base 1731 has two kinds of occluder bars for tubings interior and exterior of cassette 1700. Occluder bar 1777 is designed for tubings interior of cassette 1700 and is located above lower level 1730C. Occlusion bar 1777 is supported by anchor 1779 located on upper level 1730B or lower level 1731C. A plurality of round apertures 1778 are located directly below occluder bar 1777 on lower level 1731C of base 1731 to align with corresponding compression actuators (not shown) similar to actuators 1240-1247 for deck 1200. Each aperture 1778 is sized so that a single compression actuator can extend therethrough. Compression actuators are used to close/occlude and open certain fluid passageways of the internal tubular circuitry by pressing tubings against occluder bar 1777 in order to facilitate or prohibit fluid flow along a desired path. Space exists between occluder bar 1777 and lower level 1731C to allow internal tubings to slide in between.

In addition to occluder bar 1777 for controlling movement of fluids inside tubings inside housing 1901, base 1731 also has occluder bar 1770 on lower level 1731F (FIG. 60, 61) for controlling fluid movements of fluids inside tubings located on the bottom surface of cassette 1700 outside of housing 1901. Occluder bar 1770 may be formed by a straight edge of a semi-circular tab or clip 1776 that divides a round opening 1788 into two parts. Having a thin edge allows occluder bar 1770 to efficiently prevent fluid flowing inside a tubing when an actuator presses the tubing against the occluder bar. Compression actuators are used to close/occlude and open certain fluid passageways of external tubular circuitry by pressing tubings against occluder bar 1770.

Figure 59:
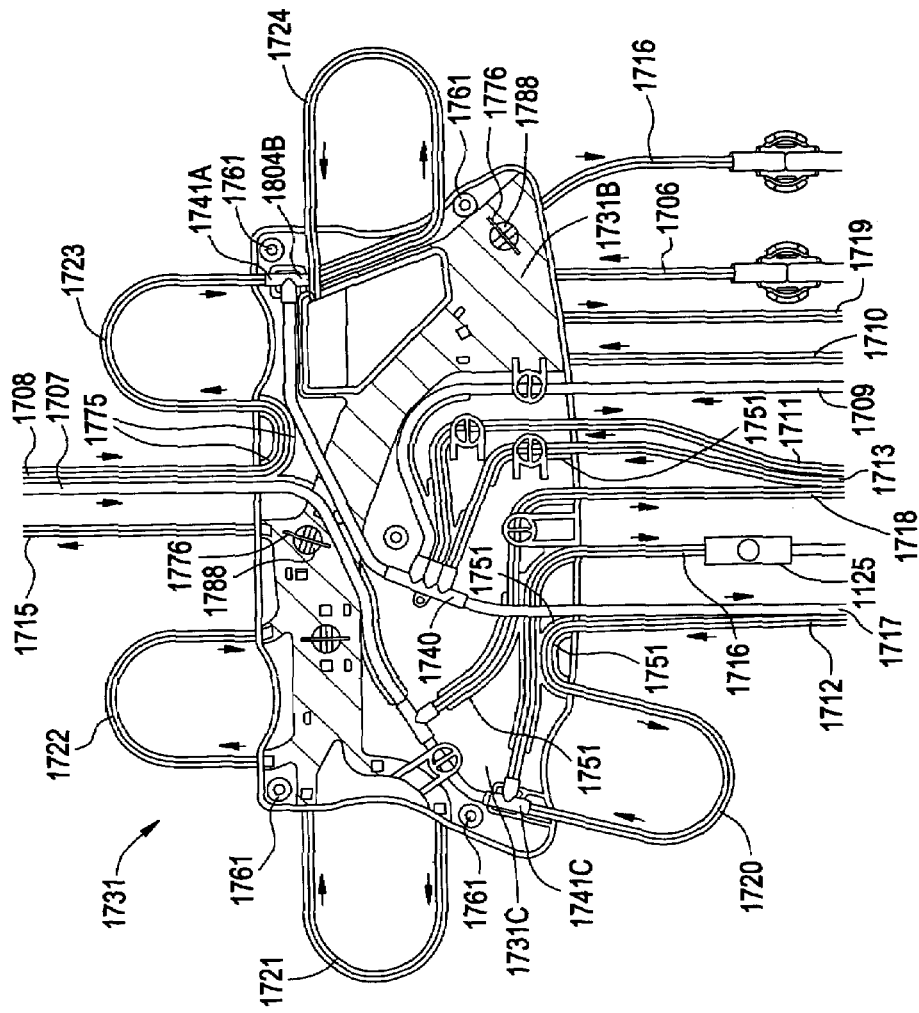
FIG. 59 shows a top view of the cassette of FIG. 56 with the cover removed and showing internal tubular circuitry inside the housing of the cassette.

Cassette 1700 has fluid inlet tubes 1706, 1707, 1708, 1709, 1710, 1711, and 1712 for receiving fluids into cassette 1700, fluid outlet tubes 1714, 1715, 1716, 1717, 1718, and 1719 for expelling fluids from cassette 1700, and fluid inlet/outlet tube 1713 that can be used for both introducing and expelling fluids into and out of cassette 1700 (FIG. 59). These fluid input and output tubes fluidly couple cassette 1700 to a patient being treated, as well as the various devices of photopheresis kit 1900, such as centrifuge bowl 10, irradiation chamber 1910, dual chamber bag 1725 and bags containing saline, anticoagulation fluid to form a closed-loop extracorporeal fluid circuit. This process is described in FIG. 26 and in a schematic shown in FIG. 27, except that the plasma bag and the treatment bag (TX bag) are combined in a dual chamber bag for photopheresis kit 1900. Multitube connector such as a five-tube connector 1740, a four-tube connector, or appropriate T-connectors 1741 and valving means, such as occluder bars and actuators are used to obtain the desired flexible tubing pathways in cassette 1700 and to direct fluids through photopheresis kit 1900 and to and from the patient.

In one embodiment of the present invention, the circuitry of fluid inlet/outlet tubes, and pump tube loops are as follows. Fluid inlet tubes 1706 and 1710 and outlet tubes 1719, 1714, and 1715 are located outside of housing 1901 and secured in part on lower level 1731F of base 1731 by raceway 1750. Anticoagulant inlet tube 1710 has fluid communication with anticoagulant outlet tube 1719 on the bottom surface 1731F of base 1731 of cassette 1700 through pump tube loop 1721 which extends on the bottom surface of the base through wall opening 1734. Blood from a donor or patient comes through inlet tube 1706 that has fluid communication with outlet tube 1715 to the bowl through pump tube loop 1722 which extends on the bottom surface of the base through wall opening 1734. Outlet tube 1714 also goes through wall opening 1734 of cassette 1700 before returning blood components back to a patient or donor. Fluid inlet tubes 1709, 1711, 1713, 1712 and fluid outlet tubes 1718, 1716, 1717 are located inside housing 1901 of cassette 1700. Saline inlet tube 1709 enters cassette 1700 through wall opening 1734 and has fluid communication with plasma inlet tube 1713, treatment chamber inlet tube 1711, T-connector 1741A, and irradiation chamber outlet tube 1717 by a five-way tube connector 1740. The five-way tube connector 1740 is in fluid communication with a three way or T-connector 1741A that is in fluid communication with red blood cell pump tube loop 1723 and return pump tube loop 1724. Return pump tube loop 1724 for returning blood or blood components to a patient or donor carries the blood to a filter before the fluid exits the cassette via outlet tube 1714. The red blood cell pump tube loop 1723 has fluid communication with inlet tube 1708 from bowl 10. Plasma and/or buffy coat entering cassette 1700 via inlet tube 1707 from bowl 10 has fluid communication with plasma outlet tube 1718 through a T-connector 1741B. Pump tube loop 1720 for circulation of blood from the treatment chamber of the dual chamber bag to the irradiation chamber has fluid communication with inlet tube 1712 from the irradiation chamber and outlet tube 1716 to treatment chamber bag and inlet line 1707 from bowl 10.

In another embodiment of the present invention, the circuitry of fluid inlet/outlet tubes and pump tube loops are as described above with the following differences. Outlet tube 1717 is removed from the five-way connector 1740 that is replaced by a four-way connector 1742. The four-way connector 1742 directly connects saline inlet tube 1709, inlet tube 1713, treatment chamber inlet tube 1711, and a flexible tubing connecting to the T-connector 1741A. In the new four-way connector 1742, the formerly "outlet tube 1717" is now connected to and in fluid communication with inlet tube 1711 by a T-connector outside of housing 1901 of cassette 1700 (FIG. 59A). In a treatment cycle, fluid flowing to irradiation chamber 1910 flows through outlet tube 1716 to the treatment chamber of dual chamber bag 1840 and exits the treatment chamber by inlet tube 1711. However, instead of flowing into cassette 1700, the fluid is directed to the formerly "outlet tube 1717" to the irradiation chamber by the T-connector 1741D. After flowing into the irradiation chamber, the fluid then exits through inlet tube 1712 and back to the cassette. Inside housing 1901, the fluid is pumped through tube loop 1720 and is directed to outlet tube 1716 to complete the cycle.

Figure 67:
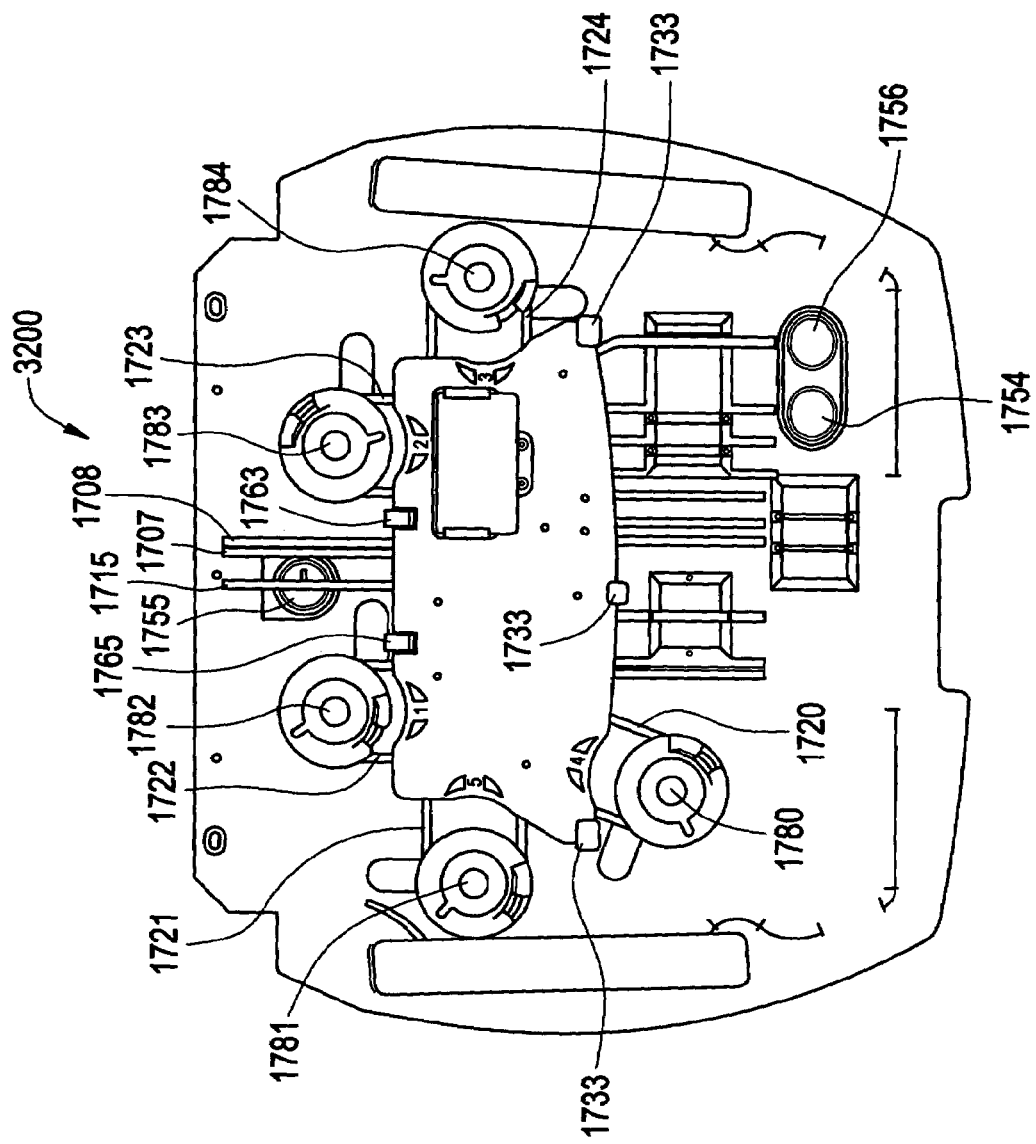
FIG. 67 is a top view of the control deck of FIG. 66 with the cassette of FIG. 56 loaded thereon.

Pump tube loops 1720, 1721, 1722, 1723, and 1724, protrude from side wall 1704 of cassette 1700, are provided for facilitating the circulation of fluids through out photopheresis kit 1900 during therapy. Side wall 1704 has openings for tube loops extending inside cassette 1700 as well as openings for tube loops extending onto the bottom surface 1731F of base 1731 of cassette 1700. More specifically, when cassette 1700 is secured to deck 3200 for operation, each one of said pump tube loops 1720, 1721, 1722, 1723, and 1724 are loaded into a corresponding peristaltic pump 1780, 1781, 1782, 1783, and 1784 (FIG. 67). The operations of peristaltic pumps 1780, 1781, 1782, 1783, and 1784 are similar to previously described peristaltic pumps 1303, 1304, 1301, 1305, and 1302 respectively. Peristaltic pumps 1780, 1781, 1782, 1783, and 1784 drive fluid through the respective pump tube loops 1720, 1721, 1722, 1723, and 1724 in a predetermined direction, thereby driving fluid through photopheresis kit 1900 (FIG. 56) as necessary.

More specifically, pump tube loop 1722 loads into whole blood pump 1782 and respectively drives whole blood in and out of cassette 1700 via inlet tube 1706 and outlet tube 1715. Pump loop tube 1724 loads into return pump 1784 and drives blood fluids through filter 1800 and back to the patient via outlet tube 1714. Pump loop tube 1723 loads into red blood cell pump 1783 and draws red blood cells from centrifuge bowl 10 and drives them into cassette 1700 via inlet line 1708. Pump loop tube 1721 loads into anticoagulant pump 1781 and drives an anticoagulant fluid into cassette 1700 via inlet tube 1710 and out of cassette 1700 to via outlet tube 1719, which connects with inlet tube 1706 through multiport connector 1792A. Pump loop tube 1720 loads into recirculation pump 1780 and drives blood fluids, such as plasma, through treatment chamber 1841 of dual chamber bag 1840 and irradiation chamber 1910 from cassette 1700.

Each of peristaltic pumps 1780-1784 is activated when necessary to perform the photopheresis treatment therapy. Peristaltic pumps 1780-1784 can be operated one at a time or in any combination. The pumps 1780-1784 work in conjunction with compression actuators (not shown) to direct fluids through any desired pathways or combination thereof of photopheresis kit 1900. An embodiment of the method of the present invention is similarly described in relation to FIGS. 26 and 27, in which the whole blood pump is 1782, the anticoagulant pump is 1781, the red blood cell pump is 1783, the recirculation pump is 1780, the return pump is 1784, the plasma chamber of dual chamber bag is 1851, the treatment chamber of dual chamber bag (TX) is 1841, the irradiation plate is 1910, and the filter is 1800.

Referring now to FIGS. 56, 59, 61, and 67 the internal tubular circuitry of cassette 1700 will now be discussed. At least a portion of the internal tubular circuitry is preferably made of flexible plastic tubing that can be pinched shut by the exertion of pressure without compromising the hermetic integrity of the tube. Inlet tubes 1707 and 1708 and outlet tube 1715 are provided for coupling cassette 1700 to centrifuge bowl 10 (FIG. 56). More specifically, outlet tube 1715 is provide for delivering whole blood from cassette 1700 to centrifuge bowl 10, and inlet tubes 1707 and 1708 are respectively provide for returning a lower density blood components and higher density blood components to cassette 1700 for further routing through photopheresis kit 1900. The lower density blood components can include, for example, plasma, leukocytes, platelets, buffy coat, or any combination thereof. The higher density components can include, for example, red blood cells. Outlet tube 1717 and inlet tube 1712 fluidly couple cassette 1700 to irradiation chamber 1910. More specifically, outlet tube 1717 is provided for delivering an untreated lower density blood component, for example buffy coat, to irradiation chamber 1910 for exposure to photo energy, while inlet tube 1712 is provided for returning the treated lower density blood component to cassette 1700 for further routing. In addition, outlet tube 1717 is also provided for delivering a treated lower density blood component that has passed through irradiation chamber 1910 at least once, for another cycle of exposure of UVA radiation through irradiation chamber 1910.

Inlet tube 1711 and outlet tube 1716 couple treatment chamber 1841 of dual chamber bag 1725 to cassette 1700. Outlet tube 1716 is provided to deliver an untreated low density blood component, for example buffy coat, to treatment bag 1841. Outlet tube 1716 has hematocrit ("HCT") sensor 1125 operably connected thereto to monitor for the introduction of a high density blood component, such as red blood cells. HCT sensor 1125 is a photo sensor assembly and is operably coupled to a controller. HCT sensor 1125 sends a detection signal to the controller when red blood cells are detected in outlet tube 1716 and the controller will take the appropriate action. In addition, outlet tube 1716 is provided to deliver a treated lower density blood component, e.g. buffy coat, to treatment chamber 1841 which acts as a temporary collection chamber. The treated lower density blood component then is returned to the cassette 1700 via inlet tube 1711 for routing to irradiation plate 1910 via outlet tube 1717 to irradiation chamber 1910 for another cycle of exposure of UVA radiation. After another cycle of UVA radiation, the treated lower density blood component then is returned to cassette 1700 via inlet tube 1711. Inlet tube 1711 is provided to return an untreated or a treated low density blood component or a from treatment bag 1841 to cassette 1700 for further routing.

Inlet tubes 1709 and 1710 are respectively connected to a saline and anticoagulant storage bags (not shown) via spikes 1790 and 1791 and are provided for delivering saline and an anticoagulant fluid to cassette 1700 for further routing to the patient. In particular, anticoagulant is delivered to cassette 1700 via inlet tube 1710, then is pumped via peristaltic pump 1781 and then exits cassette 1700 via outlet tube 1719 and then is mixed with whole blood at multiport connector 1792A. The whole blood containing anticoagulant is then delivered to cassette 1700 via inlet tube 1706. From cassette 1700 the whole blood is then pumped via peristaltic pump 1782 to bowl 10 via outlet line 1715.

Inlet tube 1706 and outlet tubes 1719 and 1714 are coupled to a patient. Specifically, outlet tube 1714 is provided to return treated blood, saline, untreated blood components, treated blood components, and other fluids back to the patient. Inlet tube 1706 is provided for delivering untreated whole blood (and a predetermined amount of an anticoagulant fluid) from the patient to cassette 1700 for routing and treatment within photopheresis kit 1900. Outlet tube 1719 is specifically provided for delivering an anticoagulant fluid to inlet tube 1706.

Figure 65:
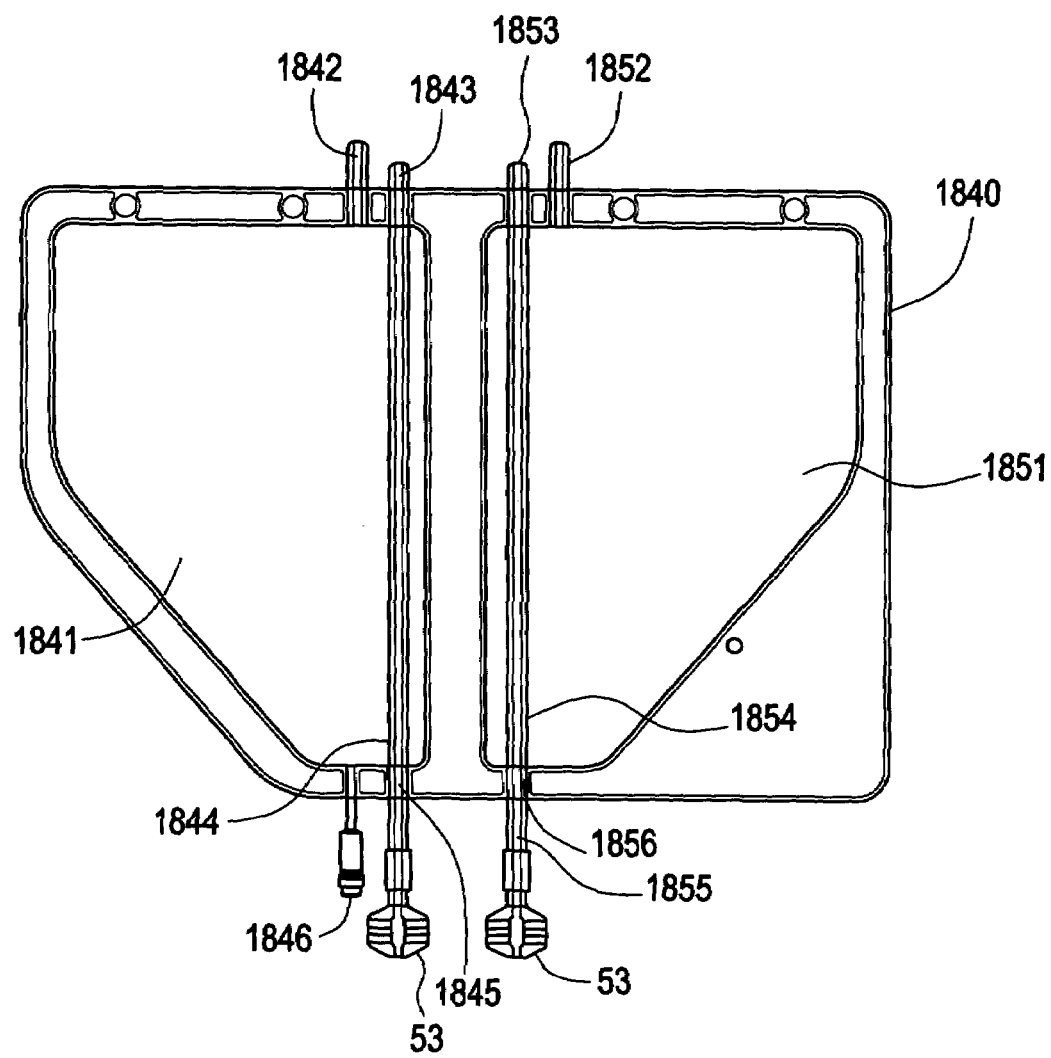
FIG. 65 is a front view of a dual chamber bag having a treatment chamber and a plasma collection chamber.

Inlet/Outlet tube 1713 and outlet tube 1718 couple plasma collection chamber 1851 of dual chamber bag 1840 to cassette 1700. More specifically, outlet tube 1718 delivers a blood component, such as plasma, to plasma collection chamber 1851. Inlet/Outlet tube 1713 can be used to either deliver red blood cells to plasma collection chamber 1851 from cassette 1700 or return the blood component(s) that build up in plasma collection chamber 1851 to cassette 1700 for further routing. Plasma collection chamber 1851 has an inlet port 1852 in fluid communication with cassette 1700 outlet tube 1718. Fluid inside plasma collection chamber 1851 is pumped out through opening 1856 which leads to outlet port 1853 through a channel 1854 inside the plasma collection chamber. Treatment chamber 1841 has an inlet port 1842 in fluid communication with cassette 1700 outlet tube 1717 (FIGS. 56 and 65). Fluid inside treatment chamber 1841 is pumped out of the chamber through opening 1845 located at near the bottom of the chamber leading to outlet port 1843 through channel 1844 inside treatment chamber 1841. The outlet port 1843 of treatment chamber 1841 is in fluid communication with cassette 1700 inlet tube 1712.

Figure 60:
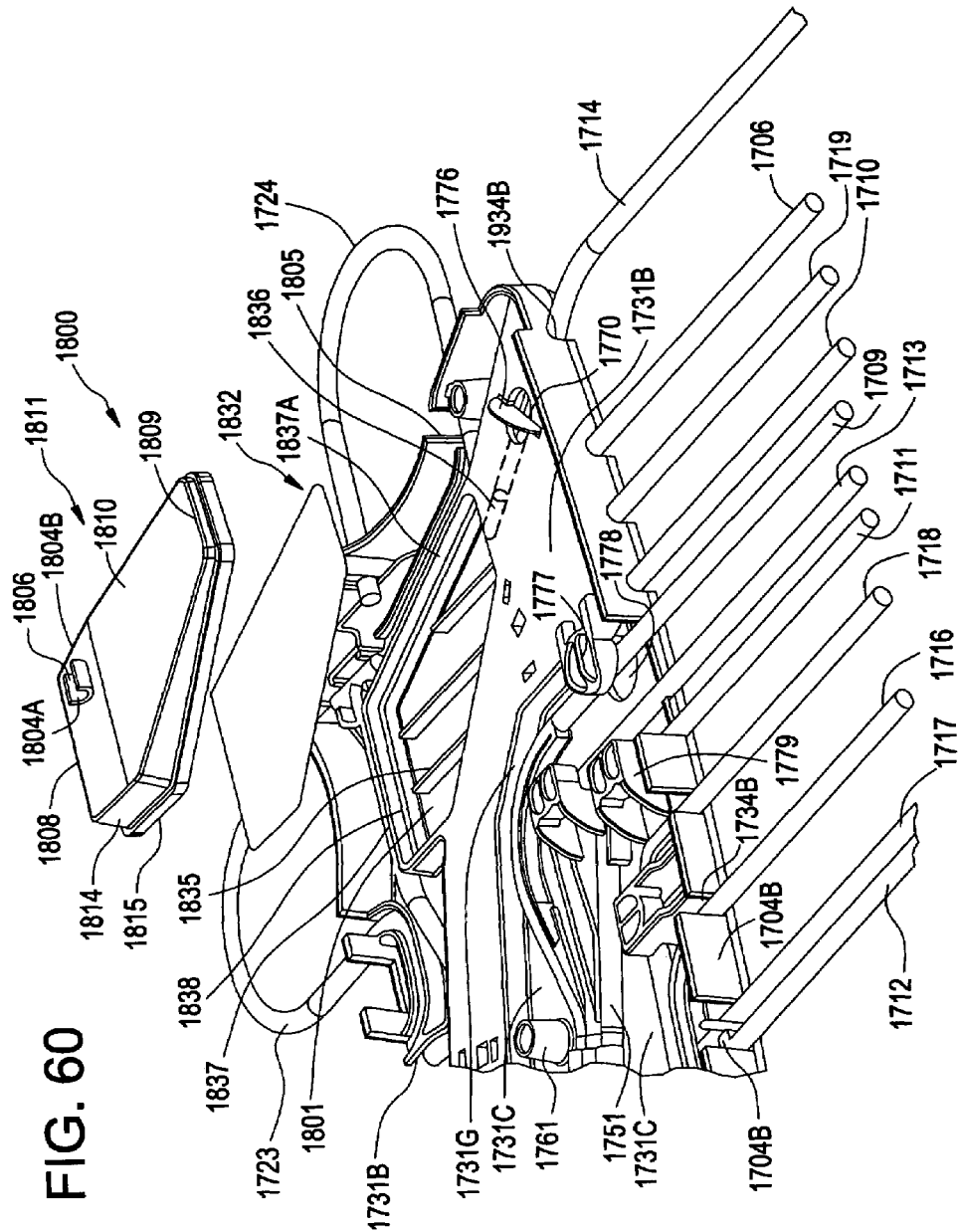
FIG. 60 shows a view of a portion of cassette of FIG. 56 having an exploded view of the filter.

Filter 1800 is illustrated in an exploded view in FIG. 60. Filter 1800 can be used in connection with almost any fluid, including treated or untreated red blood cells, white blood cells, buffy coat, plasma, or a combination thereof. Filter 1800 comprises a filter cover 1811, a filter media 1832, and a filter housing 1801. From top view, filter cover 1811 is a pentagon shaped structure comprising a roof 1810, a top longer side 1808, a base shorter side 1809, and wall 1814. Filter cover 1811 is connected to filter housing 1801 by any means known in the art, such as ultrasonic welding, heat welding, applying an adhesive, or by designing cover 1811 and housing 1801 so that a tight fit results between the two. One side of wall 1814 has a port 1806 that has openings 1804A and 1804B for receiving a portion of a flexible tubing located inside housing 1901 that has fluid communication with one end of pump tube loop 1724. The height of wall 1814 near longer side 1808 is larger than the height of wall 1814 near shorter side 1809 so there is more headspace inside filter 1800 near the longer side 1808 than near the shorter side 1809. During a photopheresis treatment, any air bubbles collected inside the filter chamber will be trapped in the headspace near longer side of filter 1800.

Surrounding the perimeter at the bottom of wall 1814 is a ridge 1815 that fits the top half of wall 1837 inside housing 1801. Ridge 1815 is designed to engage slot 1838 and keeps the filter media 1832 in place. Filter media 1832 preferably has a pore size of approximately 200 microns and can be formed of woven mesh, such as woven polyester. Fluid enters filter chamber 1812, the top half of the filter 1800, through hole 1804A, passes through filter media 1832 and then exits through outlet port 1836 through outlet hole 1805 which is connected to and has fluid communication with outlet tube 1714. Filter housing 1801 comprises a portion of top surface 1731C of base 1731. A plurality of supporting slab 1835 located on surface 1731C prevent filter media 1832 from collapsing and contact surface 1731C during a photopheresis treatment.

Pressure domes 1744, 1745, and 1746 are serially connected to and have fluid communication with tubes 1706, 1715, and 1714 respectively. In particular, pressure dome 1744 and pressure sensor 1754 measure the pressure inside tube 1706 of blood flowing from a patient or donor to cassette 1700. The pressure dome 1745 and pressure sensor 1755 measure the pressure inside tube 1715 leading from the cassette to the inlet tube of bowl 10. Likewise, pressure sensor 1756 and pressure dome 1746 measures the pressure inside tubing 1714 which is the pressure of the tube returning blood or blood components back to a patient or donor.

Pressure sensors 1754, 1755, and 1756 are coupled to controller 1554 (not shown) which is a properly programmed processor. Controller 1554 can be a main processor used to drive the entire system or can be a separate processor coupled to a main processor. Pressure sensors 1754, 1755, and 1756 produce electrical output signals representative of the pressure readings within tubes 1706, 1715, and 1714 respectively. Controller 1554 receives on a frequent or continuous basis data representing the pressure within tube 1714 which is representative of the pressure inside filter chamber 1812. Controller 1554 is programmed with values representing desired pressures within tubes 1706, 1715, and 1714. Controller 1554 continuously analyzes the pressure data it receives from pressure sensors 1754, 1755, and 1756 to determine whether the pressure readings are within a predetermined range from the desired pressure for tubes 1706, 1715, and 1714. Controller 1554 is also coupled to whole blood pump 1782 and return pump 1784. In response to the pressure data received from pressure sensors 1754, 1755, and 1756, controller 1554 is programmed to control the speed of whole blood pump 1782 and return pump 1784, thereby adjusting the flow rates through the pumps 1782 and 1784. Adjusting these flow rates in turn adjust the pressure within inlet tube 1706, outlet tube 1715 and filter chamber 1812. It is in this way that the pressure within the lines drawing and returning blood to and from the patient is maintained at acceptable levels. Alternatively, when the pressure readings within tubes 1706, 1715, and 1714 are not within desirable ranges, an alarm will be activated to alert an operator to take appropriate measure(s). In addition, the system may pause temporary to allow corrective actions to be taken by an operator.

Whole blood pump 1782 draws whole blood from a patient who is connected to photopheresis kit 1900 via a needle connected to port 1793. The rotational speed of whole blood pump is set so that the pressure of the line drawing the whole blood from the patient is at an acceptable level. Upon being drawn from the patient, the whole blood passes into cassette 1700 via inlet tube 1706. Inlet tube 1706 is fluidly connected to bowl 10. Pressure sensor 1754 continuously monitors the pressure within tube 1706 through pressure dome 1744 and transmits corresponding pressure data to controller 1554. Controller 1554 analyzes the received pressure data and if necessary adjusts the speed of whole blood pump 1782, thereby adjusting the flow rate and pressure within inlet tube 1706. Controller 1554 adjust the pump speed to ensure that the pressure is within the desired pressure range.

Before being returned to the patient, treated fluid (i.e. treated blood or treated blood components) must be filtered. Untreated fluids such as red blood cells also must be filtered and will subjected to the below filtering process. The treated fluid is fed into filter chamber 1812 through fluidly connected to pump loop tube 1724. The treated fluid enters filter chamber 1812 through opening 1804A and passes through filter media 1832. Filter media 1832 removes contaminants and other undesired materials from the treated fluid. The treated fluid passes through filter media 1832 and out of filter 1800 through opening 1805 of outlet port 1836 (FIG. 60). The treated fluid is then returned to the patient via outlet tube 1714, which is fluidly connected to outlet port 1836. The treated fluid is driven through filter chamber 1812 and outlet tube 1714 by return pump 1784.

Pressure sensor 1756 continuously monitors the pressure within filter chamber 1812 through outlet tube 1714 and transmits corresponding pressure data to controller 1554. Controller 1554 analyzes the received pressure data and compares it to the desired pressure value and range. If necessary, controller 1554 adjusts the speed of return pump 1784, thereby adjusting the flow rate and pressure within chamber 1812 and outlet tube 1714.

Irradiation Chamber

Figure 11:
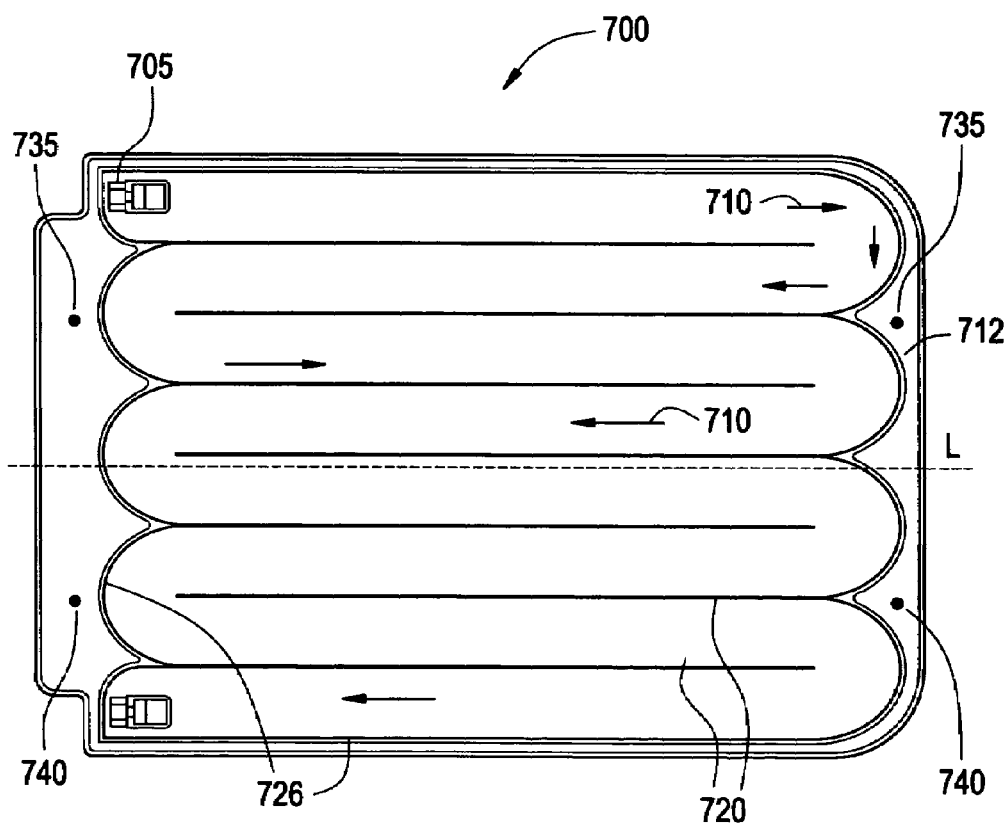
FIG. 11 is a front view of an irradiation chamber.

FIGS. 11-16 illustrate irradiation chamber 700 of photopheresis kit 1000 in detail. Referring first to FIG. 11, irradiation chamber 700 is formed by joining two plates, a front and a back plate having a thickness of preferably about 0.06 in. to about 0.2 in., which are preferably comprised of a material ideally transparent to the wavelength of electromagnetic radiation. In the case of ultraviolet A radiation, polycarbonate has been found most preferred although other materials such as acrylic may be employed. Similarly, many known methods of bonding may be employed and need not be expanded on here.

The first plate 702 has a first surface 712 and a second surface 714. In a preferred embodiment the first plate 702 has a first port 705 on a first surface 712, in fluid communications with the second surface 714. The second surface 714 of the first plate 702 has a raised boundary 726A defining an enclosure. The boundary 726A preferably extends substantially perpendicular from the second surface 714 (i.e. about 80-100 degrees). Extending from the second surface 714 (preferably substantially perpendicularly) are raised partitions 720A. The boundary 726A surrounds the partitions 720A. One end of each partition 720A extends and contacts the boundary 726A.

The second plate 701 has a first surface 711 and a second surface 713. In a preferred embodiment the second plate 701 preferably has a second port 730 on a first surface 711, in fluid communications with the second surface 713. The second surface 713 of the back plate 701 has a raised boundary 726B defining an enclosure. The boundary 726B preferably extends substantially perpendicular from the second surface 713 (i.e.

about 80-100 degrees). Extending from the second surface 713 (preferably substantially perpendicular) are raised partitions (720B). The boundary 726B surrounds the partitions 720B. One end of each partition 720A extends and contacts one side of boundary (726B).

The joining of the second surfaces of the first and second plates results in a fluid tight junction between boundaries 726A and 726B thereby forming boundary 726. Partitions 720A and 720B are also joined forming a fluid tight junction thereby forming partition 720. The boundary 726 forms an irradiation chamber 700 and together with the partitions 720 provides a pathway 710 having channels 715 for conducting fluid. The pathway maybe serpentine, zig-zag, or dove-tailed. Currently preferred is a serpentine pathway.

Figure 12:
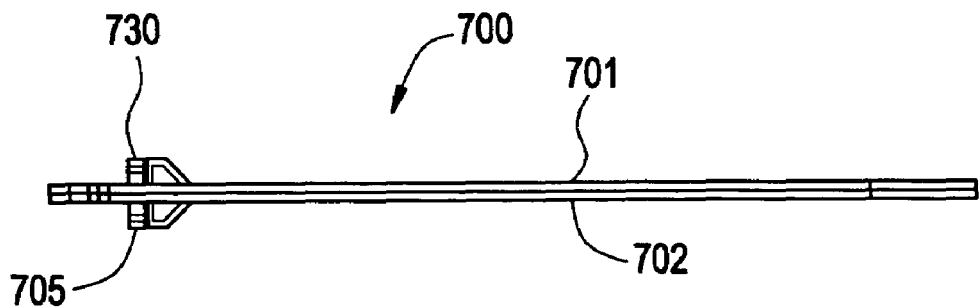
FIG. 12 is a side longitudinal view of the irradiation chamber of FIG. 11.

With reference to FIGS. 11 and 12, irradiation chamber 700 comprises a serpentine pathway 710 for conducting patient fluid, such as buffy coat or white blood cells, from inlet port 705 to outlet port 730, i.e., the serpentine pathway 710 is in fluid communication with inlet port 705 of front plate 702 and outlet port 730 of back plate 701. Patient fluid is supplied from cassette 1100 to inlet port 705 via outlet tube 1117. After photoactivation and passing through serpentine pathway 710, the treated patient fluid is returned to cassette 1100 via inlet tube 1112 (FIGS. 1 and 4). The patient fluid is driven by recirculation pump 1303. Self-shielding effects of the cells is reduced while the cells are photoactivated by irradiation impinging upon both sides of irradiation chamber 700.

FIG. 11 shows pin 740 and recess 735 which align the two plates of irradiation chamber prior to being joined together in a sealing arrangement by RF welding, heat impulse welding, solvent welding or adhesive bonding. Joining of the plates by adhesive bonding and RF welding is more preferred. Joining of the front and back plates by RF welding is most preferred as the design of the raised partitions 720 and perimeter 725 minimizes flashing and allows for even application of RF energy. Locations of pin 740 and recess 735 may be inside serpentine pathway 710 or outside of serpentine pathway 710. FIG. 2 also shows a view of an irradiation chamber with axis L. Rotation of chamber 700 180 degree about axis L gives the original configuration of the irradiation chamber. The irradiation chamber of the present invention has C₂ symmetry about axis L.

Figure 13:
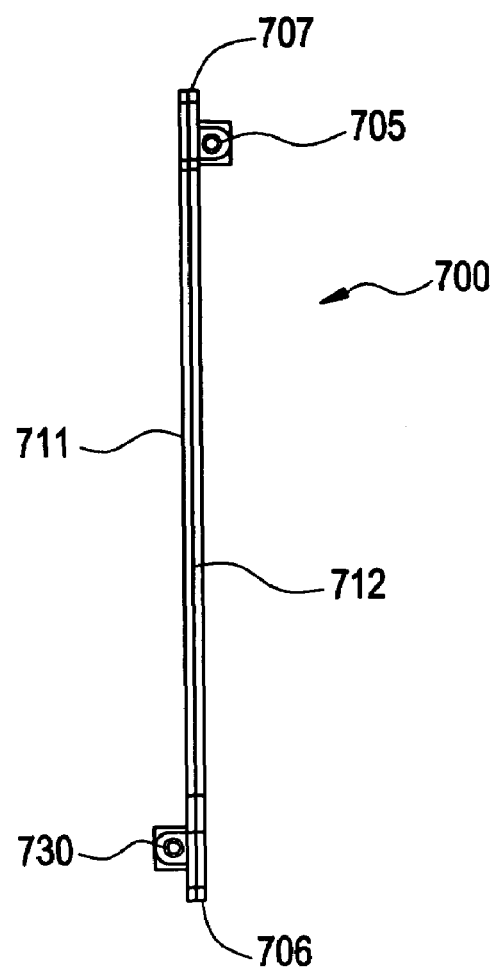
FIG. 13 is a side transverse view of the irradiation chamber of FIG. 11
Figure 16:
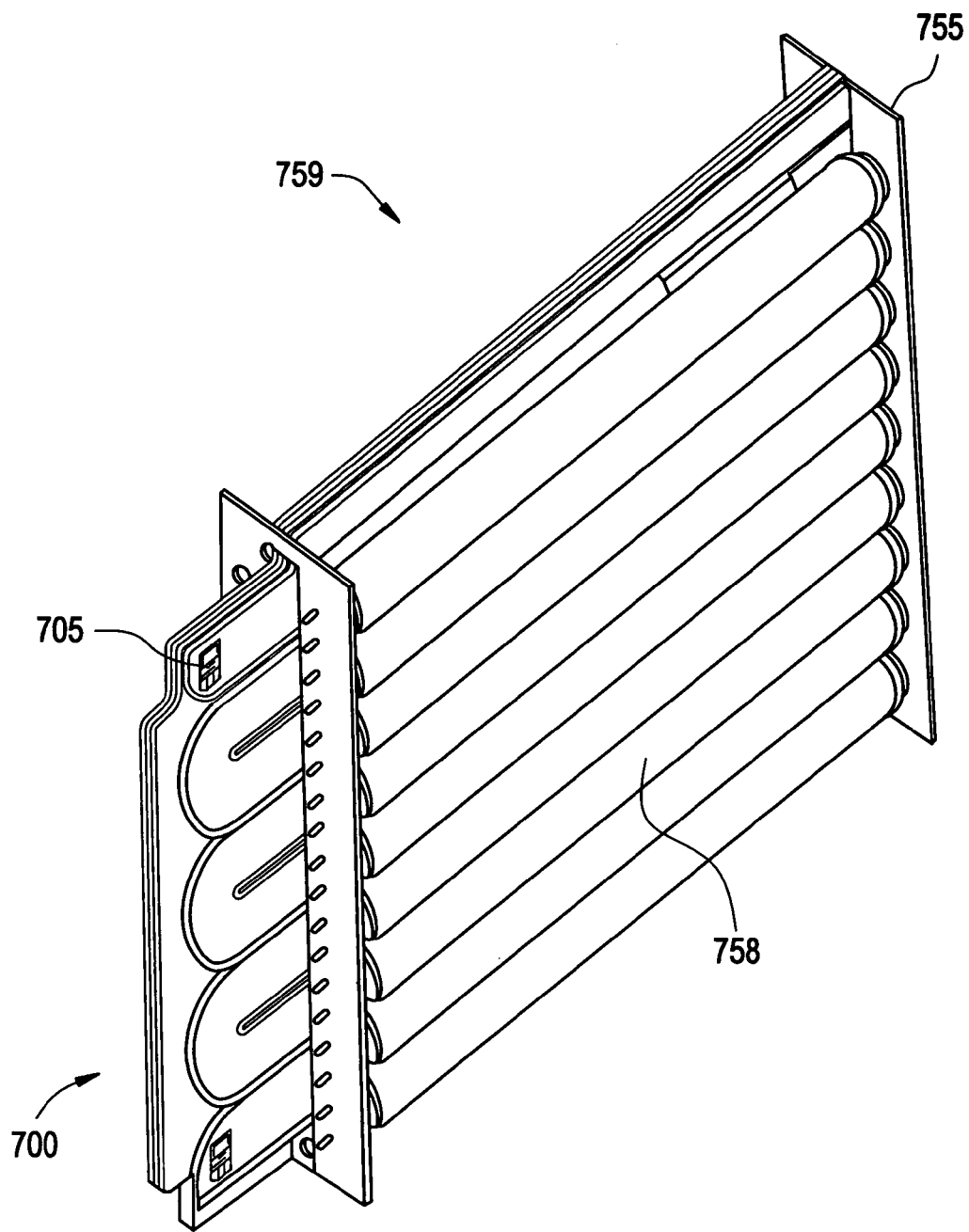
FIG. 16 is a perspective view of the irradiation chamber of FIG. 11 positioned within a UVA light assembly.

Referring to FIGS. 11, 13, and 16, the leukocyte enriched blood, plasma, and priming solution are delivered through inlet port 705 of front plate 702 of irradiation chamber 700 into channel 715. The channel 715 in the irradiation chamber 700 is relatively "thin" (e.g. on the order of approximately 0.04" as distance between two plates) in order to present large surface area of leukocyte rich blood to irradiation and reduce the self-shielding effects encountered with lower surface area/volume ratios. The cross section shape of channel 715 is substantially rectangular (e.g. rectangular, rhomboidal or trapezoidal) which has as its long side the distance between partition 720 and the distance between the plates as its short side. The shape of the cross section is designed for optimal irradiation of cells passing through channel 715. While a serpentine pathway 710 is preferred in order to avoid or minimize stagnant areas of flow, other arrangements are contemplated.

Figure 18:
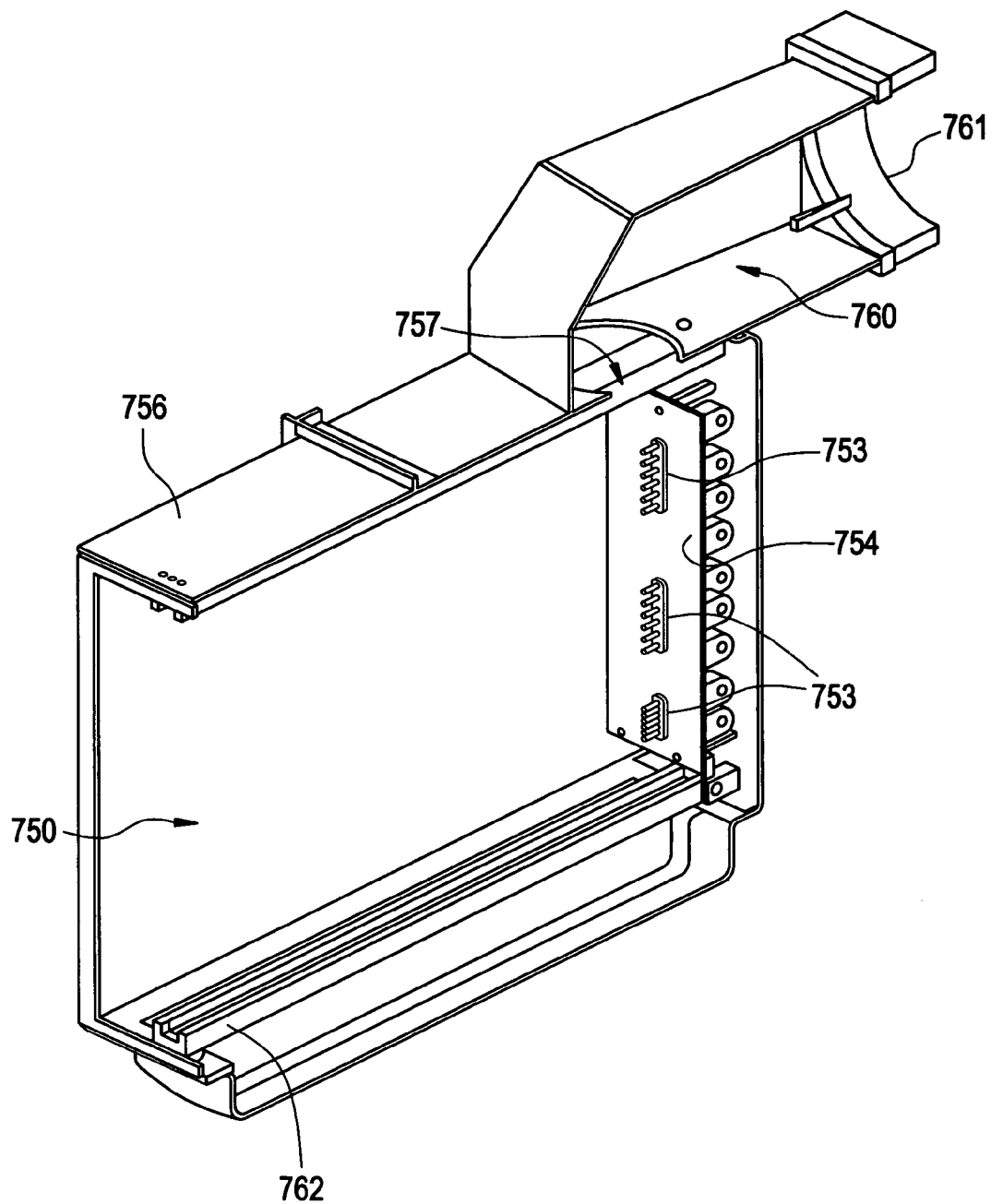
FIG. 18 is a cross-sectional view of an embodiment of the photoactivation chamber, without a UVA light assembly, used in the tower system of FIG. 17.

The irradiation chamber 700 allows efficient activation of photoactivatable agents by irradiation from a light array assembly, such as the PHOTOSETTE®'s two banks of UVA lamps (758) for activation (FIG. 16). The irradiation plate and UVA light assembly (759) are designed to be used in a setting where edge 706 is oriented downward and edge 707 points upward. In this orientation, fluids entering input port 705 can exit from outlet port 730 with the aid of gravity. In the most preferred embodiment, irradiation of both sides of the irradiation chamber takes place concurrently while still permitting facile removal of the chamber. UVA light assembly 759 is located within UV chamber 750 of permanent tower system 2000 (FIGS. 17 and 18).

The irradiation chamber's fluid pathway loops to form two or more channels in which the leukocyte-enriched blood is circulated during photoactivation by UVA light. Preferably, irradiation chamber 700 has between 4 to 12 channels. More preferably, the irradiation chamber has 6 to 8 channels. Most preferably, the irradiation chamber has 8 channels.

Figure 14:
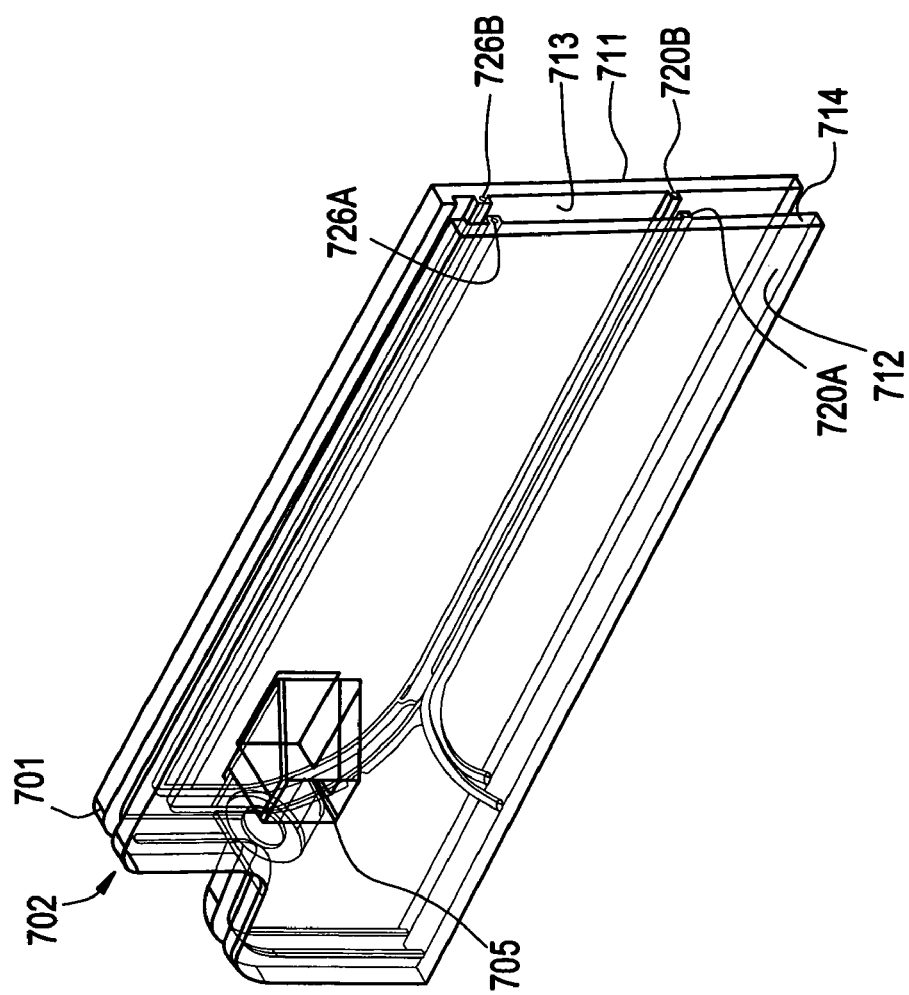
FIG. 14 is a cut-away view of a section of the first plate and the second plate prior to being joined together to form the irradiation chamber of FIG. 11.

FIG. 14 shows cut-away views of the irradiation chamber. The channels 715 of serpentine pathway 710 are formed by the joining of raised partition 720 and perimeter 726 of the plates.

The irradiation chamber of the present invention can be made from a biocompatible material and can be sterilized by known methods such as heating, radiation exposure or treatment with ethylene oxide (ETO).

Irradiation Chamber 2

Figure 62:
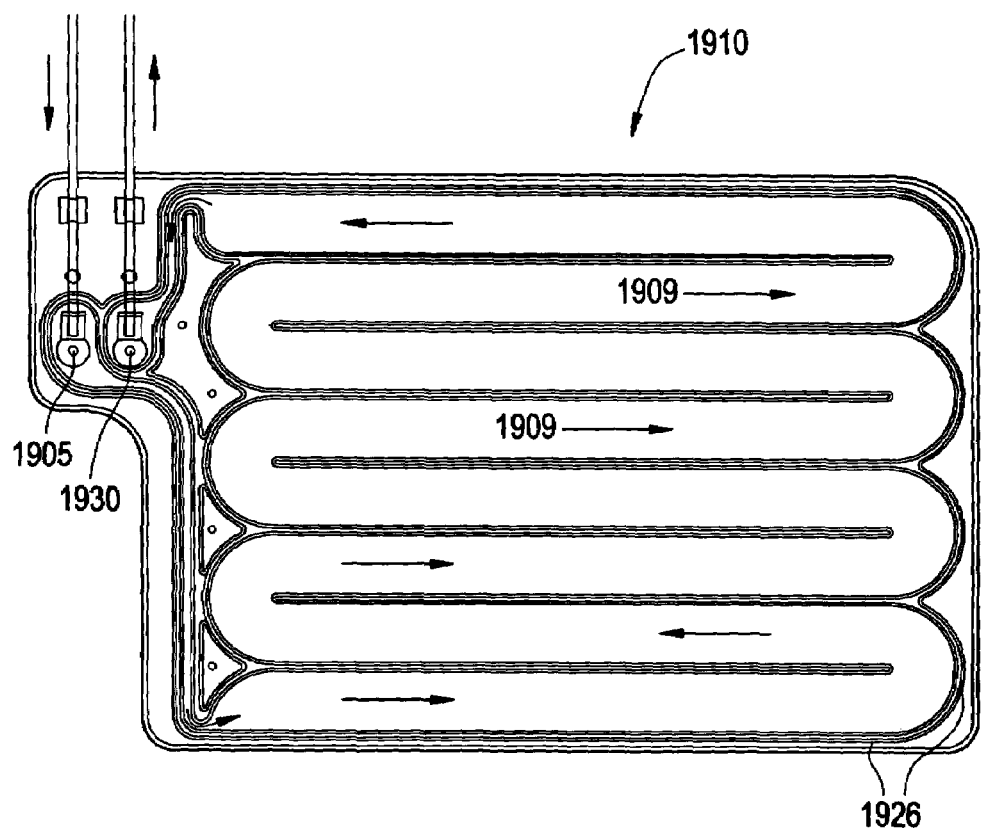
FIG. 62 is a front view of another irradiation chamber for use in extracorporeal photopheresis therapy embodying features of the present invention.
Figure 63:
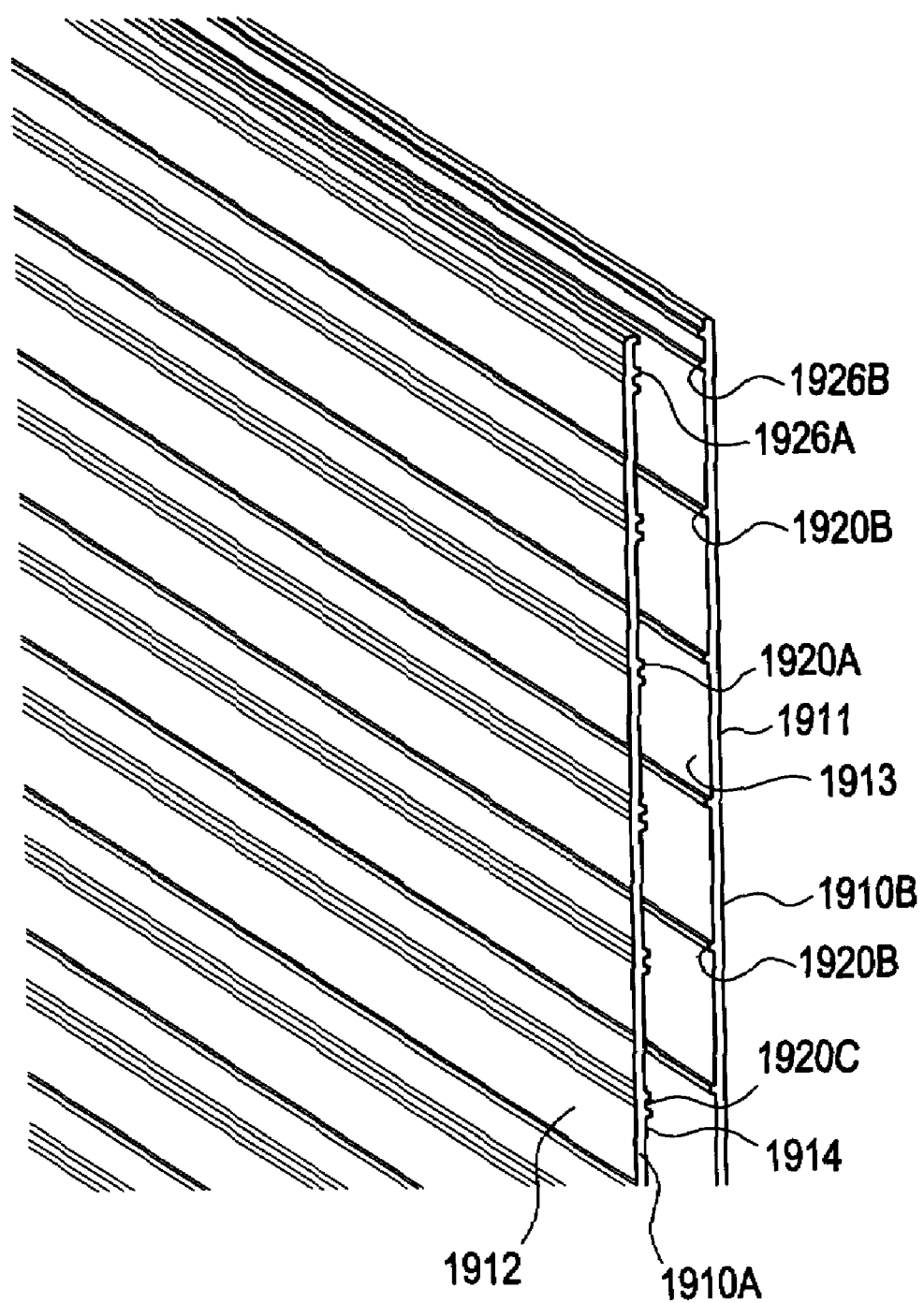
FIG. 63 is a cut-away view of a section of the first plate and the second plate prior to being joined together to form the irradiation chamber of FIG. 62
Figure 64:
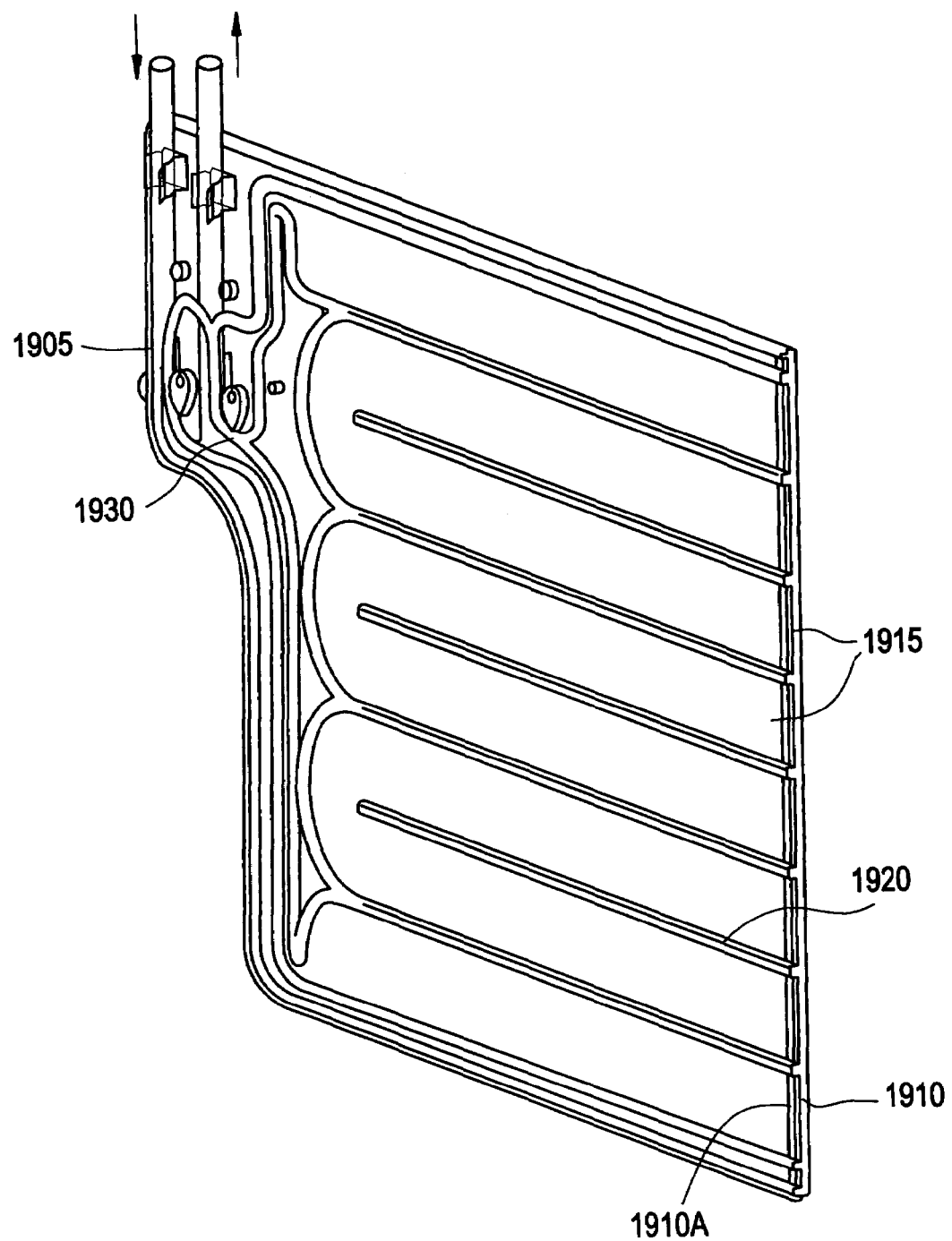
FIG. 64 is a cut-away dimensional end view of the irradiation chamber of FIG. 62.

Another embodiment of the irradiation chamber of the present invention is irradiation chamber 1910 as illustrated in FIGS. 62, 63, and 64. Irradiation chamber 1910 is formed by joining a first plate 1910A having a first surface 1912 and a second surface 1914 on which a "groove" is provided to fit a "tongue" on a second surface 1913 of a second plate 1910B. The plates have a thickness of preferably about 0.06 in. to about 0.2 in., and are preferably comprised of a material ideally transparent to the wavelength of electromagnetic radiation. The groove boundary 1926C on the second surface 1914 of the first plate 1910A is formed by a pair of ridges 1926A defining an enclosure for fluid flow. The pair of ridges 1926A preferably extends substantially perpendicular from the second surface 1914. The heights of the ridges on the second surface 1914 are about 0.035 to about 0.045 inch from the plate surface to the ridge tops. Within the area enclosed by the groove boundary 1926C are groove partitions 1920C formed by a pair of ridges 1920A extend from the second surface 1914. The groove partitions 1920A inside boundary 1926A provides a guided pathway from an inlet port 1905 to outlet port 1930 inside the area enclosed by groove boundary 1926A.

The second plate 1910B has a first surface 1911 and a second surface 1913. The second surface 1913 of the second plate 1910B has a ridge boundary 1926B defining an enclosure for fluid flow. The ridge boundary 1926B preferably extends substantially perpendicular from the second surface 1913. Extending from the second surface 1913 are ridge partitions 1920B inside boundary 1926B forming a guided pathway from an inlet port 1905 to outlet port 1930. The heights of the ridges on the second surface 1913 are about 0.045 to about 0.075 inch from the plate surface to the ridge tops. The groove partition 1920A providing sufficient space to accommodate the "tongue" of the ridge partition 1920B The joining of groove boundary 1926C and the ridge boundary 1926B of the first and second plates results in a fluid tight junction in a tongue and groove like manner thereby forming boundary 1926. Paired partitions 1920A and partition 1920B are also joined similarly to provide a fluid tight partition 1920. Joining the plate results in an irradiation chamber 1910 with a pathway 1909 having channels 1915 for conducting fluid. The serpentine pathway 1909 is in fluid communication with inlet port 1905 of first plate 1910A and outlet port 1930 of second plate 1910B. Patient fluid is supplied from cassette 1700 to inlet port 1905 via outlet tube 1717. After photoactivation and passing through serpentine pathway 1909, the treated patient fluid is returned to cassette 1700 via inlet tube 1712.

The leukocyte enriched blood, plasma, and priming solution are delivered through inlet port 1905 of first plate 1910A of irradiation chamber 1910 into channel 1915. The channels 1915 of serpentine pathway 1909 are formed by the joining of ridge partition 1920 and perimeter 1926 of the plates.

The method of irradiating cells using irradiation chamber 700 or 1910 during extracorporeal treatment of cells, preferably white blood cells, with electromagnetic radiation (UVA) to be used in the treatment of a patient (such as to induce apoptosis in the cells and administer the cells into the patient) will now be discussed.

In one embodiment of this method, a photoactivatable or photosensitive compound is first administered to at least a portion of the blood of a recipient prior to the extracorporeal treatment of the cells. The photoactivatable or photosensitive compound may be administered in vivo (e.g., orally or intravenously). The photosensitive compound, when administered in vivo may be administered orally, but also may be administered intravenously and/or by other conventional administration routes. The oral dosage of the photosensitive compound may be in the range of about 0.3 to about 0.7 mg/kg., more specifically, about 0.6 mg/kg.

When administered orally, the photosensitive compound may be administered at least about one hour prior to the photopheresis treatment and no more than about three hours prior to the photopheresis treatment. If administered intravenously, the times would be shorter. Alternatively, the photosensitive compound may be administered prior to or contemporaneously with exposure to ultraviolet light. The photosensitive compound may be administered to whole blood or a fraction thereof provided that the target blood cells or blood components receive the photosensitive compound. A portion of the blood could first be processed using known methods to substantially remove the erythrocytes and the photoactive compound may then be administered to the resulting enriched leukocyte fraction. In one embodiment, the blood cells comprise white blood cells, specifically, T-cells.

The photoactivatable or photosensitive compound may, in the case of some psoralens, be capable of binding to nucleic acids upon activation by exposure to electromagnetic radiation of a prescribed spectrum, e.g., ultraviolet light.

Photoactive compounds may include, but are not limited to, compounds known as psoralens (or furocoumarins) as well as psoralen derivatives such as those described in, for example, U.S. Pat. Nos. 4,321,919 and 5,399,719. The photoactivatable or photosensitive compounds that may be used in accordance with the present invention include, but are not limited to, psoralen and psoralen derivatives; 8-methoxypsoralen; 4,5'8-trimethylpsoralen; 5-methoxypsoralen; 4-methylpsoralen; 4,4-dimethylpsoralen; 4-5'-dimethylpsoralen; 4'-aminomethyl-4,5',8-trimethylpsoralen; 4'-hydroxymethyl-4,5',8-trimethylpsoralen; 4',8-methoxypsoralen; and a 4'-(omega-amino-2-oxa) alkyl-4,5',8-trimethylpsoralen, including but not limited to 4'-(4-amino-2-oxa)butyl-4,5',8-trimethylpsoralen. In one embodiment, the photosensitive compound that may be used comprises the psoralen derivative, amotosalen (S-59) (Cerus, Corp., Concord, Calif.). See, e.g., U.S. Pat. Nos. 6,552,286; 6,469,052; and 6,420,570. In another embodiment, the photosensitive compound that may be used in accordance with the invention comprises 8-methoxypsoralen.

Methoxsalen is a naturally occurring photoactive substance found in the seed of the Ammi majus (umbelliferae plant). It belongs to a class of compounds known as psoralens or furocoumarins. The chemical name is 9-methoxy-7H-furo [3,2-g][1]-benzopyran-7-one. The formulation of the drug is a sterile liquid at a concentration of 20 mcg/mL in a 10 mL vial. See http://www.therakos.com/TherakosUS/pdf/uvadexpi.pdf. Toxicology studies of extracorporeal photopheresis and different dosages of UVADEX® and ultraviolet light in beagle dogs is located in the investigator's brochure.

Next, the portion of the subject's blood, recipient's blood, or the donor's blood to which the photoactive compound has been administered is treated by subjecting the portion of the blood to photopheresis using ultraviolet light. The photopheresis treatment may be carried out using long wavelength ultraviolet light (UVA) at a wavelength within the range of 320 to 400 nm. Such a range is not limiting, however, but is merely provided as an example. The exposure to ultraviolet light during the photopheresis treatment may have a duration of sufficient length to deliver, for example, about 1-2 $J/cm^2$ to the blood.

The photopheresis step is carried out in vitro by installing irradiation chamber 700 into photoactivation chamber 750 of permanent tower system 2000 (FIGS. 17 and 18) or irradiation chamber 1910 into photoactivation chamber 750 of permanent tower system 3000. In one embodiment, when the photopheresis step is carried out in vitro, at least a fraction of the treated blood is returned to the subject, recipient, or donor. The treated blood or the treated enriched leukocyte fraction (as the case may be) may then be administered back to the subject, recipient, or donor.

The photopheresis process consists of three phases including: 1) the collection of a buffy-coat fraction (leukocyte-enriched), 2) irradiation of the collected buffy coat fraction, and 3) reinfusion of the treated white blood cells. This process will be discussed below in greater detail. Generally, whole blood is centrifuged and separated in centrifuge bowl 10. A total of approximately 240 ml of buffy coat and 300 ml of plasma are separated and saved for UVA irradiation.

Figure 15:
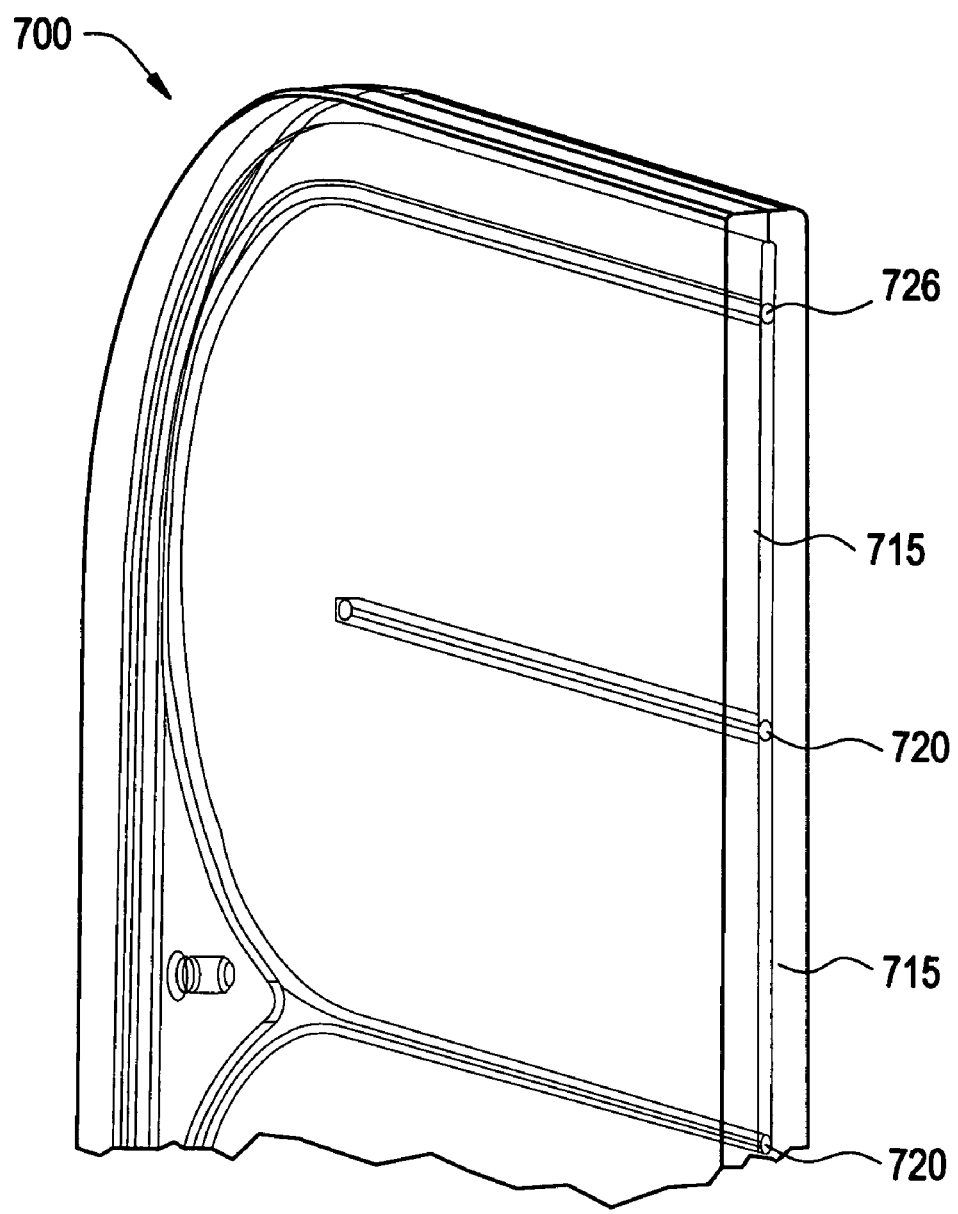
FIG. 15 is a cut-away dimensional end view of the irradiation chamber of FIG. 11.

The collected plasma and buffy coat are mixed with heparinized normal saline and UVADEX®. (water soluble 8-methoxypsoralin). This mixture flows in a 1.4 mm thick layer through the irradiation chamber of the present invention. The irradiation chamber 700, is inserted in photoactivation chamber 750 of tower system 2000, or irradiation chamber 1910 into photoactivation chamber 750 of tower system 3000, between two banks of UVA lamps of the PHOTOSETTE® (FIG. 15). PHOTOSETTE® UVA lamps irradiate both sides of this UVA-transparent irradiation chamber 700 or 1910, permitting exposure to ultraviolet A light, yielding an average exposure per lymphocyte of 1-2 $J/cm^2$. Following the photoactivation period, the cells are removed from the irradiation chamber 700 or 1910.

In a preferred embodiment of the present invention the cells are removed by the action of gravity and any cells remaining in the chamber are displaced from the chamber with additional fluid selected from the group consisting of saline, plasma, and combinations thereof. For patients who are small such as children (e.g. under 30 kg) or patients whose vascular system is easily overloaded with fluids the amount of additional fluid used to was the irradiation chamber will preferably be not more than 2× the volume of the chamber, preferably not more than 1× the volume of the chamber, more preferably not more than 0.5× the volume of the chamber 0.25× the volume of the chamber. The treated cells volume is reinfused to the patient.

For a description of similar photopheresis systems and methods, see U.S. patent application Ser. No. 09/480,893, which is expressly incorporated herein by reference. Also useful herein are the methods and systems described in U.S. Pat. Nos. 5,951,509; 5,985,914; 5,984,887, 4,464,166; 4,428, 744; 4,398,906; 4,321,919; PCT Publication Nos. WO 97/36634; and WO 97/36581, all of which are entirely expressly incorporated herein by reference.

The effective amount of light energy that is delivered to the biological fluids may be determined using the methods and systems described in U.S. Pat. No. 6,219,584, which is entirely expressly incorporated herein by reference. Indeed, the application of ECP to the various diseases described herein may require an adjustment of the amount of light energy to optimize the treatment process.

Furthermore, the photosensitizing agent used in the ECP process may be removed prior to returning the treated biological fluid to the patient. For example, Methoxsalen (UVA-DEX®) is utilized in the ECP process. Methoxsalen belong to a group of compounds known as psoralens. The exposure to methoxsalen or other psoralens may cause undesirable effects on the subject, recipient, or donor such as phototoxicity or other toxic effects associated with psoralen and their decomposition products. Therefore, the psoralen, psoralen derivatives, or psoralen decomposition products that may remain in the biological fluid may be removed after UV exposure. A process for the removal of psoralen biological fluids is described in U.S. Pat. No. 6,228,995, which is entirely expressly incorporated herein by reference.

Centrifuge Bowl

In a specific embodiment, the present invention relates to methods and apparatus that separate fluid components, such as, for example, the components of a biological fluid by density or weight. Biological fluids encompass fluids that comprise, exist in, or are used in, or delivered to living organisms. Indeed, biological fluids may comprise bodily fluids and their components, such as blood cells, plasma, and other fluids that comprise biological components, including living organisms such as bacteria, cells, or other cellular components. Biological fluids may also comprise whole blood or specific whole blood components, including red blood cells, platelets, white blood cells, and precursor cells. In particular, it may be desirable to remove blood from a patient for treatment, such as for example, extracorporeal treatment. It is to be understood, however, that the present invention is adaptable to use with various centrifugal processing apparatus, and the specific example given herein is merely for illustrative purposes. Other uses for the separation techniques and apparatus may include other medical processes such as dialysis, chemotherapy, platelet separation and removal, and separation and removal of other specific cells. Additionally, the present invention may be used to separate other types of fluids that include a wide variety of non-medical uses, such as, for example, oil and fluid component separation. All components used in the present invention should not adversely affect biological fluids or render them unsuitable for their intended uses, such as those described herein and may be made of any suitable material compatible with uses described herein including, but not limited to plastics, such as polycarbonate, methyl methacrylate, styrene-acrylonitrile, acrylic, styrene, acrylonitrile or any other plastic. Where parts of the present invention are indicated to be attached together and form a fluid tight seal any appropriate conventional means of joining the parts may be used including but not limited to, adhesives, ultrasonic welding or RF welding.

The present invention has several advantages over centrifuges what use conventional Latham bowl. The Latham bowl in the UVAR® XTS™ system has one inlet port that allows whole blood to come into the bowl and one outlet port that allows plasma and buffy coat to come out. Having only two ports limits the volume of buffy coat that can be collected per cycle. Each cycle involves filling the bowl with whole blood; 2) spinning the bowl to separate whole blood into plasma, buffy coat, and red blood cells; 3) collecting buffy coat for treatment, 4) bringing the bowl to rest; and 5) returning collected plasma and red blood cells. This buffy coat collection method may be characterized as being "batch-like" as the volume of buffy coat required for irradiation treatment can only be collected after several cycles of buffy coat collection. The limited volume of collected buffy coat per cycle results from the accumulated red blood cells remained inside the bowl. Thus the accumulated red blood cells that can only be emptied at the end of a buffy coat collection cycle is an inherent limitation of the Latham Bowl.

The bowl of the instant invention has three separate fluid conduits that can be used as an inlet port and two outlet ports. The additional fluid conduits allows for 1) reduce patient treatment time by having continuous spinning during the entire buffy coat collection process without having to stop spinning the bowl for removal of accumulated red blood cells; 2) treat small blood volume patients; by having collected red blood cells returned to patients continuously, these patients may be more amenable to medical treatments requiring the use of the buffy coat or fractions thereof such as extracorporeal photopheresis; 3) better separation of different components of fractions of cells within the buffy coat due to the increased spinning or rotation time and 4) the ability to separate high density red blood cells fractions from whole blood. This centrifuge bowl also provides the opportunity for reduced treatment time for any medical procedure requiring buffy coat fractions to be collected from patients that are substantially free of red blood cells, such as extracorporeal photopheresis.

Figure 35:
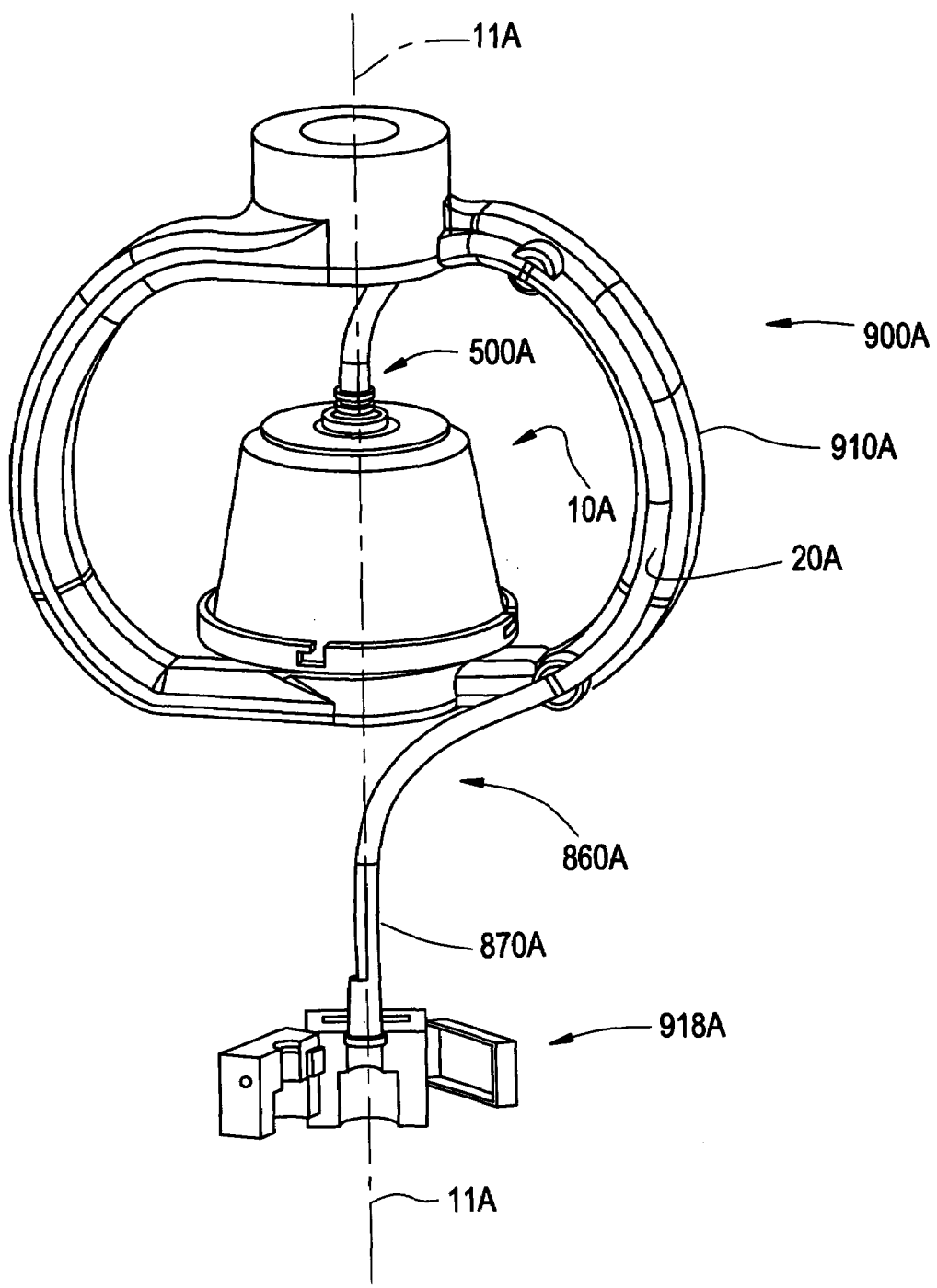
FIG. 35 illustrates an embodiment of a centrifuge bowl and a rotating frame.
Figure 36:
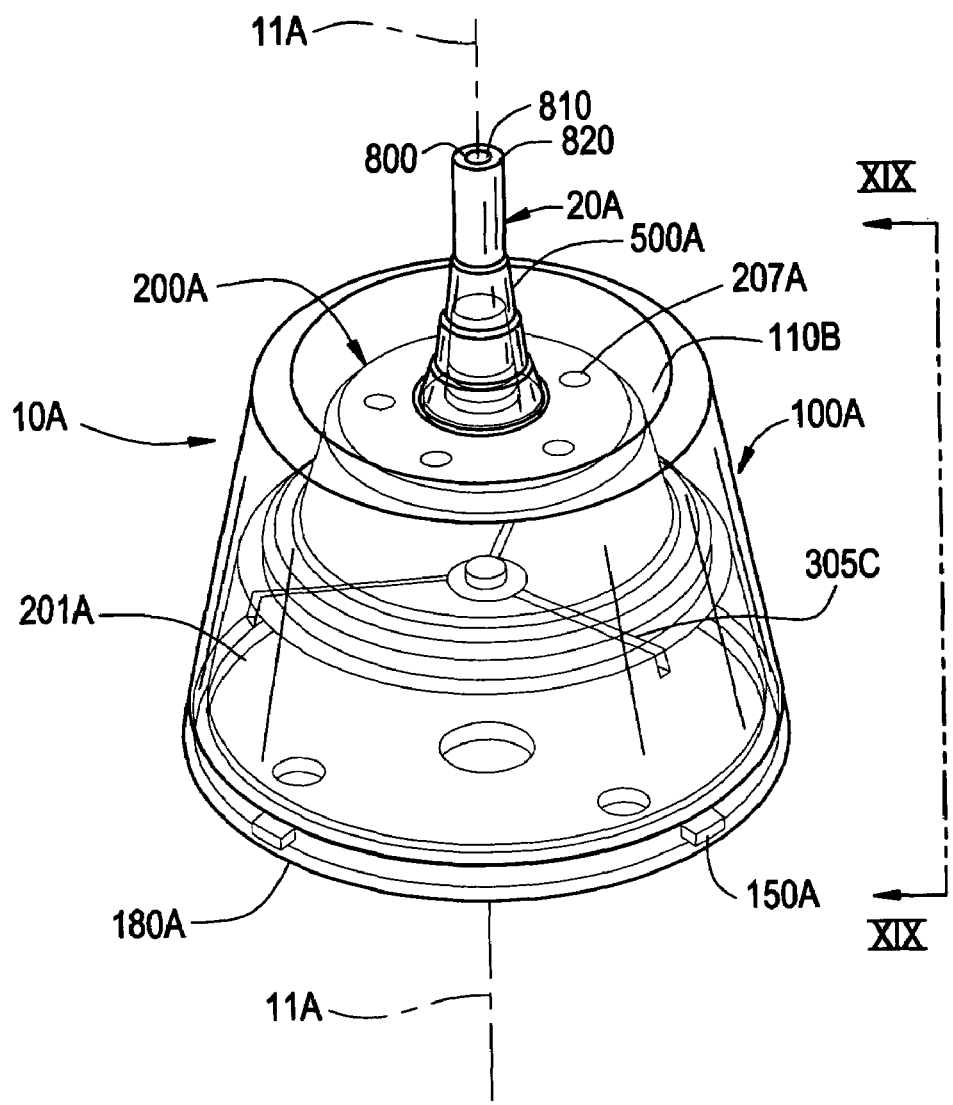
FIG. 36 is a dimensional view of the bowl of FIG. 35.

To achieve the objects in accordance with the purpose of the present invention, as embodied and broadly described herein, FIGS. 35 and 36 depict specific embodiments of the present invention. The embodiment depicted in FIG. 35 comprises a centrifuge bowl 10A, conduit assembly 860A, frame 910A and stationary restraint 918A. The centrifuge bowl 10A is in fluid communications with external conduit 20A of conduit assembly 860A. Lower sleeve end 832A (FIG. 46) of connection sleeve 500A is secured to bowl 10A. Upper sleeve end 831A of connection sleeve 500A is secured to external conduit 20A, connecting the external conduit 20A to bowl 10A and providing fluid communications from external conduit 20A to bowl 10A. The fluid communications enables fluid 800 to be supplied through external conduit 20A to the bowl 10A. Similarly this fluid communications also enables separated fluid components 810 and 820 to be removed from bowl 10A through external conduit 20A. Bowl 10A and frame 910A are adapted to be rotated around center axis 11A.

Referring to FIG. 36, bowl 10A comprises outer housing 10A, connection sleeve 500A, top core 200A, bottom core 201A, and housing floor 180A. Outer housing 100A may be constructed of any suitable biocompatible material as previously described for the purpose of the illustration in FIG. 36 the outer housing 100A is constructed of clear plastic so that cores 200A and 201A are visible there through. Outer housing 100A is attached to a housing floor 180A, which in turn comprises protrusions 150A for locking bowl 10A into a rotational device such as rotational device 900A. Bowl 10A is preferably simplified in construction and is easy to manufacture by molding or other known manufacturing processes, such that it may be disposable or used for a limited number of treatments, and is most preferably capable of containing about 125 ml of fluid, such fluid possibly being pressurized. In alternative embodiments, the volume capacity of the bowl may vary depending upon the health of the patient and his or her allowable extracorporeal volume. The volume capacity of the bowl may also vary depending upon the use of the bowl or the particular treatment for which the bowl is utilized. Additionally, to avoid contamination of biological fluids, or exposure of persons involved in the processing operation to the fluids, the transfer operations are preferably carried out within a sealed flow system, possibly pressurized, preferably formed of flexible plastic or similar material which can be disposed of after each use.

Figure 37:
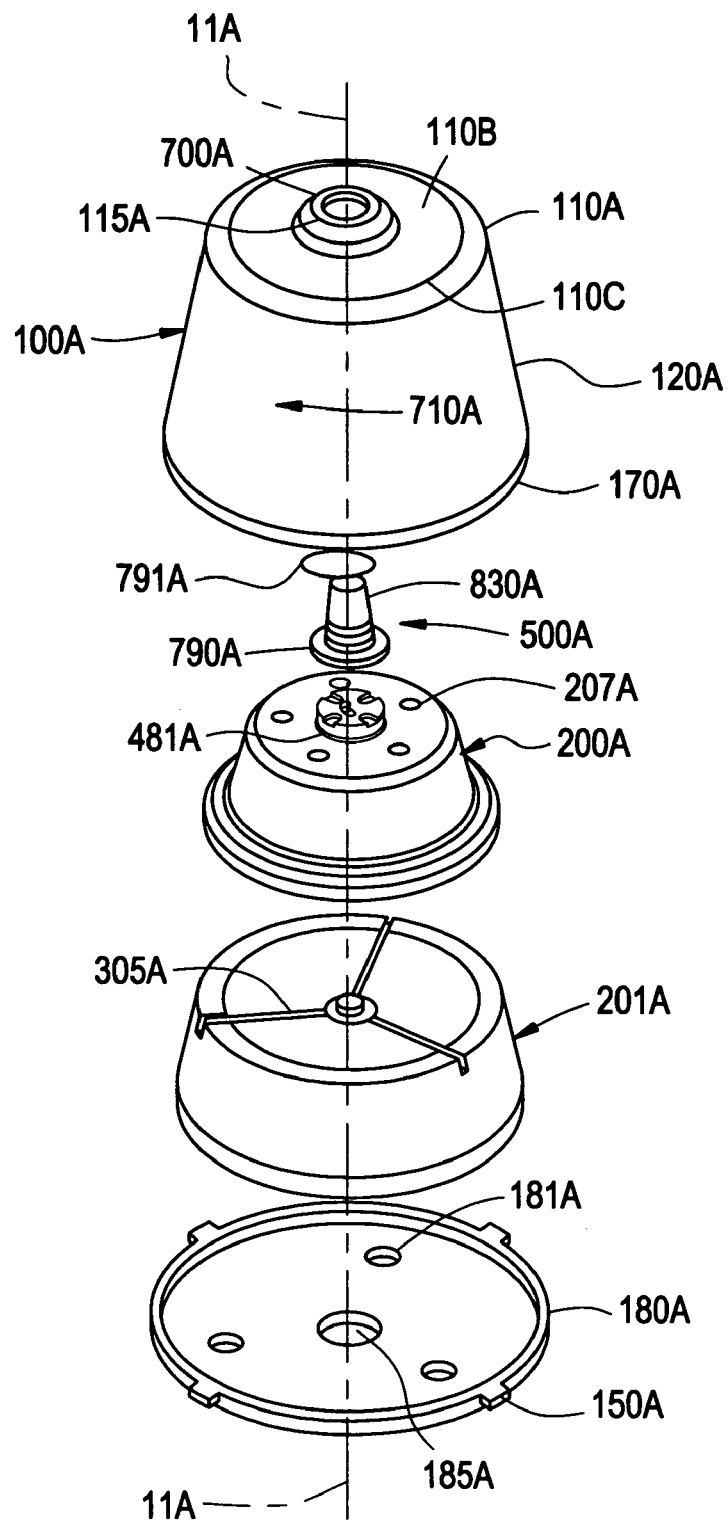
FIG. 37 is an exploded view of the bowl of FIG. 36.

As is illustrated in FIGS. 36 and 37, the outer housing 100A is substantially conical having an upper housing end 110A, an outer housing wall 120A and a lower housing end 190A. Outer housing 100A may be made of plastic (such as those plastics listed previously), or any other suitable material. Upper housing end 110A has an outer surface 110B, inner surface 110C and housing outlet 700A providing a passage between said surfaces. Preferably the upper housing will also have a neck 115A formed about the housing outlet 700A. The housing outlet 700A and neck 115A are sized to allow body 830A of the connection sleeve 500A to pass through while retaining sleeve flange 790A, which extends from the body 830A of connection sleeve 500A. In one embodiment of the present invention an o-ring 791A may be inserted between the sleeve flange 790A and inner surface 110C of the housing end 110A to ensure a fluid tight seal is provided. In an alternative embodiment of the present invention illustrated in FIG. 53, a second sleeve flange 790B extends from the body 830A of connection sleeve 500B distal to the sleeve flange 790A. Both sleeve flange 790A and 790B being adapted to fit within neck 115A and retain o-ring 791A therebetween. A fluid tight seal is provided in this embodiment by the o-ring contacting body 830A and inner surface 110C of the housing end 110A adjacent to the neck 115A. However, connection sleeve 500A can be secured to bowl 10A by any suitable means, including for example, a lip, groove, or tight fit and adhesive with a component of bowl 10A. The outer housing wall joins the upper housing end 110A and lower housing end 190A. Lower housing end 190A is attached to a housing floor 180A of greater diameter than upper end 110A. Housing floor 180A is adapted to mate with the lower housing end 190A and provide a fluid tight seal therewith. Any conventional means may be used to secure the lower housing end 190A to the housing floor 180A, including but not limited to, adhesives, ultrasonic welding or RF welding. Housing floor 180A may have an indentation 185A that is used to collect denser fluid 810. The diameter of outer housing 100A increases from upper housing end 110A to lower housing end 190A.

Figure 51:
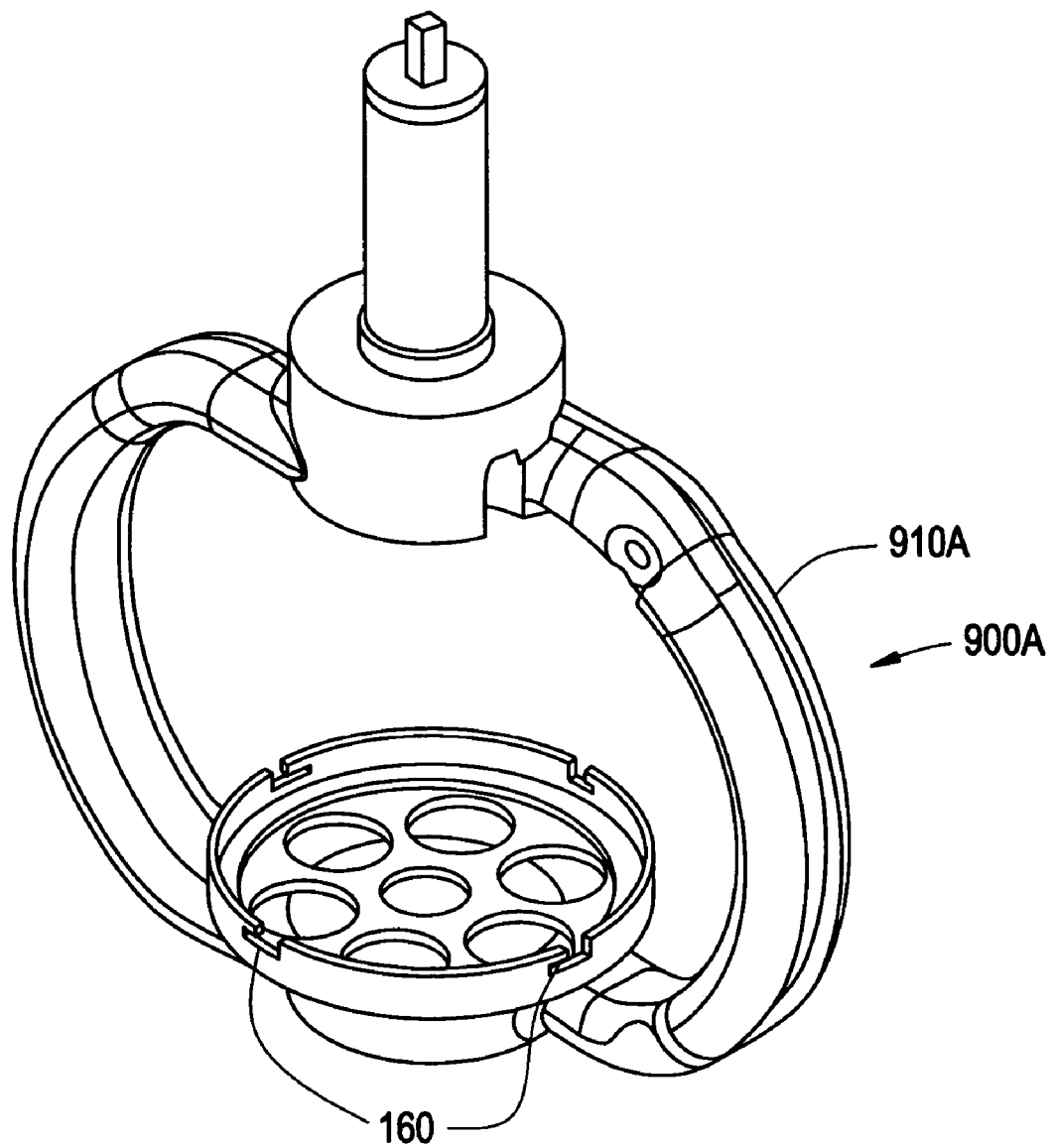
FIG. 51 illustrates a dimensional view of the rotating frame of FIG. 35.
Figure 52:
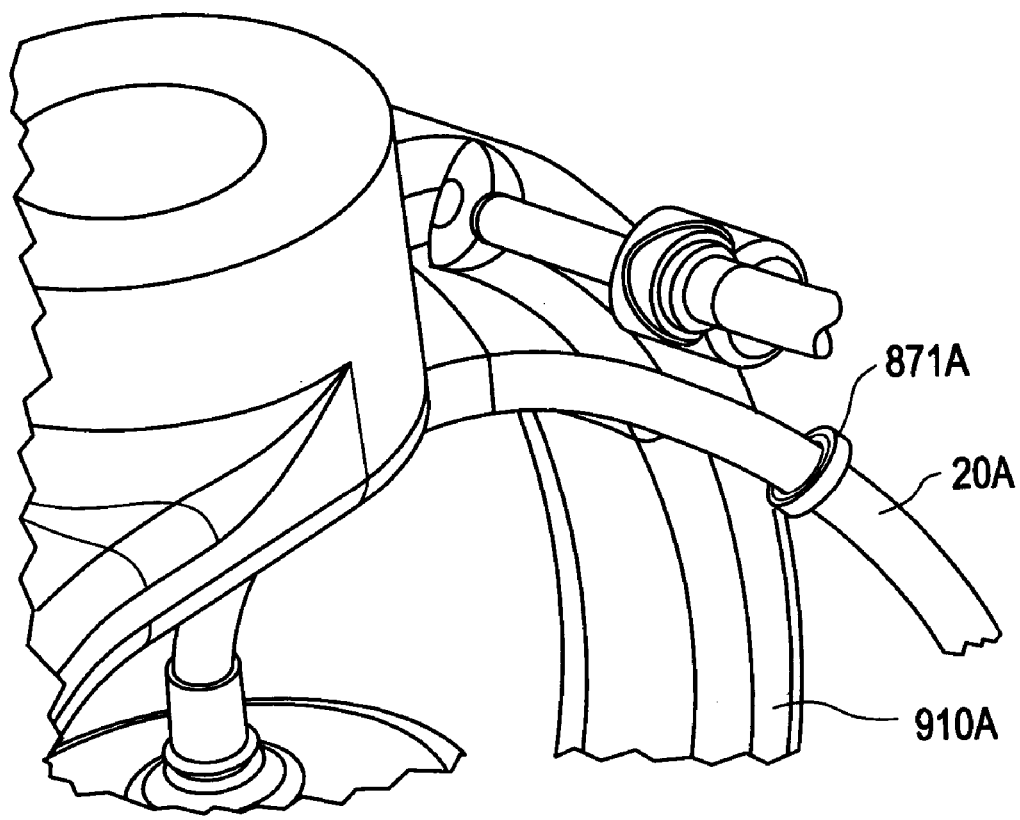
FIG. 52 is an enlarged view of a holder for an external conduit.

Outer housing 100A is adapted to rotatably connect to a rotational device 900 (FIG. 35), such as for example, a rotor drive system or a rotating bracket 910. The rotatable connection may, for example, be a bearing that allows free rotation of bowl 10A. Outer housing 100A preferably has a locking mechanism. The locking mechanism may be one or more protrusions 150A designed to interact with corresponding indentations in a centrifuge container or any other suitable interconnect or locking mechanism or equivalent known in the art. The locking mechanism may also comprise a key slot 160 (FIG. 51).

Referring to FIG. 37, outer housing 100A and the base 180A define an interior volume 710A in which cores 200A and 201A will fit when bowl 10A is assembled. When fully assembled, cores 200A and 201A are fully within interior volume 710A of outer housing 100A, occupying a coaxial volume of interior volume 710A about axis 11A.

Figure 38:
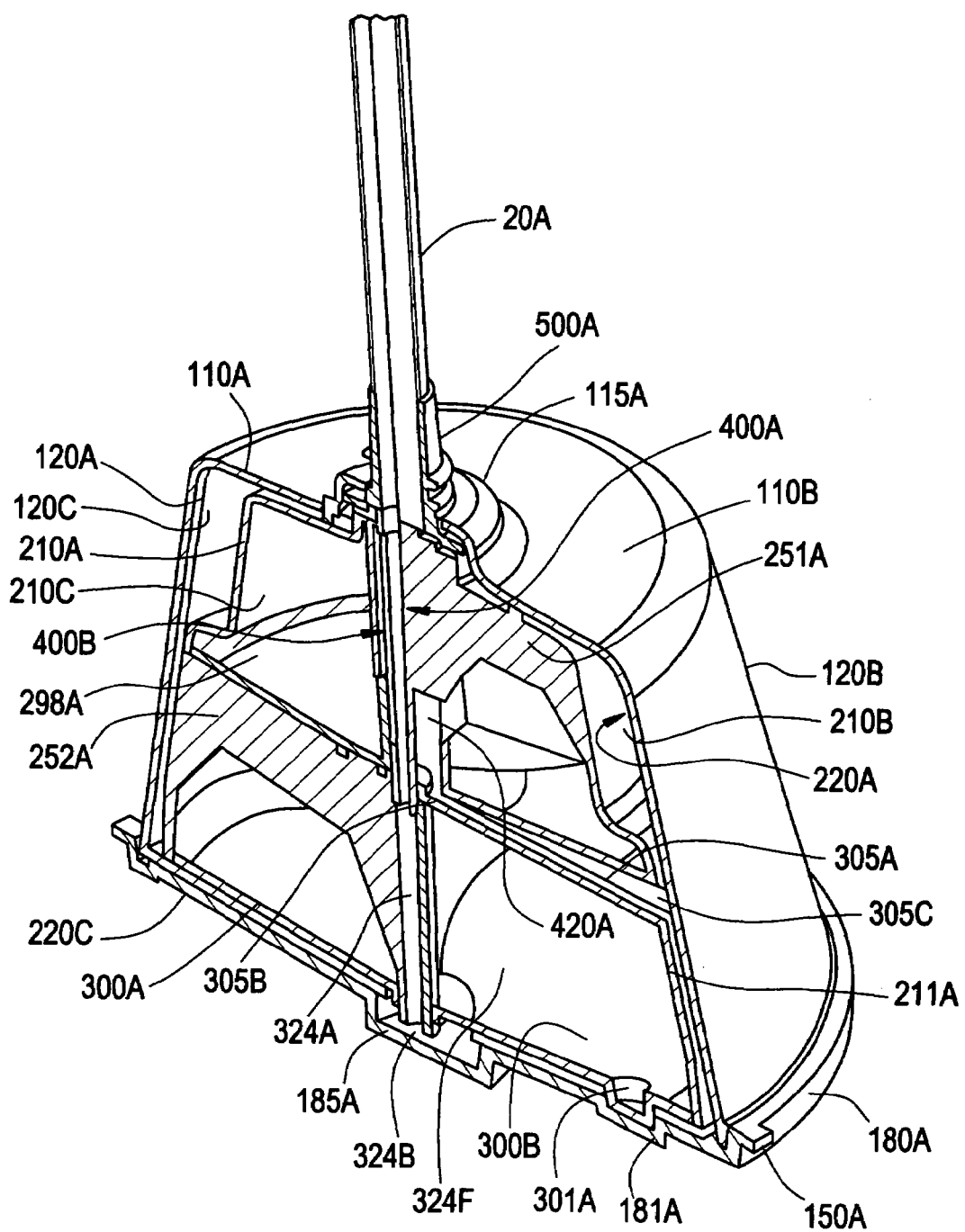
FIG. 38 shows a cross sectional view of the bowl of FIG. 36 along the line XIX-XIX.
Figure 40:
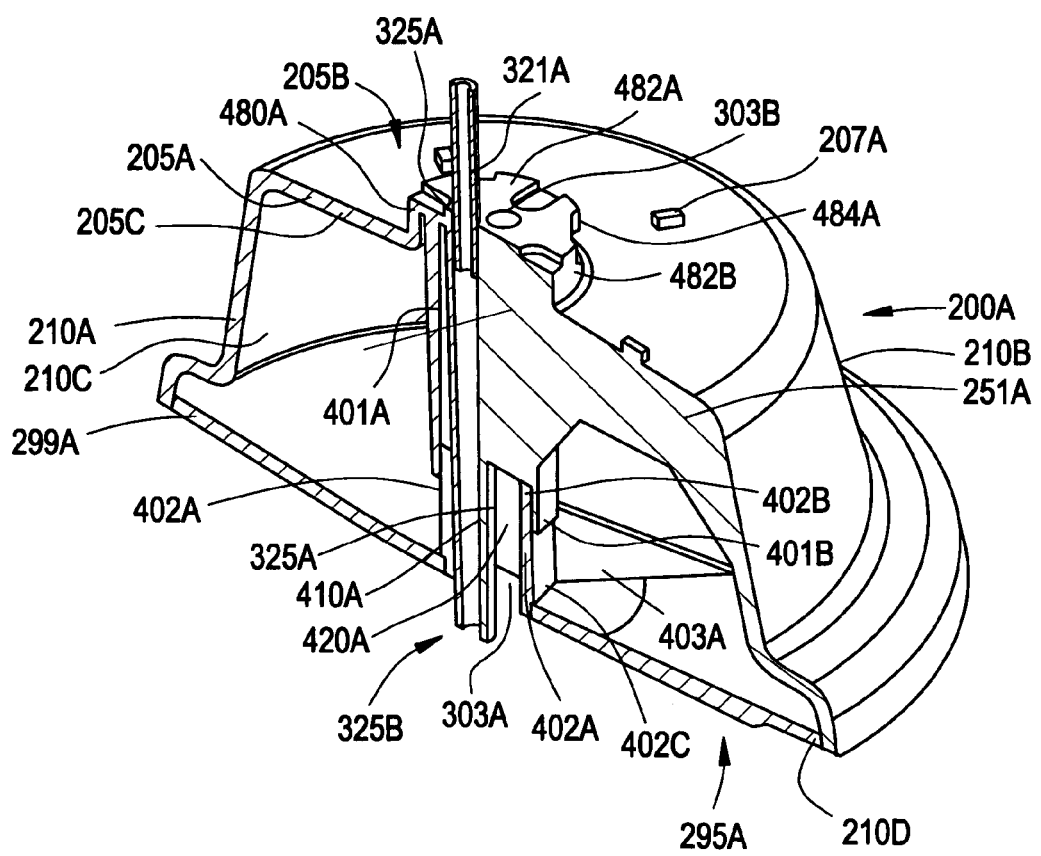
FIG. 40 shows a cross sectional view of the top core of the bowl of FIG. 37.

Referring to FIGS. 38, 40 and 44, the top core 200A and bottom core 201A are substantially conical and respectively have upper core ends 205A, 206A; outer core walls 210A, 211A; and lower core ends 295A, 296A. The cores 200A, 201A occupy coaxial volumes of interior volume 710A of bowl 10A and forming separation volume 220A between upper end 205A and outer wall 210A of top core 200A and outer wall 211A and lower core end 296A of bottom core 201A and outer housing 100A. Separation volume 220A is that space of interior volume 710A that is between cores 200A and 201A and outer housing 100A.

Figure 41:
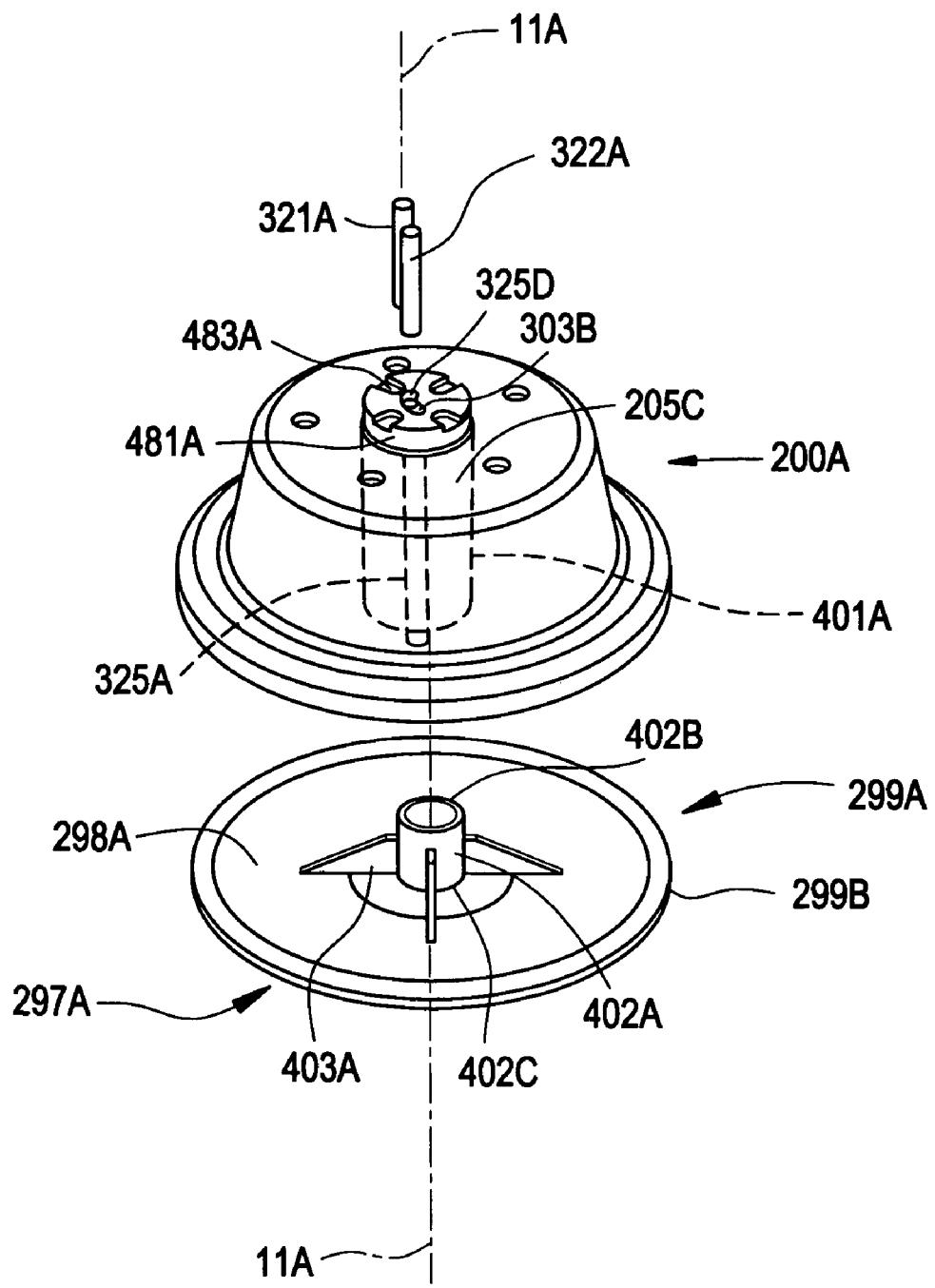
FIG. 41 shows a dimensional view of the top core and upper plate of FIG. 37.
Figure 42:
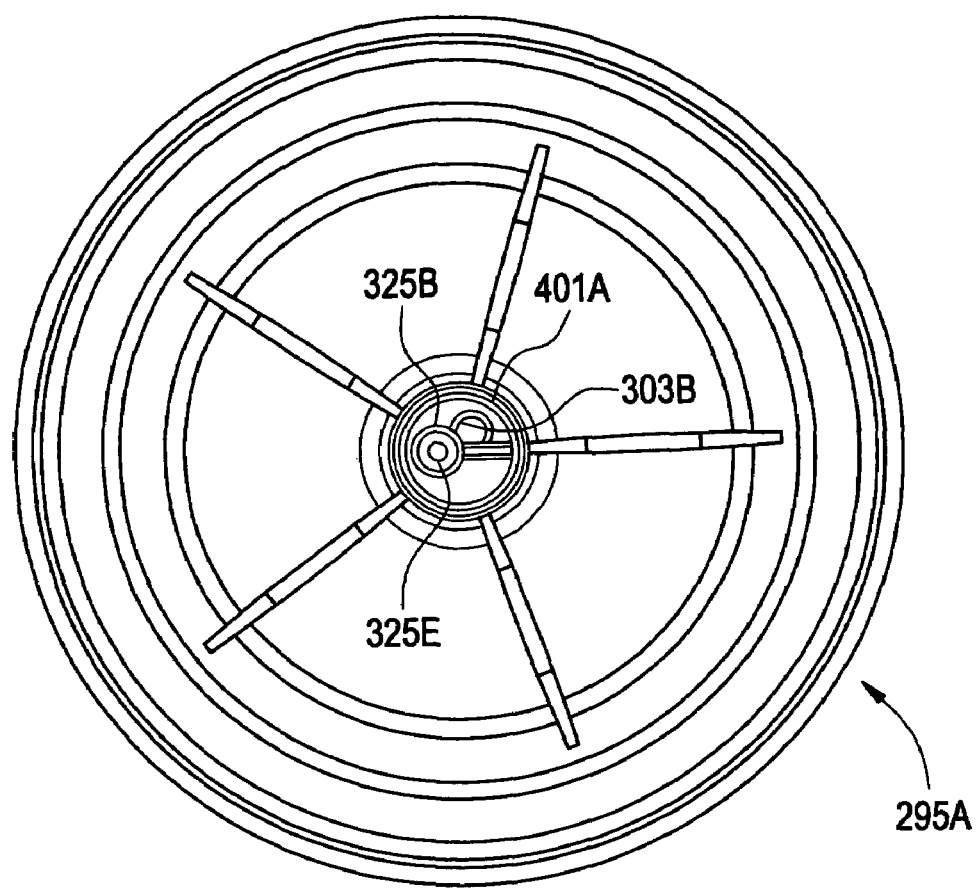
FIG. 42 shows a bottom view of the top core of FIG. 41.

As depicted in FIGS. 40 and 41 top core 200A comprises upper core end 205A and a lower core end 295A that are joined by outer core wall 210A. The outer core wall 210A having an outer surface 210B and inner wall surface 210C and a lower edge 210D. The diameter of top core 200A preferably increases from upper core end 205A to lower core end 295A. Upper core end 205A also comprises an outer surface 205B and an inner surface 205C. Centrally located about center axis and extending perpendicularly from the upper surface 205B is lumen connector 481A. Lumen connector 481A has a top surface 482A and a wall surface 482B. Top surface 482A has two passages 303B and 325D that provide fluid communications through the upper core end 205A with second bowl channel 410A and first bowl channel 420A respectively. Second bowl channel 410A is a conduit that has a conduit wall 325A that extends perpendicularly from the inner surface 481C of lumen connector 481A.

Figure 39A:
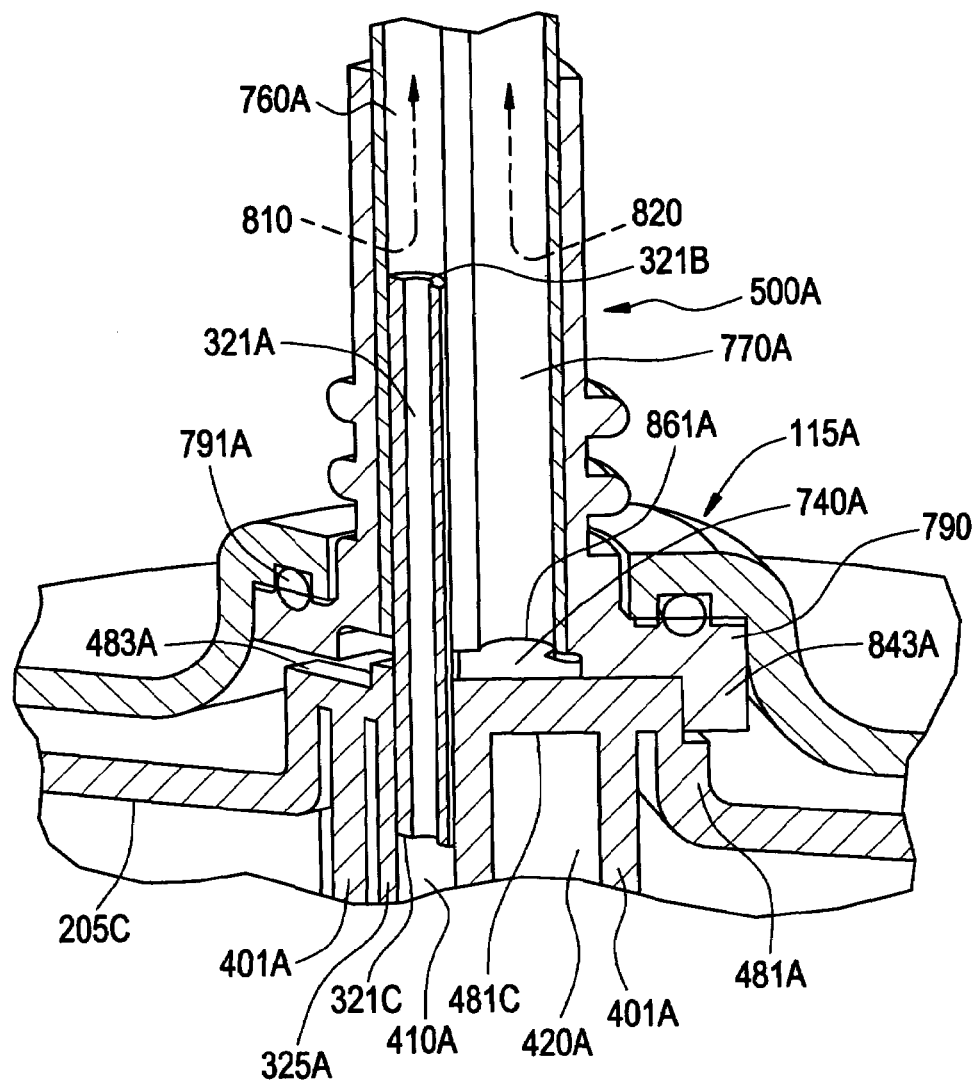
FIG. 39A shows a cross sectional view of a connection sleeve in place with a lumen connector of the bowl of FIG. 38 along the line XX.
Figure 39B:
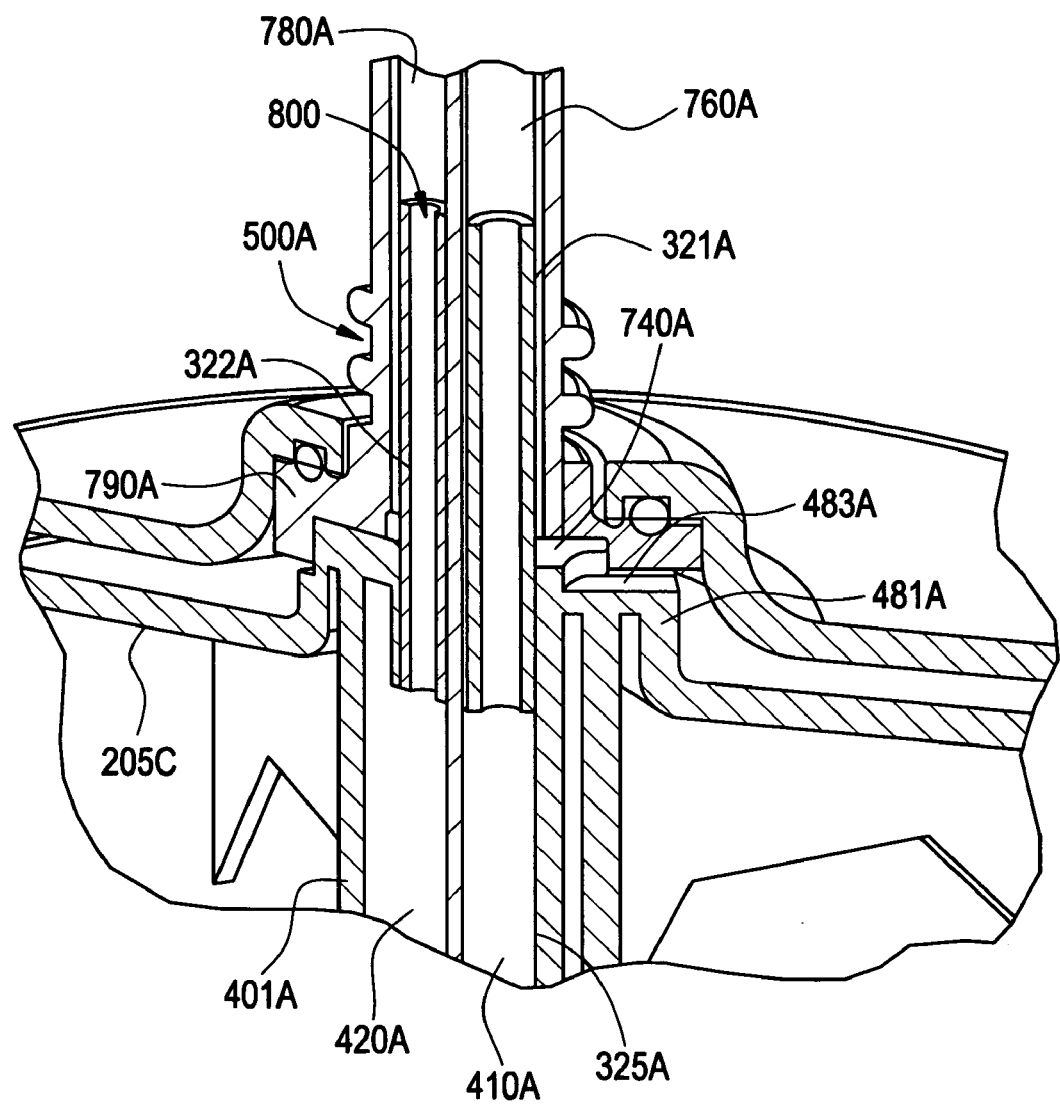
FIG. 39B shows another cross sectional view of a connection sleeve in place with a lumen connector of the bowl of FIG. 38.

As shown on FIGS. 39B, 39A and 40, second bowl channel 410 has fluid communication with conduit channel 760A through conduit 321A having a first end 321B and a second end 321C that is adapted to fit into passage 325D of lumen connector 481A. In operation conduit channel 760A of external conduit 20A has fluid communication with bowl channel 410A. First bowl channel 420A is a second conduit that has a channel wall 401A that extends substantially perpendicularly from inner surface 481C of the lumen connector 481A. As shown in FIGS. 39A, 39B and 40, first bowl channel 420A has fluid communication with conduit channel 780A of external conduit 20A through hollow cylinder 322A having a first end 322B and a second end 322C adapted to fit opening 303B top surface 482A. As is illustrated in one embodiment of the present invention, second bowl channel 410A is disposed within first bowl channel 420A. In an alternative embodiment of the present invention illustrated in FIG. 53, conduit wall 325A may be composed of upper part 325F and lower part 325G and be fused with channel walls 401A and 402A.

Top surface 482A also has indentation 483A which provides fluid communications with chamber 740A. When assembled, chamber 740A is defined by lumen mounting recess 851A less the volumes occupied by hollow cylinders 321A and 322A in the connection junction of connection sleeve 500A and lumen connector 481A. Chamber 740A has fluid communication with conduit channel 770A and with separation volume 220A near neck 115A through indentation 483A. Thus indentation 483A forms a passageway for the removal of second separated fluid component 820 through bowl chamber 740A. Optionally present on the outer surface 205B are a plurality of spacers 207A which extend from the outer surface and contact the inner surface 110C of the upper housing end 110A to ensure fluid communications between the separation volume 220A and the passageway formed by the indentations 483A.

Figure 53:
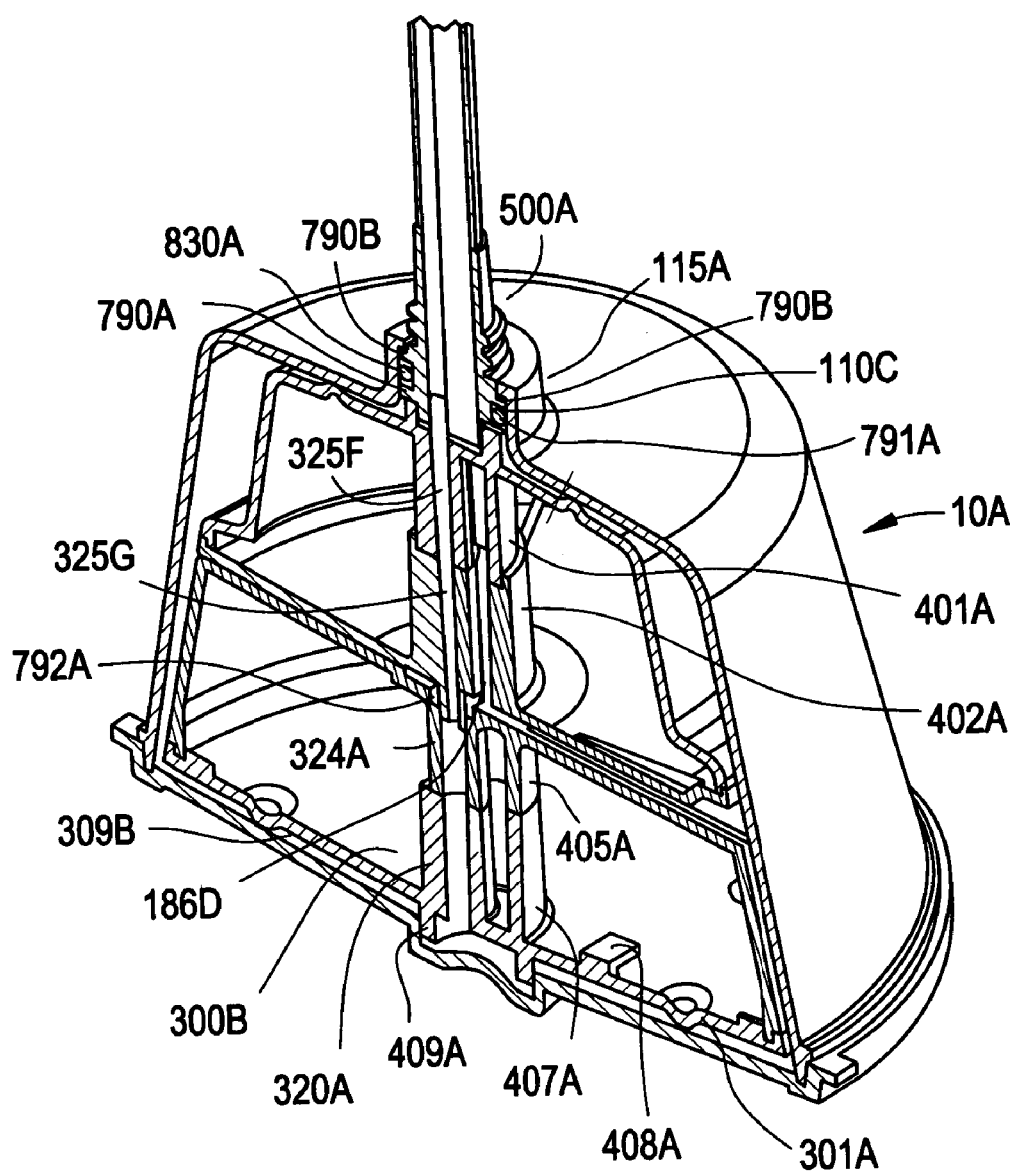
FIG. 53 shows an alternative embodiment of the bowl with the cross-section taken similarly to that shown in FIG. 38.
Figure 54:
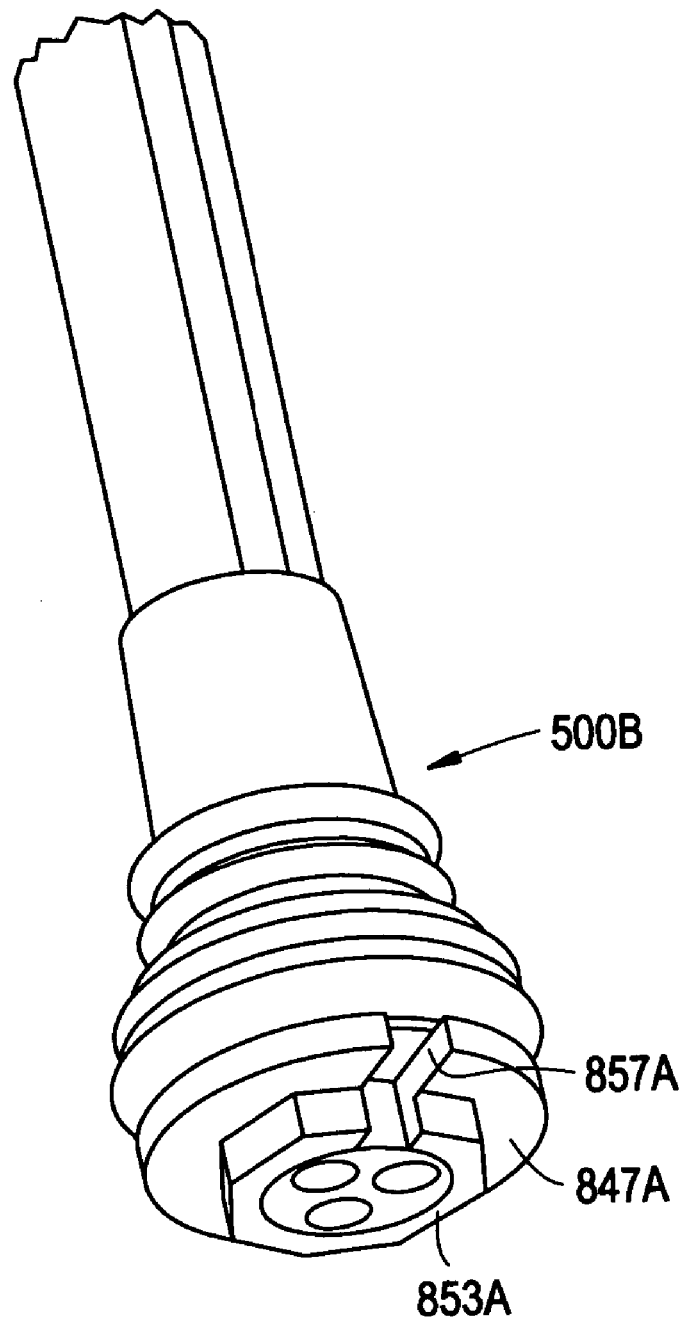
FIG. 54 shows an alternative embodiment of the top core.
Figure 55:
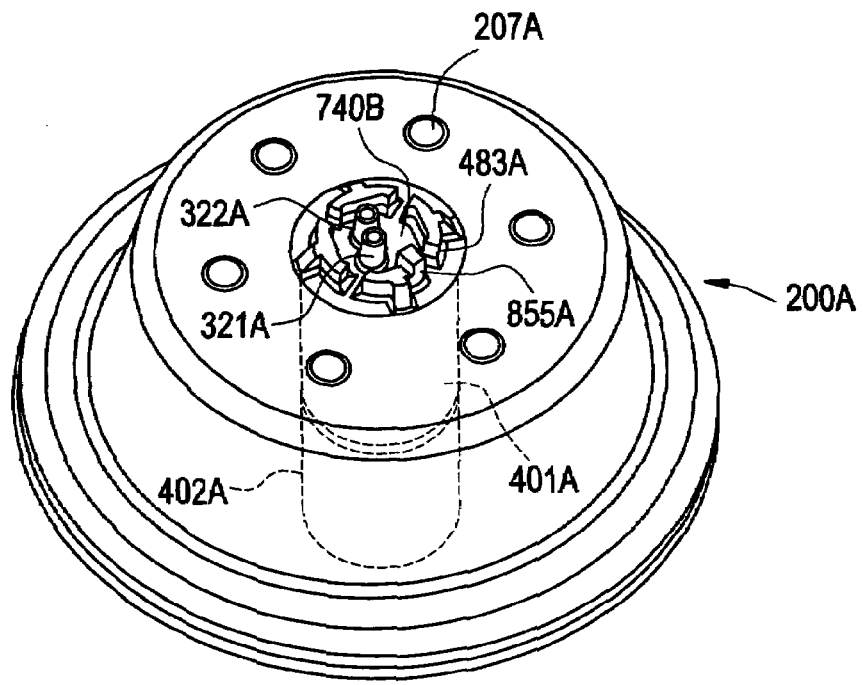
FIG. 55 shows an alternative embodiment of the connection sleeve.

In an alternative embodiment illustrated in FIGS. 53, 54 and 55, conduits 321A and 322A may be affixed to openings 325D and 303B in the top surface 482A of the lumen connector 481A. Additionally, indentations 483A may form a plurality channels in the lumen connector 481A and be adapted to form chamber 740B when connected to connection sleeve 500A or 500B. Chamber 740B is adapted to have one or more surfaces 742A that can mate with the male end 853A of the connection sleeve 500A (male end 853A surrounds end 861 of external conduit 20A). To facilitate the correct orientation of the connection sleeve 500A to the lumen connector 481A the shape of the male end 853A and chamber 740B may be nonsymmetrical or as is illustrated in FIGS. 53, 54 and 55 a guide 855A may be provided which extends from the top surface of the lumen connector 481A and is adapted to fit within opening 857A of the sleeve flange 790A.

Referring back to FIG. 40, the lower core end 295A comprises an upper plate 299A having a top surface 298A, a bottom surface 297A, and an edge 299B that attaches and makes direct contact with lower edge 210D of the outer core wall 210A. The edge 299B of the upper plate 299A is adapted to be joined with lower edge 210D of outer core wall 210A and form a fluid tight seal therewith. Extending perpendicularly from the top surface 298A of upper plate 299A is a channel wall 402A, having an upper end 402B and a lower end 402C and surrounds opening 303A which is substantially in the center of upper plate 299A. A number of fins 403A, attached to the outside surface of channel wall 402A and top surface 298A, supports lumen wall 402A. The channel wall 402A is adapted to mate with channel wall 401A forming a fluid tight seal and providing lumen 400A. First bowl channel 420A is in fluid communications with conduit channel 780A of external conduit 20A through conduit 322A. Opening 303A provides fluid communications from lumen 400A to separation volume 220A as will be further discussed. First bowl channel 420A also surrounds second bowl channel 410A.

Figure 43B:
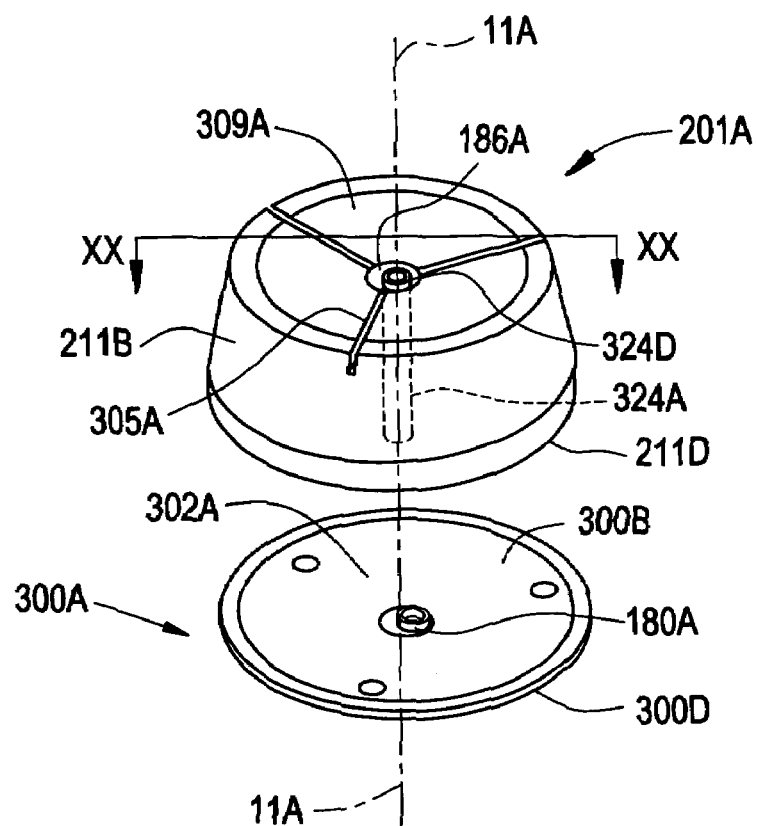
FIG. 43B shows an dimensional cross section view of the bottom core and a lower plate of the bowl of FIG. 43A attached together.
Figure 43A:
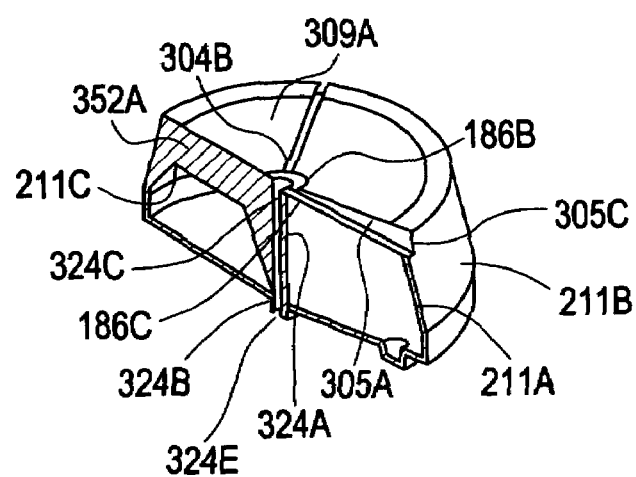
FIG. 43A shows a dimensional exploded view of the bottom core and a lower plate of the bowl of FIG. 37.

Referring to FIGS. 43A, 43B and 44, bottom core 201A comprises an upper core end 206A, a outer core wall 211A and a lower core end 296A. The outer core wall 211A having an outer surface 211B, an inner wall 211C and lower edge 211D. The diameter of bottom core 201A preferably increases from upper core end 206A to lower core end 296A. Bottom core 201A also has a top surface 309A and a bottom surface 309B. Top surface 309A has an indentation 186A (preferably generally circular) substantial in the center of the surface 309A of the upper core end 206A. The indentation 186A has an upper surface 186B and an inner surface 186C. The upper surface 186B of the indentation 186A has therein an opening 324D which extends through to the inner surface 186C. In an alternative embodiment of the present invention illustrated in FIG. 53, the upper surface 186B, may also have a recess a 186D adapted to receive an o-ring and form a fluid type seal around the lower end of 325B of conduit wall 325A. Extending perpendicularly from inner surface 186C around said opening 324D is conduit wall 324A having a distal end 324B. On the top surface 309A extending from the indentation 186A to the outer surface 211B of the outer core wall 211A are one or more channels 305A. The top surface 309A may be horizontal or slope upward or downward from indentation 186A. If top surface 309A slopes upward or downward from indentation 186A to core end 206A, one skilled in the art would be able to adjust the shapes of upper plate 299A and upper core end 295A accordingly. Channels 305A may have an even depth through out the length of the channel 305A. However, channel 305A may slope downward or upward radially from the center. One skilled in the art would see that if top surface 309A slopes upward or downward and channel 305A has a constant depth, then channel 305A slopes upward or downward accordingly.

Referring to FIG. 38, the bottom surface 297A of upper plate 299A is in direct contact with the top surface area 309A of bottom core 201A when completely assembled. This contact forms a fluid tight seal between the two surface areas forming an opening 305B from the indentation 186A to channel 305A. A second opening 305C from channel 305A is formed in the outer surface 211B of outer core wall 211A. The opening 305B provides fluid communications from indentation 186A through channel 305A and opening 305C to separation volume 220A (FIGS. 38 and 40). Thus fluid 800 flows through conduit channel 780A and subsequently passes through first bowl channel 420A. From first bowl channel 420A, fluid 800 then goes to through channel 305A to the separation volume 220A.

Referring to FIGS. 43A and 44, the lower core end 296A has a lower plate 300A, which has a top surface 300B, a bottom surface 300C and outer edge 300D. Extending from the bottom surface 300C of the lower plate 300 are one or more protrusions 301A. The outer edge 300D is adapted to be attached to the lower edge 211D of the outer core wall 211A and provide a fluid tight seal therewith. Positioned above housing floor 180A, lower plate 300A is circular and curves upward radially from its center (illustrated in FIG. 44). Alternatively, lower plate 300A can be flat. As shown in FIG. 38 when positioned above housing floor 180A, a volume 220C exists between lower plate 300A and housing floor 180A. This volume 220C is in fluid communication with separation volume 220A. Lower plate 300A may be made of plastic or any other suitable material. Additionally, extending substantially perpendicularly from the lower surface 300C of lower plate 300A is a conduit 320A. Conduit 320A has a first end 320B that extends into the space 220C between lower plate 300A and housing floor 180A and a second end 320C that extends above the top surface 300B of lower plate 300A. The diameter of conduit 320A is adapted to have a tight fit with conduit wall end 324B. The volume inside conduit walls 324A and 325A comprises a lumen 400B. The volume defined by lower plate 300A, inner surface 211C, and ceiling 253A of bottom core 201A, excluding second bowl channel 410A, may comprise of air or a solid material (See FIGS. 43B and 44).

In an alternative embodiment of the present invention as illustrated in FIG. 53, support walls 405A and 407A may be optionally present. Support wall 405A extends perpendicularly from bottom surface 309B. Support wall 407A extends perpendicularly from the top surface 300B of lower plate 300A and connects with support wall 405A when the bottom core 201A is assembled. Conduit wall 324A may be connected to conduit 320A to form a fluid tight seal and conduits 324A, 320A may be fused respectively with supports walls 405A and 407A. Additionally present extending from the bottom surface 300C of lower plate 300A are one or more orientation spacers 409A that mate within indentation 185A.

As will be readily apparent to one of ordinary skill in the art, the bowl 10A will need to be balanced about center axis 11A. Accordingly, weights may be added as part of the device as is appropriate to facilitate the balancing of the bowl 10A such as weight 408A illustrated in FIG. 53.

Referring to FIG. 38, bowl 10A is adapted so that outer housing 100A, cores 200A and 201A, lower plate 300A and upper plate 299A, housing floor 180A, external conduits 20A and connection sleeve 500A, and lumens 400A and 400B are in connection and rotate together. Housing floor 180A of outer housing 100A comprises recesses 181A on its top surface and these recesses are shaped to fit protrusion 301A of lower plate 300A. As shown, lower plate 300A has round protrusion 301A on its bottom surface 300C to restrict movement of lower plate 300A with respect to housing floor 180A. When assembled, each single protrusion 301A on the bottom surface of lower plate 300A forms a tight fit with recess 181A on housing floor 180A. Thus, when outer housing 100A is rotated, external conduit 20A and connection sleeve 500A, top core 200A, upper plate 299A, bottom core 201A, lower plate 300A, housing floor 180A, and lumens 400A and 400B will rotate therewith.

As illustrated in FIG. 38 lumen 400A allows whole blood 800 to come into bowl 10A via a first bowl channel 420A. First bowl channel 420A provides a passageway for inflow of fluid 800 through lumen 400A to indention 186A and then to the separation volume 220A through channel 305A. Lumen 400A is located inside top core 200A. Lumen 400A has a height from upper lumen end 480A and lower lumen end 402C. Lumen 400A is formed by the connection of channel wall 401A extending from the inner surface 481C of lumen connector 481A and channel wall 402A extending from the top surface 298A of upper plate 299A. Channel wall 401A is supported by a plurality of fins 251A which are attached to the inner wall surface 210C of the outer core wall 210A and inner surface 205C of the upper core end 205A, and channel wall 402A is supported by a plurality of fins 403A (FIG. 40). It can readily be seen that height of lumen 400A can be adjusted by changing the sizes and shapes of core 200A, channel wall 401A, channel wall 402A, conduit wall 325A, and the height of conduit wall 324A.

As illustrated in FIG. 38, lumen 400A, from upper lumen end 480A to lower lumen end 402C, encloses an inner lumen 400B. Lower lumen end 402C has an opening 303A which is in fluid communication with separation volume 220A through a number of channel 305A. In the illustrated embodiment lumen 400A comprises first bowl channel 420A. Second bowl channel 410A is located inside first bowl channel 420A of the top core 200A and is enclosed therein from lumen end 480A and to lumen 402C. Furthermore, second bowl channel 410A forms a passageway through lumen 400B from below lower plate 300A for the removal of a first separated fluid component 810 that gathers in indentation 185A of housing floor 180A. Second bowl channel 410A extends from housing floor 180A of outer housing 100A through lumen 400B and to conduit channel 760A of external conduit 20A.

Referring FIG. 38 (shown without conduit 321C), inner lumen 400B allows red blood cells 810 to exit bowl 10A via a second bowl channel 410A that provides fluid communication from the housing floor above indentation 185A to opening 324E. Inner lumen 400B has an upper conduit end 325C and a lower conduit end 324B and comprises two conduit walls 324A and 325A which are connected in a fluid tight manner and form second bowl channel 410A that has a smaller diameter than and is separate and distinct from first bowl channel 420A. Conduit wall 325A is supported by a fin 251A that extends through channel wall 401A and attaches to conduit wall 325A. Unlike lumen 400A which has one end near indentation 186A, lumen 400B extends beyond indentation 186A and through bottom plate 300A. The first conduit wall 325A has an upper end 325C which has an opening 325D on the top surface 482A of lumen connector 481A and a lower end 325B having an opening 325E adapted to fit tightly with upper end 324C of conduit wall 324A. Upper end 324C of conduit wall 324A is higher than indentation 186A and has an opening 324D. Conduit wall 324A also has end lower end 324B and is supported by a plurality of fins 252A. Lower end 324B having opening 325E is adapted to connect to conduit 320A having opening 302A located near the center of lower plate 300A. The connection of openings 325E and 302A provide fluid communication between lumen 400B and the space 220C between lower plate 300A and housing floor 180A. The space 220C between lower plate 300A and housing floor 180A in turn has fluid communication with separation volume 220A.

Conduit 320A provides a tight fit with lower end 324B, providing support for second bowl channel 410A. Each bowl channel 420A and 410A may be made of any type of flexible or rigid tubing (such as medical tubing) or other such device providing a sealed passageway, possibly for pressurized or unpressurized fluid flow, and which preferably can be disposable and sterilizable, i.e., of simple and efficient manufacture.

Drive Tube

As illustrated in FIGS. 39A and 39B, conduit assembly 860A is attached to bowl 10A via connection sleeve 500A which is attached onto the first end 861A of external conduit 20A having a first conduit channel 780A, a second conduit channel 760A, and a third conduit channel 770A. Each conduit channel has fluid communication with a first bowl channel 420A, a second bowl channel 410A, and a bowl chamber 740A. The three conduit channels are equally spaced 120° apart and equal in diameter in external conduit 20A (See FIG. 50). When fluidly connect to external conduit 20A and bowl 10A, conduit channel 780A is fluidly connected with first bowl channel 420A for inflowing fluid 800 from external conduit 20A into bowl 10A for separation. Similarly, second conduit channel 760A fluidly connects to second bowl channel 410A for removing first separated fluid component 810 from bowl 10A into external conduit 20A. Finally, third conduit channel 770A connects to bowl chamber 740A for removing second separated fluid component 820 from bowl 10A.

Figure 45:
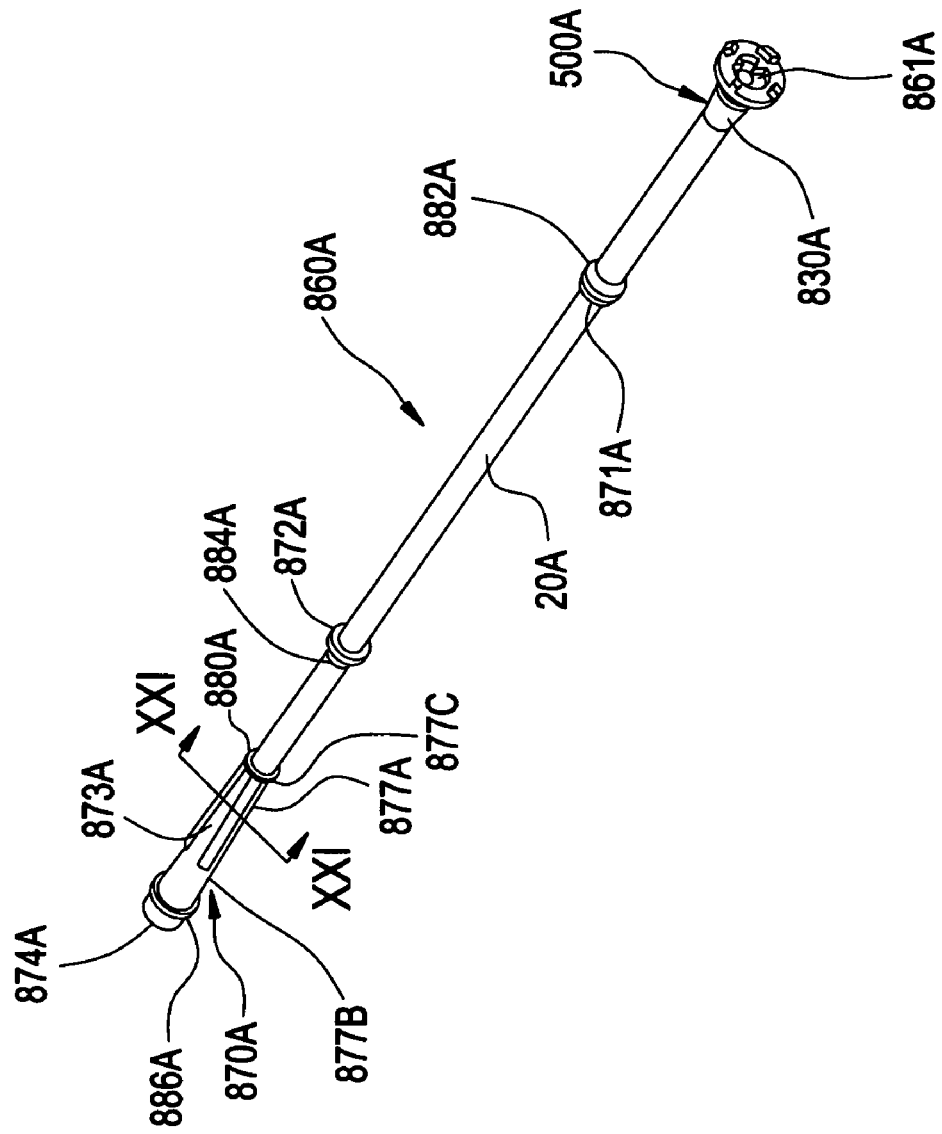
FIG. 45 shows a dimensional view of another embodiment of a conduit assembly.

As is illustrated in FIG. 45, external conduit 20A has a connection sleeve 500A on the first end 861A and an anchor sleeve 870A on the second end 862A of external conduit 20A. Optionally present between the connection sleeve 500A and the anchor sleeve 870A on external conduit 20A are a first shoulder 882 and a second shoulder 884 which extend perpendicularly from the external conduit 20A and are of a larger diameter. Between the connection sleeve 500A and anchor sleeve 870A (or if present the first and second shoulder 882, 884) are a first and second bearing rings 871A and 872A. External conduit 20A, anchor sleeve 870A, and connection sleeve may be prepared from the same or different biocompatible materials of suitable strength and flexibility for use in this type of tubing in a centrifuge (one such preferred material is HYTREL®). The connection sleeve 500A and the anchor sleeve 870A may be attached through any suitable means such as adhesives, welding etc., however, for ease of manufacture it is preferred that the connection sleeve 500A and the anchor sleeve 870A be overmolded to the external conduit 20A.

Figure 48:
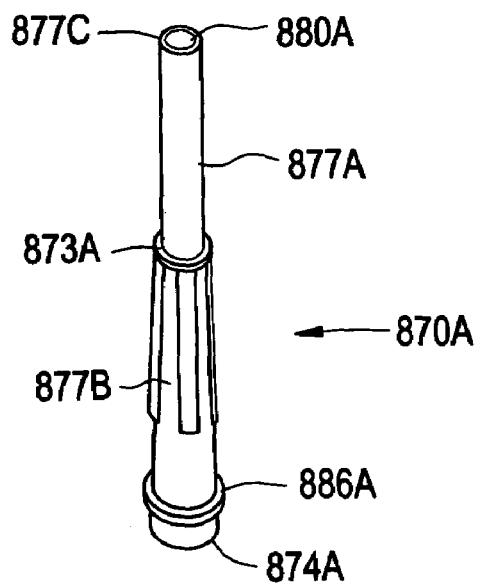
FIG. 48 shows a dimensional view of an anchor end of the present invention.
Figure 49:
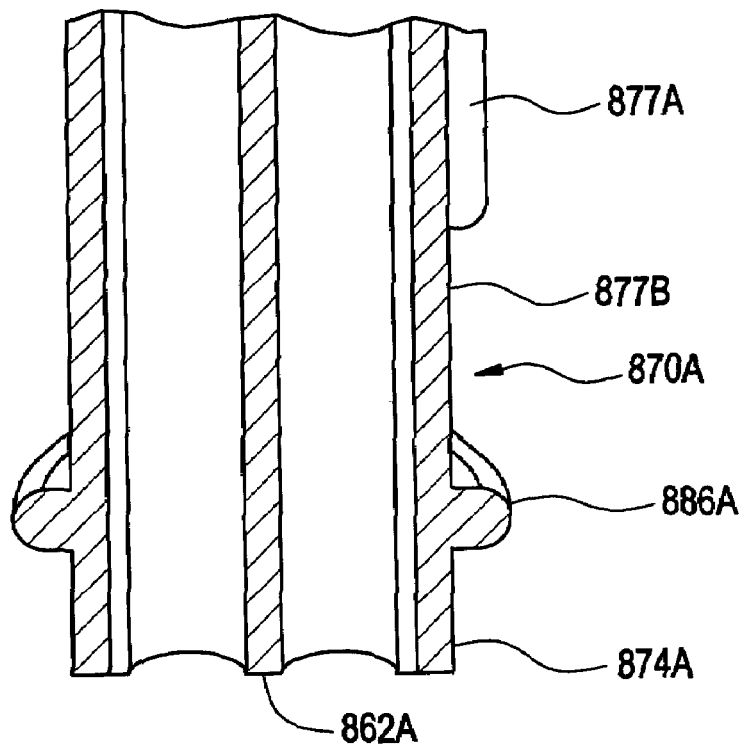
FIG. 49 shows a lateral cross-sectional view of an anchor end.
Figure 50:
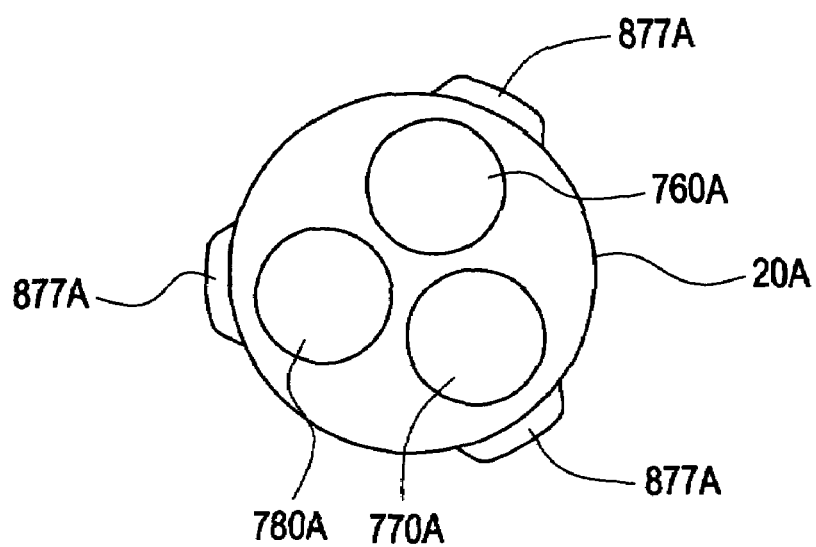
FIG. 50 shows a horizontal cross-sectional view of an anchor end taken along line XXI.

Referring to FIGS. 45, 48 and 49 anchor sleeve 870A comprises a body 877B having a first anchor end 873A and second anchor end 874A. Anchor sleeve 870A is attached to second conduit end 862A of external conduit 20A (preferably by overmolding) and increases in diameter from first collar 873A to the collar 874A. Spaced distally from second end 874A is a collar 886A, which extends perpendicularly from body 877B and of a larger diameter than the body 877B of the anchor sleeve 870A. A plurality of ribs 877A having a first rib end 877B between the collar 886A and second anchor end 873A and a second rib end 877C extending beyond the first anchor end 873A are attached to the body 877B. The second rib ends 877C are joined together by a ring 880A, which is also attached to external conduit 20A. The ribs 877A run parallel to the external conduit 20A and are preferably placed over the region where conduit channels 760A, 770A, and 780A, are closest to the surface of the external conduit 20A (FIG. 50). The regions where the conduit channels 760A, 770A and 780A are closest to the outside diameter of external conduit 20A unless reinforced tend to fail during high speed rotation. Having ribs parallel with the conduit channels beyond the anchor sleeve end 873A provides reinforcement to this region and prevents conduit failure at high speed rotation. In one aspect, the ribs prevent the buckling of the external conduit 20A in this region and act as structural elements to transfer the torsional stress to the anchor sleeve 870A.

Figure 46:
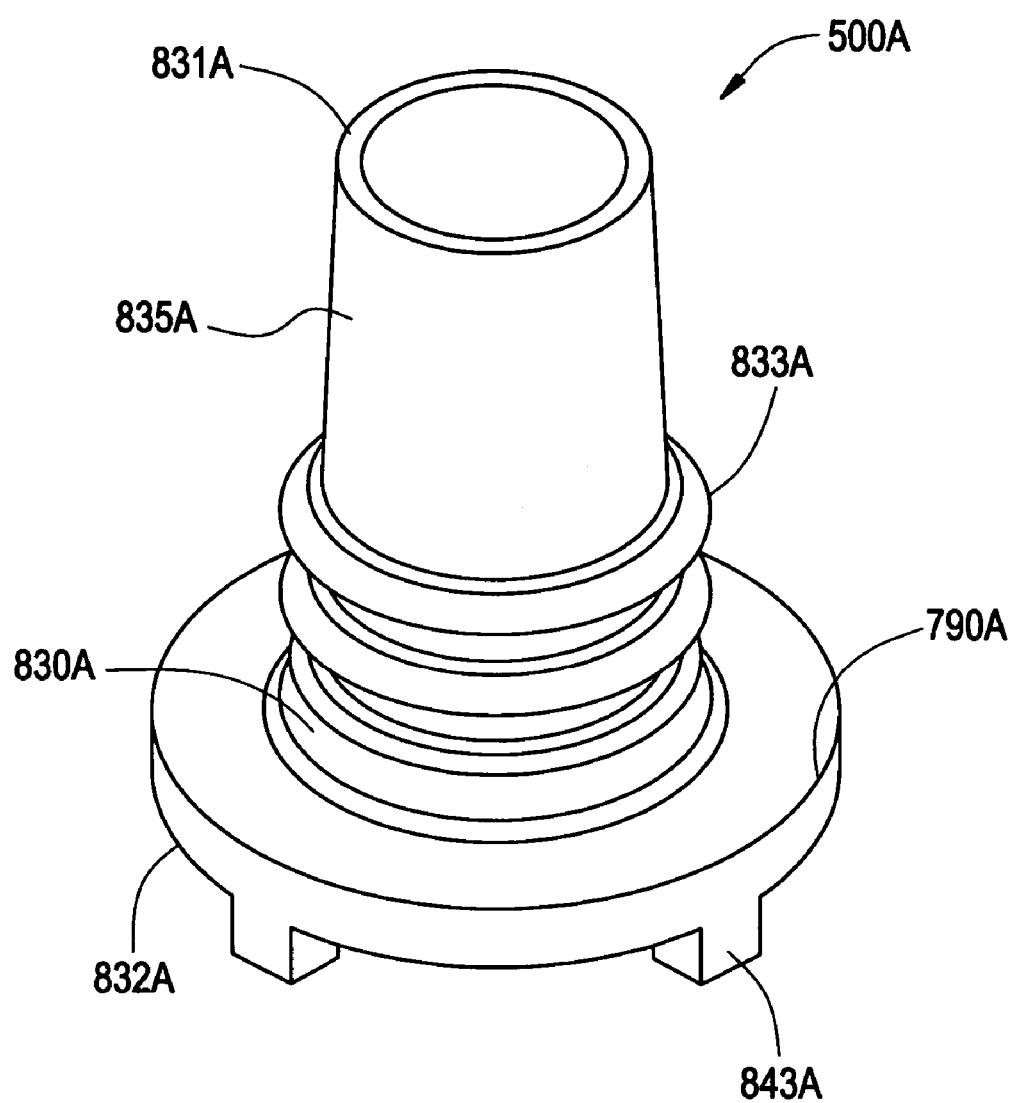
FIG. 46 shows a dimensional view of the connection sleeve of FIG. 45.
Figure 47:
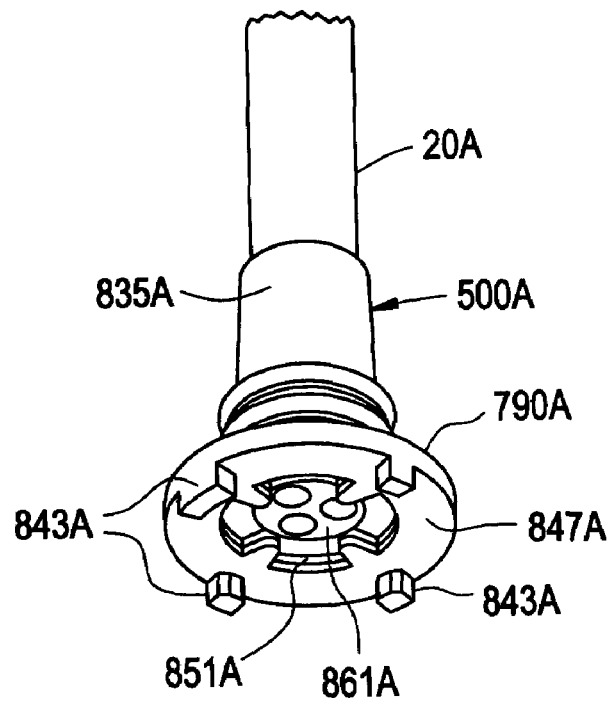
FIG. 47 shows a dimensional view of one end of conduit assembly of FIG. 45.

Connection sleeve 500A comprises body 830A having an upper sleeve end 831A and lower sleeve end 832A (FIGS. 46 and 47). Lower sleeve end 832A has sleeve flange 790A and a plurality of protrusions 843A, which are sized to engage indentations 484A on the wall surface 482A of lumen connector 481A. When the bowl 10A is assembled, a fluid tight seal may be provided by placing o-ring 791A around body 830A and compressing the o-ring 791A between flange 790A and housing 100A. Upper sleeve end 831A is adapted to be secured to external conduit 20A. Referring to FIG. 46, 39A and 39B, connection sleeve 500A is secured to bowl 10A by means of sleeve flange 790A and is adapted to fluidly connect conduit channels 780A, 760A, 770A of external conduit 20A to bowl channels 420A and 410A, and chamber 740A of bowl 10A. When assembled, connection sleeve 500A is mounted to lumen connector 481A (FIGS. 39A and 39B).

Connection sleeve 500A preferably increases in diameter from upper sleeve end 831A to lower sleeve end 832A and is overmolded to first conduit end 861A of external conduit 20A. Connection sleeve 500A connects bowl 10A to external conduit 20A without use of a rotatable seal, which would otherwise normally be located between bowl 10A and connection sleeve 500A. The seal-less connection between bowl 10A and connection sleeve 500A may occur as explained above or alternatively through use of, for example, an O-ring, a groove, or lip, grommet-type connection, welding, or a tight fit with or without adhesive in either bowl 10A or connection sleeve 500A.

As illustrated in FIGS. 46 and 39B, sleeve flange 790A has a bottom surface 847A that contacts with top surface 482A of lumen connector 481A forming a tight seal. However, lumen connector 481A has a plurality of indentation 483A that provides for fluid communication between separation chamber 220A and bowl chamber 740A, which, in turn has fluid communication with conduit channel 770A. Bowl chamber 740A is defined by lumen mounting recess 851A and top surface 482A of lumen connector 481A, excluding the space occupied by hollow cylinders 321A and 322A. A plurality of protrusions 843A on the bottom surface 847A of sleeve flange 790A engages and slides into indentations 484A on the wall surface 482B of lumen connector 481A, thus providing a tight fit.

Connection sleeve 500A helps to secure external conduit 20A to bowl 10A, thus fluidly connecting external conduit 20A to bowl 10A. This fluid connection enables fluid 800 to be supplied through external conduit 20A to bowl 10A. Similarly, this fluid connection also enables separated fluid components b, 820 to be removed from bowl 10A through external conduit 20A.

External conduit 20A has an approximately constant diameter which helps to reduce the rigidity. An excessively rigid external conduit 20A will heat up and fail more quickly. Additionally, a constant diameter conduit is cheap/easy to manufacture, allows easy experimentation with connection sleeve 500A and anchor sleeve 870A sizes, and allows bearing rings 871A, 872A to be easily slid thereon. Preferably the movement of bearings 871A and 872A will be constrained by first and second shoulders 882A and 884A. External conduit 20A may be made of any type of flexible tubing (such as medical tubing) or other such device providing a sealed passageway for the flow of fluids, which may be pressurized, into or out of a reservoir of any sort, and which preferably can be disposable and sterilizable.

Permanent Tower System

FIG. 17 illustrates tower system 2000. Tower system 2000 is the permanent (i.e., non-disposable) piece of hardware that receives the various devices of photopheresis kit 1000, such as, cassette 1100, irradiation chamber 700, and centrifuge bowl 10 (FIG. 1). Tower system 2000 performs the valving, pumping, and overall control and drive of fluid flow through disposable photopheresis kit 1000. Tower system 2000 performs all of the necessary control function automatically through the use of a properly programmed controller, for example a processor or IC circuit, coupled to all of the necessary components. While a new disposable kit must be discarded after each photopheresis therapy session, tower system 2000 is used over and over again. Tower system 2000 can be modified to perform a number of extracorporeal blood circuit treatments, for example apheresis, by properly programming the controller or by changing some of its components.

Tower system 2000 has a housing having an upper portion 2100 and a base portion 2200. Base portion 2200 has a top 2201 and a bottom 2202. Wheels 2203 are provided at or near the bottom 2202 of base portion 2200 so that tower system 2000 is mobile and can easily be moved from room to room in a hospital setting. Preferably, the front wheels 2203 are pivotable about a vertical axis to allow ease in steering and maneuvering tower system 2000. Top 2201 of base portion 2200 has a top surface 2204 having control deck 1200, best illustrated in FIG. 22, built therein (see FIG. 22). In FIG. 17, cassette 1100 is loaded onto control deck 1200. Base portion 2200 also has hooks (not illustrated), or other connectors, to hang plasma collection bag 51 and treatment bag 50 therefrom. Such hooks can be located anywhere on tower system 2000 so long as their positioning does not interfere with the functioning of the system during therapy. Base portion 2200 has photoactivation chamber 750 (FIG. 18) located behind door 751. Additional hooks (not illustrated) are provided on tower system 2000 for hanging saline and anticoagulant bags. Preferably, these hooks are located on upper portion 2100.

Photoactivation chamber 750 (FIG. 18) is provided in base portion 2200 of tower system 2000 between top 2201 and bottom 2202 behind door 751. Door 751 is hingedly connected to base portion 2200 and is provided for access to photoactivation chamber 750 and to allow the operator to close photoactivation chamber 750 so that UV light does not escape into the surrounding during treatment. Recess 752 is provided to allow tubes 1112, 1117 (FIG. 1) to pass into photoactivation chamber 750 when irradiation chamber 700 is loaded and when door 751 is closed. The photoactivation chamber is discussed in detail below with respect to FIGS. 16 and 18.

Upper portion 2100 is located atop base portion 2200. Centrifuge chamber 2101 (FIG. 19) is located in upper portion 2100 behind centrifuge chamber door 2102. Centrifuge chamber door 2102 has a window 2103 so an operator can see in centrifuge chamber 2101 and monitor for any problems. Window 2103 is constructed with glass thick enough to withstand any forces that may be exerted on it from an accident during centrifugation which can rotate the centrifuge bowl at speeds greater than 4800 RPMs. Preferably, window 2103 is constructed of shatter-proof glass. Door 2102 is hingedly connected to upper portion 2100 and has an automatic locking mechanism that is activated by the system controller during system operation. Centrifuge chamber 2101 is discussed below in more detail with respect to FIG. 19.

Preferably, deck 1200 is located on top surface 2204 of base portion 2200 at or near the front of system tower 2000 while upper portion 2100 is extending upward from base portion 2200 near the rear of tower system 2000. This allows the operator easy access to control deck 1200 while simultaneously affording the operator access to centrifuge chamber 2101. By designing tower system 2000 to have the centrifuge chamber 2101 in the upper portion 2100 and having the photoactivation chamber 750 and deck 1200 in base portion 2200, an upright configuration is achieved. As such, system tower 2000 has a reduced footprint size and takes up a reduced amount of valuable hospital floor space. The height of system tower 2000 remains below sixty inches so that one view is not obstructed when transporting the machine around the hospital form the rear. Additionally, having deck 1200 in a fairly horizontal position will provide the operator with a place to set devices of photopheresis kit 1000 during the loading of other devices, facilitating easy loading. Tower system 2000 is robust enough to withstand forces and vibrations brought on by the centrifugation process.

A monitor 2104 is provided on centrifuge chamber door 2102 above window 2103. Monitor 2104 has a display area 2105 for visually displaying data to an operator, such as, for example, user interfaces for data entry, loading instructions, graphics, warnings, alerts, therapy data, or therapy progress. Monitor 2104 is coupled to and controlled by the system controller. A data card receiving port 2001 is provided on a side of monitor 2104. Data card receiving port 2001 is provided to slidably receive data card 1195 which is supplied with each disposable photopheresis kit 1000 (FIG. 1). As mentioned above, data card 1195 can be pre-programmed to store serve a variety of data to supply to the system controller of tower system 2000. For example, data card 1195 can be programmed to relay information so that the system controller can ensure: (1) that the disposable photopheresis kit is compatible with the blood drive equipment into which it is being loaded; (2) that the photopheresis kit is capable of running the desired treatment process; (3) that the disposable photopheresis kit is of a certain brand name or make. Data card receiving port 2001 has the necessary hardware and circuitry to both read data from, and write data to, data card 1195. Preferably, data card receiving port 2201 will record treatment therapy data to data card 1195. Such information can include for example, collection times, collection volumes, treatment times, volumetric flow rates, any alarms, malfunctions, disturbances in the process, or any other desired data. While data card receiving port 2001 is provided on monitor 2104, it can be located anywhere on tower system 2000 so long as it is coupled to the system controller or other appropriate control means.

Photoactivation Chamber for Receiving Irradiation Chamber

Referring now to FIGS. 16 and 18, photoactivation chamber 750 is illustrated in cross section. Photoactivation chamber 750 is formed by housing 756. Housing 756 fits within base portion 2200 of tower system 2000 behind door 751 (FIG. 17). Photoactivation chamber 750 has a plurality of electrical connection ports 753 provided on back wall 754. Electrical connection ports 753 are electrically coupled to a source of electrical energy. Photoactivation chamber 750 is designed to receive UVA light assembly 759 (FIG. 16). When fully loaded into photoactivation chamber 750, electrical contacts (not illustrated) located on contact wall 755 of UVA light assembly 759 form an electrical connection with electrical connection ports 753. This electrical connection allows electrical energy to be supplied to UVA lamps 758 so that they can be activated. Preferably, three electrical connection ports are provided for each set of UVA lamps 758. More preferably, UVA light assembly 759 has two sets of UVA lamps 758 forming a space which irradiation chamber 700 can be inserted. The supply of electrical energy to UVA lamps 758 is controlled by the properly programmed system controller using a switch. UVA lamps 758 are activated and deactivated as necessary by the controller during the photopheresis therapy session.

Vent hole 757 is provided in the top of housing 756 near back wall 754 of photoactivation chamber 750. Vent hole 757 connects to vent duct 760 which leads out of the back of tower system 2000. When heat generated by UVA lamps 758 builds up in photoactivation chamber 750 during a treatment therapy, this heat escapes photoactivation chamber 750 via vent hole 757 and vent duct 760. The heat exits tower system 2000 through tower housing hole 761 located in the rear of tower system 2000, away from the patient and the operator.

Figure 20:
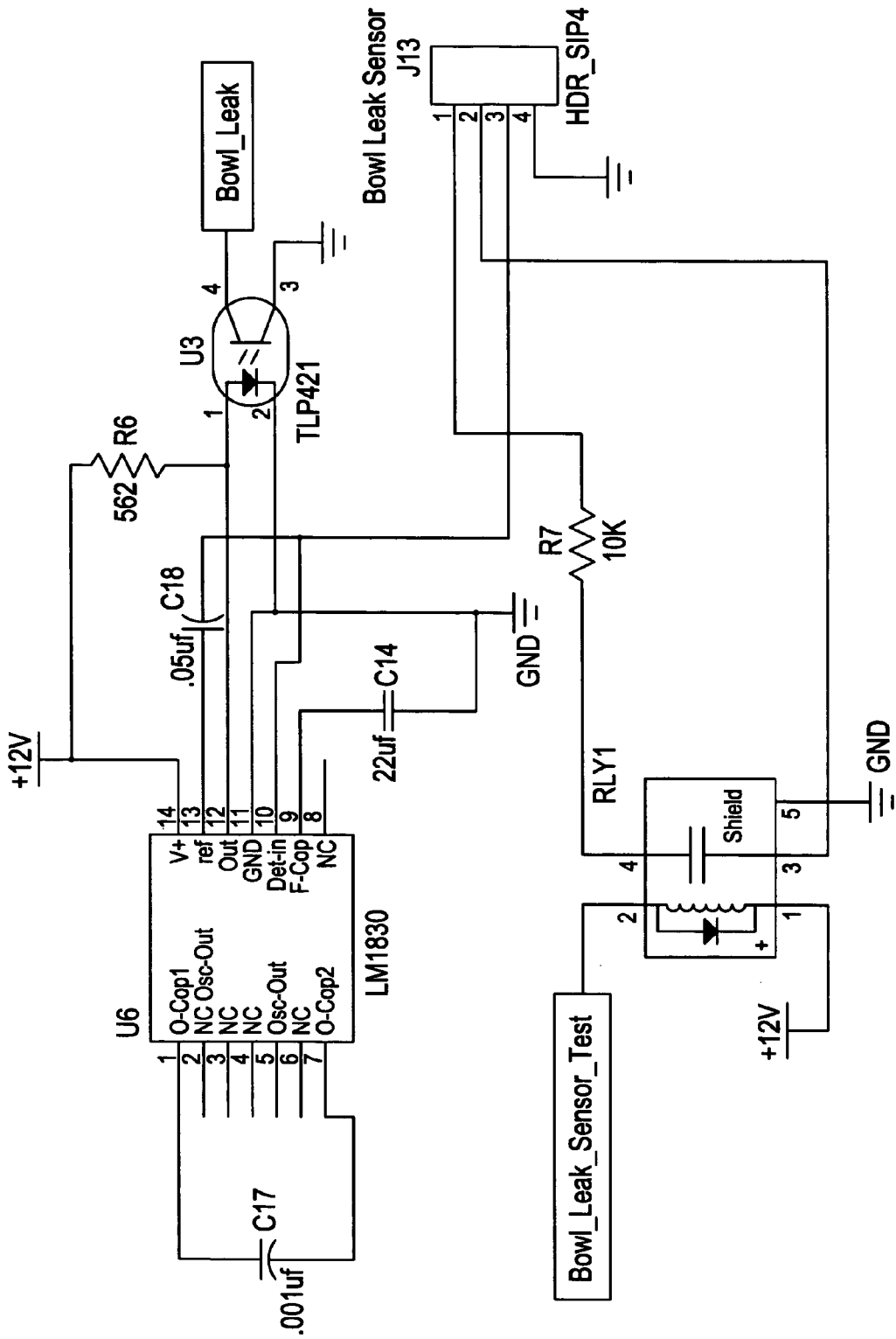
FIG. 20 is an electrical schematic of the leak detection circuit provided in the photoactivation chamber of FIG. 18.

Photoactivation chamber 750 further comprises tract 762 for receiving irradiation chamber 700 and holding irradiation in an upright position between UVA lamps 758. Tract 762 is at or near the bottom of photoactivation chamber 750. Preferably, a leak detector circuit 763 is provided below tract 762 to detect any fluid leaks irradiation chamber 700 during, before, or after operation. Leak detector circuit 762 has two electrodes patterned in a U shape located on an adhesive backed flex circuit. The electrodes are designed to allow for application of a short circuit to test for discontinuities. One end of each electrode goes to an integrated circuit while the other end of each electrode is tied to a solid-state switch. The solid-state switch can be used to check for continuity of the electrodes. By closing the switch the electrodes are shorted to one another. The integrated circuit then detects the short. Closing the switch causes a situation equivalent to the electrodes getting wet (i.e., a leak). IN If the electrodes are damaged in any way, the continuity check will fail. This is a positive indication that the electrodes are not damaged. This test can be performed each time at system start-up or periodically during normal operation to ensure that leak detection circuit 762 is working properly. Leak detection circuit 762 helps ensure that leaks do not go unnoticed during an entire therapy session because the leak detection circuit is damaged. An electrical schematic of leak detector circuit 762 is provided in FIG. 20.

Centrifuge Chamber

Figure 19:
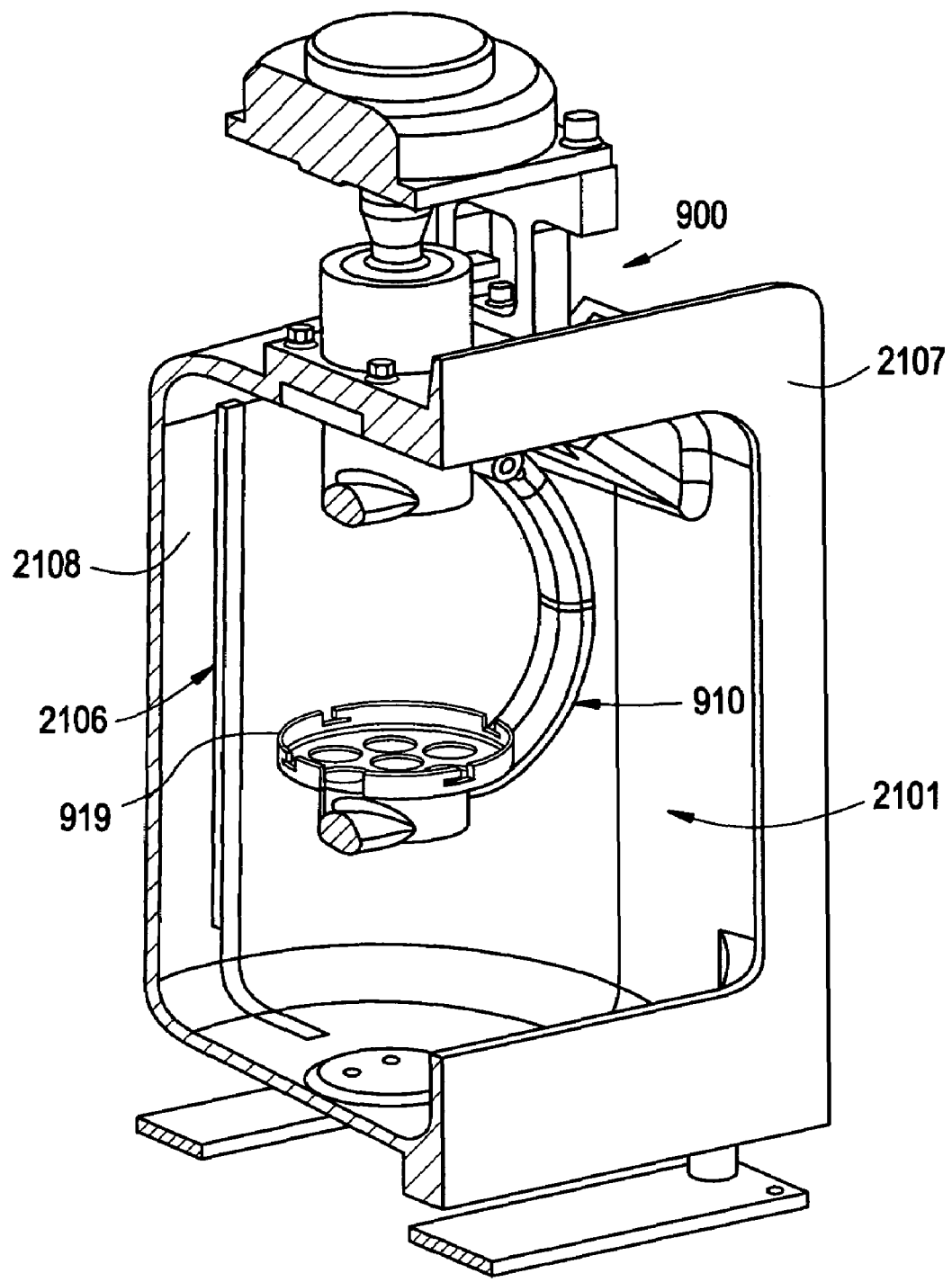
FIG. 19 is a cross-sectional view of an embodiment of the centrifuge chamber used in the tower system of FIG. 17.

FIG. 19 illustrates centrifuge chamber 2101 in cross section with the housing of tower system 2000 removed. Rotational device 900 (also in cross-section) capable of utilizing 1-omega 2-omega spin technology is positioned within centrifuge chamber 2101. Rotational device 900 includes a rotating bracket 910 and a bowl holding plate 919 for rotatably securing centrifuge bowl 10 (FIG. 1). Housing 2107 of centrifuge chamber 2101 is preferably made of aluminum or some other lightweight, sturdy metal. Alternatively, other rotational systems may be used within tower system 2000 such as that described in U.S. Pat. No. 3,986,442, which is expressly incorporated herein by reference in its entirety.

Figure 21:
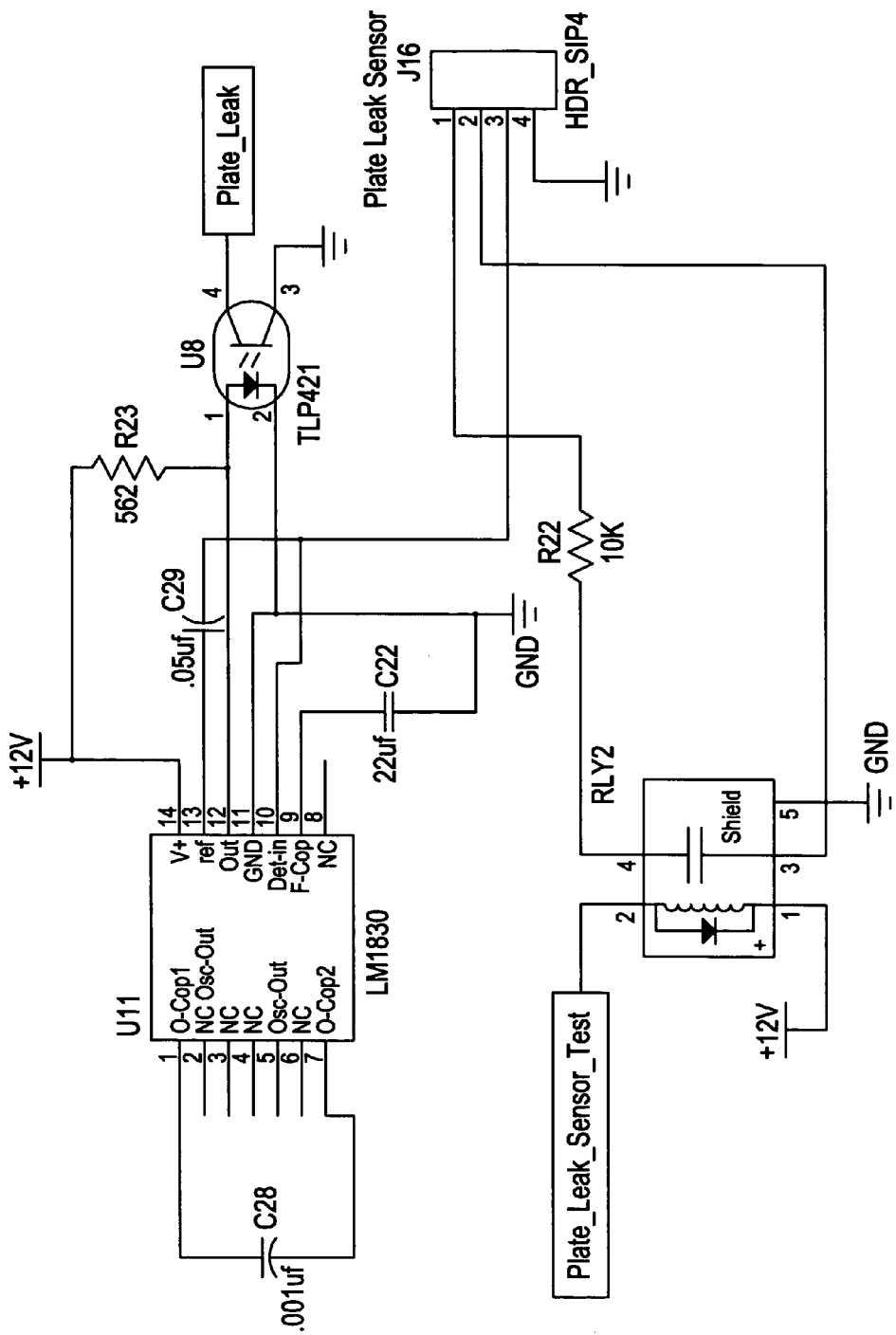
FIG. 21 is an electrical schematic of the leak detection circuit provided in the centrifuge chamber of FIG. 19.

Leak detection circuit 2106 is provided on back wall 2108 of housing 2107. Leak detection circuit 2106 is provided to detect any leaks within centrifuge bowl 10 or the connecting tubes during processing. Leak detection circuit 2106 is identical to leak detector circuit 762 described above. An electrical schematic of leak detection circuit 2106 is provided in FIG. 21.

Fluid Flow Control Deck

FIG. 22 illustrates control deck 1200 of tower system 2000 (FIG. 17) without a cassette 1100 loaded thereon. Control deck 1200 performs the valving and pumping so as to drive and control fluid flow throughout photopheresis kit 1000. Preferably, deck 1200 is a separate plate 1202 that is secured to base portion 2200 of tower system 2000 via screws or other securing means, such as, for example, bolts, nuts, or clamps. Plate 1202 can be made of steel, aluminum, or other durable metal or material.

Deck 1200 has five peristaltic pumps, whole blood pump 1301, return pump 1302, recirculation pump 1303, anticoagulant pump 1304, and red blood cell pump 1305 extending through plate 1202. Pumps 1301-1305 are arranged on plate 1202 so that when cassette 1100 is loaded onto deck 1200 for operation, pump loop tubes 1120-1124 extend over and around pumps 1301-1305 (FIG. 25).

Air bubble sensor assembly 1204 and HCT sensor assembly 1205 are provided on plate 1202. Air bubble sensor assembly 1204 has three trenches 1206 for receiving tubes 1114, 1106, and 1119 (FIG. 25). Air bubble sensor assembly 1204 uses ultrasonic energy to monitor tubes 1114, 1106, and 1119 for differences in density that would indicate the presence of air in the liquid fluids normally passing therethrough. Tubes 1114, 1106, and 1119 are monitored because these lines go to the patient. Air bubble sensor assembly 1204 is operably coupled and transmits data to the system controller for analysis. If an air bubble is detected, the system controller will shut down operation and prohibit fluid flow into the patient by occluding tubes 1114, 1106, and 1109 by moving compression actuators 1240-1242 to a raised position, thereby compressing tubes 1114, 1106, and 1119 against cassette 1100 as discussed above and/or shutting down the appropriate pump. HCT sensor assembly 1205 has trench 1207 for receiving HCT component 1125 of tube 1116. HCT sensor assembly 1205 monitors tube 1116 for the presence of red blood cells by using a photoelectric sensor. HCT sensor assembly 1205 is also operably coupled to and transmits data to the system controller. Upon HCT sensor assembly 1205 detecting the presence of red blood cells in tube 1116, the system controller will take the appropriate action, such as stopping the appropriate pump or activating one of compression actuators 1243-1247, to stop fluid flow through tube 1116.

Deck 1200 also has five compression actuators 1243-1247 and three compression actuators 1240-1242 strategically positioned on plate 1202 so that when cassette 1100 is loaded onto deck 1200 for operation, each of compression actuators 1240-1247 are aligned with corresponding apertures 1137 and 1157. Compression actuators 1240-1247 can be moved between a lowered position and a raised position. As illustrated in FIG. 22, compression actuators 1243-1247 are in the lowered position and compression actuators 1240-1242 are in the raised position. When in a raised position, and when cassette 1100 is loaded onto deck 1200 as illustrated in FIG. 25, compression actuators 1240-1247 will extend through the corresponding apertures 1137 or 1157 and compress the portion of flexible tubing that is aligned with that aperture, thereby pinching the flexible tube shut so that fluid can not pass. When in the lowered position, compression actuators 1240-1247 do not extend through apertures 1137 and 1157 and thus do compress the flexible tubing.

Compression actuators 1243-1247 are spring retracted so that their default position is to move to the lowered position unless activated. Compression actuators 1243-1247 are independently controlled and can be raised r lowered independent of one another. Compression actuators 1240-1242 on the other hand are coupled together. As such, when one compression actuator 1240-1242 is lowered or raised, the other two compression actuators 1240-1242 are also lowered in raised accordingly. Additionally, compression actuators 1240-1242 are spring loaded so that their default position is to move to the raised position. Thus, if the system loses power during a therapy session, compression actuators 1240-1242 will automatically move to the raised position, occluding tubes 1114, 1106, and 1119 and preventing fluids from entering or leaving the patient.

Figure 23:
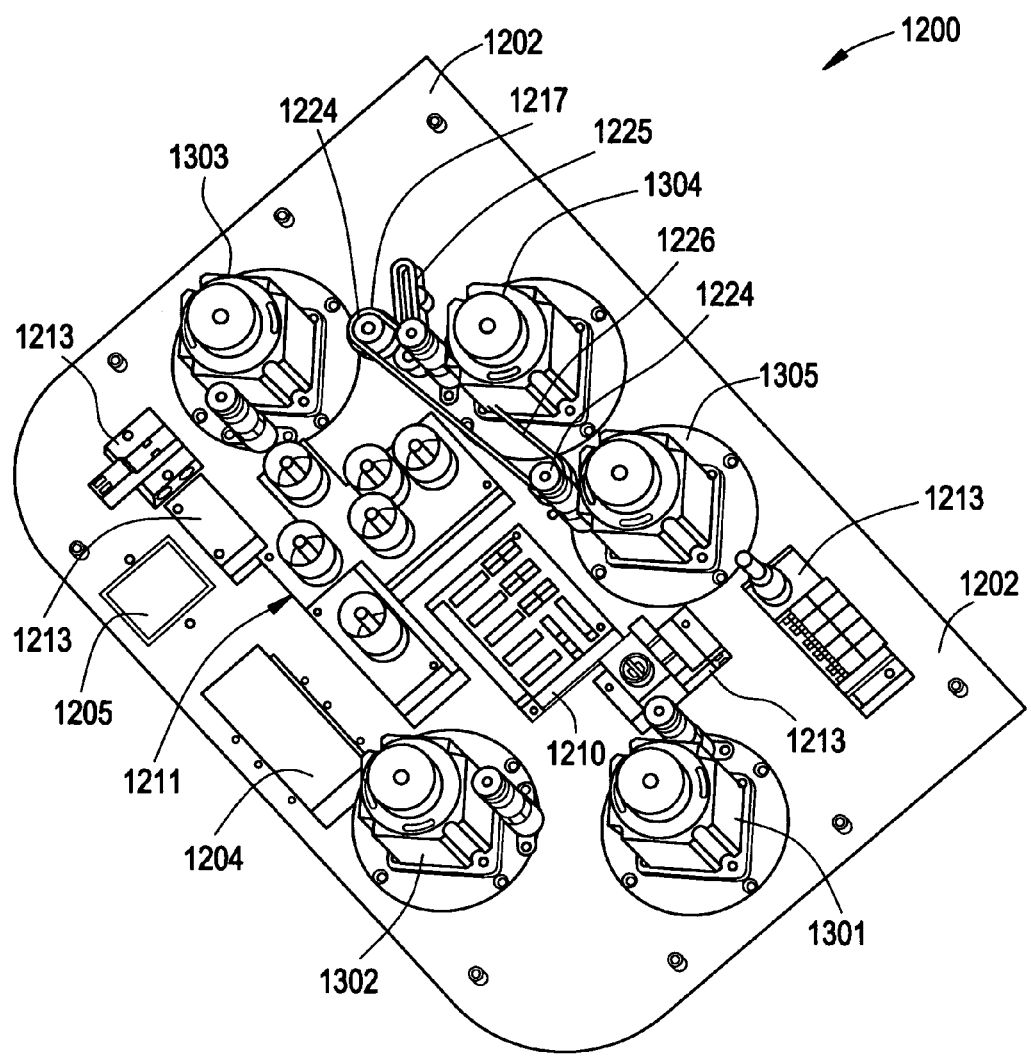
FIG. 23 is a perspective bottom view of the control deck of FIG. 22.
Figure 24:
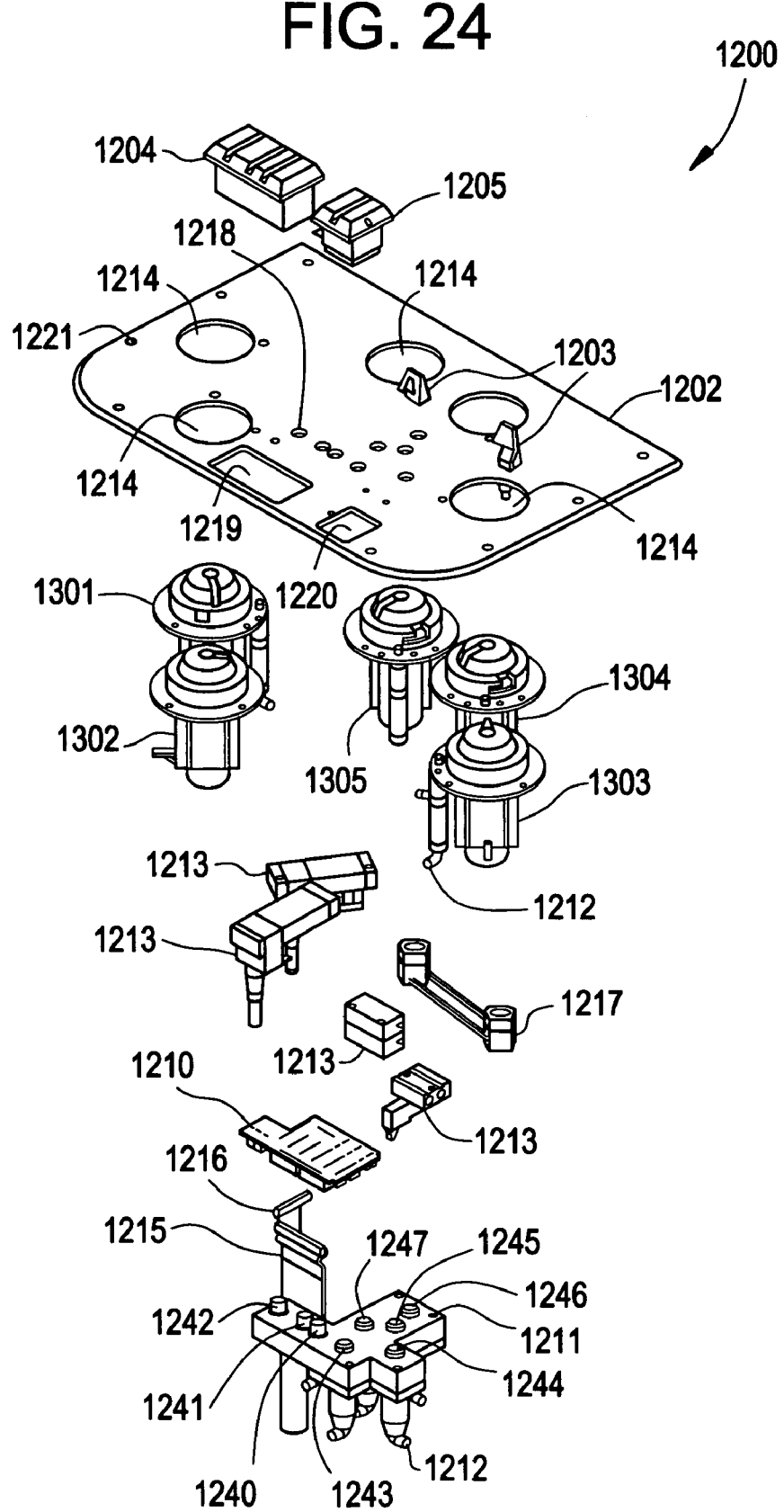
FIG. 24 is an exploded view of the control deck of FIG. 22.

Referring now to FIGS. 23 and 24, deck 1200 further includes system controller 1210, cylinder assembly 1211, manifold assemblies 1213, pump cable 1215, pump motor cable 1216, and timing belt assembly 1217. System controller 1210 is a properly programmed integrated circuit that is operably coupled to the necessary components of the system to perform all of the functions, interactions, decisions, and reaction discussed above and necessary to perform a photopheresis therapy according to the present invention. Cylinder assembly 1211 couples each of compression actuators 1240-1247 to a pneumatic cylinder. Air ports 1212 are provided on the various elements of deck 1200 as necessary to connect air lines to the devices and the appropriate one of manifolds 1213. As such, air can be provided to the devices as necessary to actuate the necessary component, such as compression valves 1240-1247. All of these functions and timing are controlled by system controller 1210. Timing belt assembly 1217 is used to coordinate the rotation of rotating clamps 1203. Finally, plate 1202 includes a plurality of holes 1215, 1219, 1220, 1221, and 1218 so that the various components of deck 1200 can be properly loaded into and so that deck 1200 can be secured to tower system 2000. Specifically, pumps 1301-1305 fit into holes 1314, HCT sensor assembly 1205 fits into hole 1220, air bubble detector assembly 1204 fits into hole 1219, compression actuators 1240-1247 extend through holes 1218, and bolts extend through holes 1221 to secure deck 1200 to tower assembly 2000.

Cassette Clamping Mechanism

Referring now to FIGS. 22 and 25, the method by which cassette 1100 is loaded and secured to deck 1200 will now be discussed. In order for system 2000 to perform a photopheresis therapy, cassette 1100 must be properly loaded onto deck 1200. Because of the compression actuator valving system incorporated in the present invention, it is imperative that cassette 1100 be properly secured to deck 1200 and not shift or become dislodged when compression actuators 1240-1247 occlude portions of the flexible tubing by compressing the flexible tubing against cover 1130 of cassette 1100 (FIG. 3). However, this requirement competes with the desired goals of ease in loading cassette 1100 onto deck 1200 and reducing operator errors. All of these goals are achieved by the below described cassette clamping mechanism.

In order to facilitate clamping of cassette 1100 to deck 1200, deck 1200 is provided with two catches 1208 and two rotating clamps 1203 and 1223. Catches 1208 have a slot 1228 near the middle of the top plate. Catches 1208 are secured to plate 1202 at predetermined positions so that the spacing between them is substantially the same as the spacing between tabs 1102 and 1103 on cassette 1100 (FIG. 2). Rotating clamps 1203 and 1223 are illustrated in a closed position. However, rotating clamps 1203 and 1223 can be rotated to an open position (not illustrated) manually or through the automatic actuation of a pneumatic cylinder. Rotating clamps 1203 and 1223 are spring loaded by torque springs so as to automatically return to the closed position when additional torque is not being applied. Rotating clamps 1203 and 1223 are linked together by timing belt assembly 1217 (FIG. 24).

Referring now to FIG. 23, timing belt assembly 1217 comprises timing belt 1226, torque spring housings 1224, and tension assembly 1225. Timing belt assembly 1217 coordinates the rotation of rotational clamps 1203 and 1223 so that if one is rotated, the other also rotates in the same direction and the same amount. In other words, rotational clamps 1203 and 1223 are coupled. Tension assembly 1217 ensures that timing belt 1226 is under sufficient tension to engage and rotate the rotational clamp 1203 or 1223 that is being coordinated. Torque spring housings 1224 provide casings for the torque springs that torque rotational clamps 1203 and 1223 to the closed position.

Referring back to FIGS. 22 and 25, when loading cassette 1100 onto deck 1200, cassette 1100 is placed at an angle to deck 1200 and tabs 1102 and 1103 (FIG. 2) are aligned with catches 1208. Cassette 1100 is moved so that tabs 1102 and 1103 slidably insert into catches 1208. Rotational clamps 1203 and 1223 are in the closed position at this time. The rear of the cassette 1100 (i.e. the side opposite the tabs 1102 and 1103) contacts rotational clamps 1203 and 1223 as tabs 1102 and 1103 are being inserted in catches 1108. As force is applied downward on cassette 1100, rotational clamps 1103 and 1123 will be rotated to the open position, allowing the rear of cassette 1100 to move downward to a position below ledges 1231 of rotational clamps 1203 and 1223. Once cassette 1100 is in this position, the rotational clamps 1203 and 1223 spring back from the force applied by the torque springs and rotate back to the closed position, locking cassette 1100 in place. When in the locked position, cassette 1100 can resist upward and lateral forces.

To remove cassette 1110 after the therapy session is complete, rotational clamps 1203 and 1223 are rotated to the open position either manually or automatically. Automatic rotation is facilitated by an air cylinder that is coupled to an air line and system controller 1210. Once rotational clamps 1203 and 1223 are in the open position, cassette 1100 is removed by simple lifting and sliding tabs 1102 and 1103 out of catches 1208.

Self-Loading Peristaltic Pumps

Referring to FIG. 24, peristaltic pumps 1301-1305 are provided on deck 1200 and are used to drive fluids through photopheresis kit 1000 (FIG. 1) along desired pathways. The activation, deactivation, timing, speed, coordination, and all other functions of peristaltic pumps 1301-1305 are controlled by system controller 1210. Peristaltic pumps 1301-1305 are identical in structure. However, the placement of each peristaltic pump 1301-1305 on deck 1200 dictates the function of each peristaltic pump 1301-1305 with respect to which fluid is being driven and along which pathway. This is because the placement of peristaltic pumps 1301-1305 dictates which pump loop 1220-1224 will be loaded therein.

Figure 28:
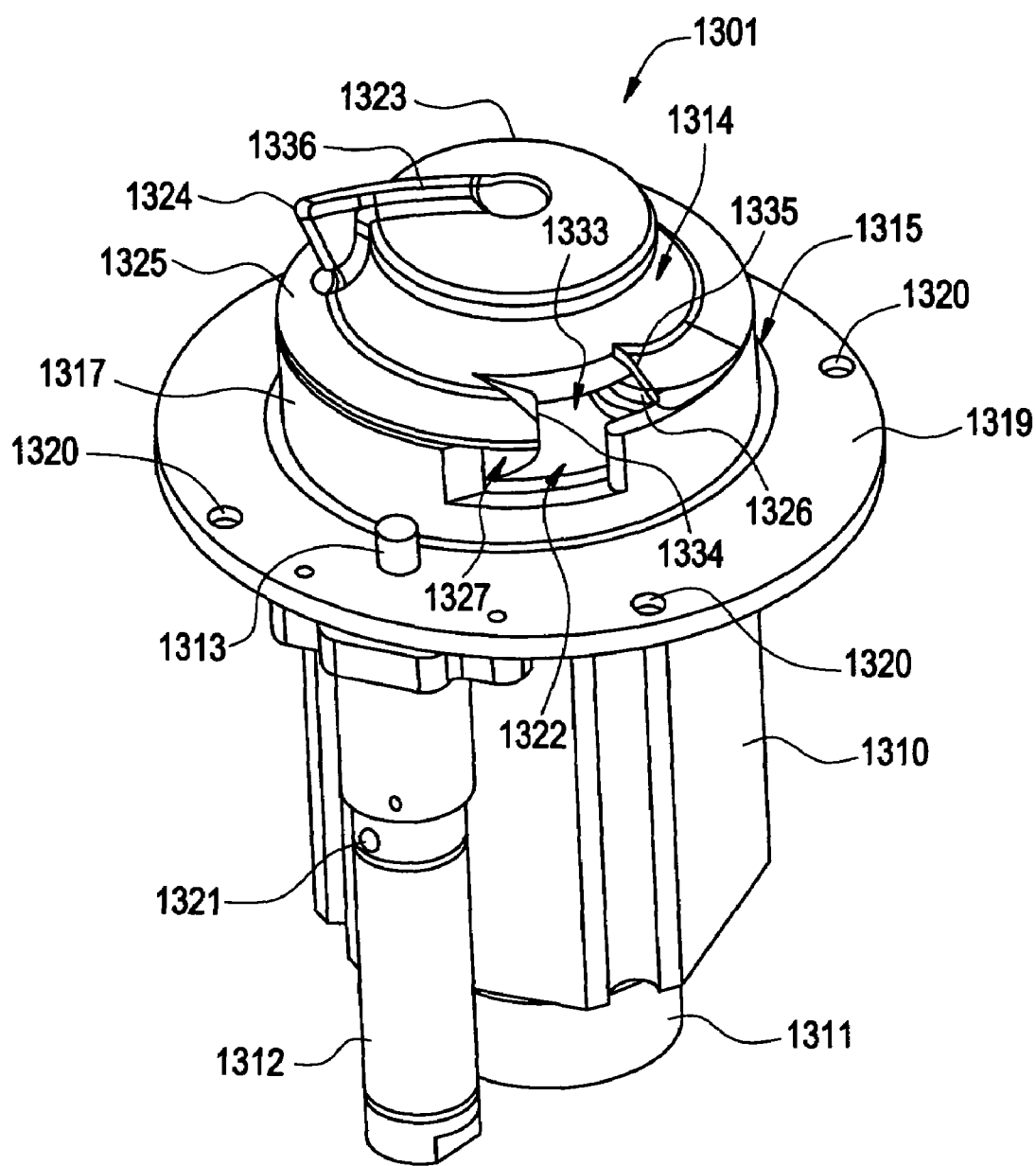
FIG. 28 is top perspective view an embodiment of a peristaltic pump.
Figure 29:
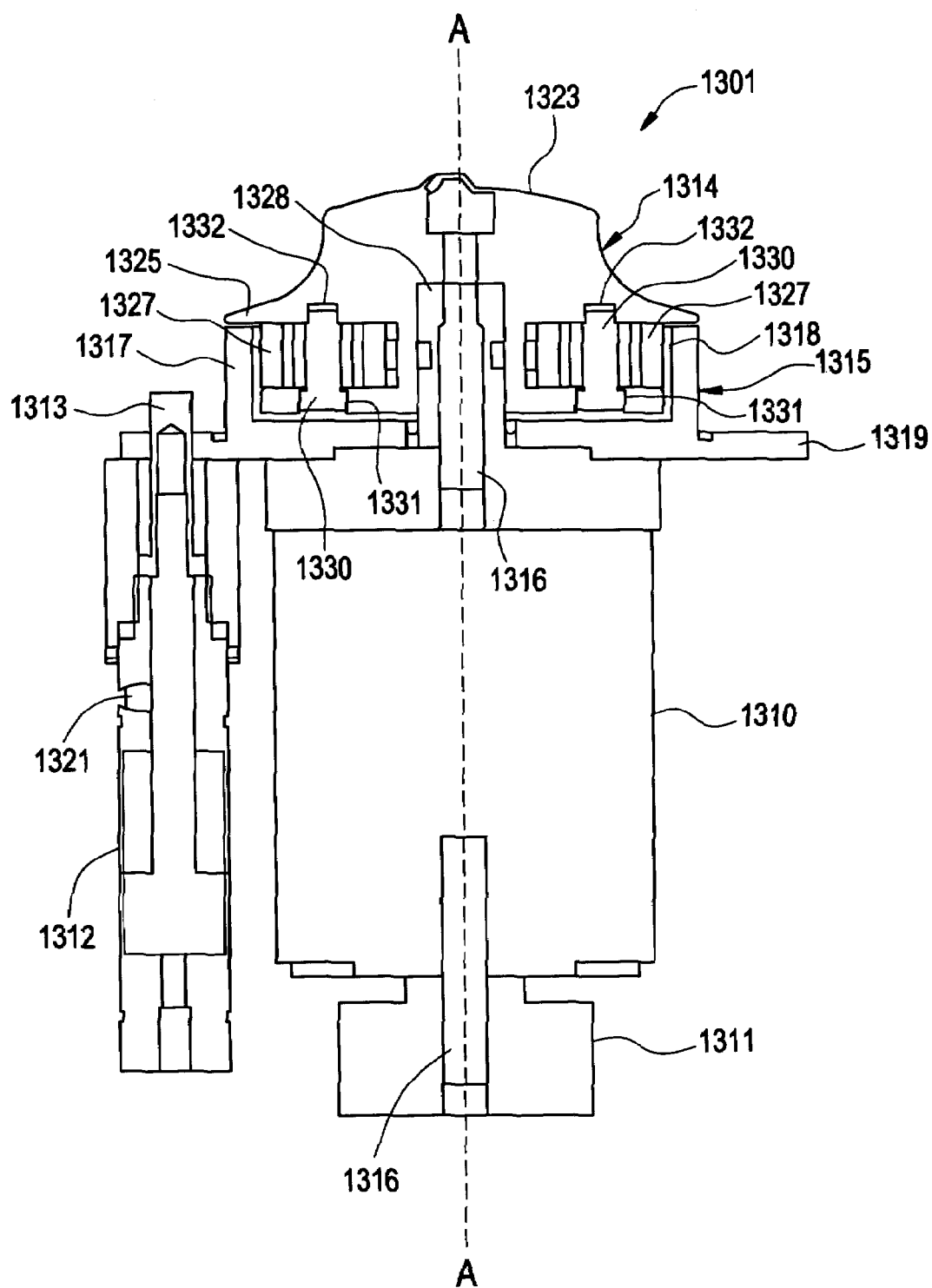
FIG. 29 is a cross sectional side view of the peristaltic pump of FIG. 28.

Referring now to FIGS. 28 and 29, whole blood pump 1301 is illustrated in detail. The structure and functioning of whole blood pump will be described with the understanding that peristaltic pumps 1302-1305 are identical. Whole blood pump 1301 has motor 1310, position sensor 1311, pneumatic cylinder 1312, pneumatic actuator 1313, rotor 1314 (best illustrated in FIG. 30), and housing 1315.

Rotor 1314 is rotatably mounted within housing 1315 and is in operable connection with drive shaft 1316 of motor 1310. Specifically, rotor 1314 is mounted within curved wall 1317 of housing 1315 so as to be rotatable by motor 1310 about axis A-A. When rotor 1314 is mounted in housing 1315, a space 1318 exists between rotor 1314 and curved wall 1317. This space 1318 is the tube pumping region of whole blood pump 1301 into which pump loop tube 1121 (FIG. 33) fits when loaded for pumping. Position sensor 1316 is coupled to drive shaft 1316 of motor 1310 so that the rotational position of rotor 1314 can be monitored by monitoring drive shaft 1316. Position sensor 1311 is operably connected and transmits data to system controller 1210 (FIG. 24). By analyzing this data, system controller 1210, which is also coupled to motor 1310, can activate motor 1310 to place rotor 1314 in any desired rotational position.

Housing 1315 also includes a housing flange 1319. Housing flange 1319 is used to secure whole blood pump 1310 to plate 1202 of deck 1200 (FIG. 22). More specifically, a bolt is extended through bolt holes 1320 of housing flange 1319 to threadily engage holes within plate 1202. Housing flange 1319 also includes a hole (not shown) to allow pneumatic actuator 1313 to extend therethrough. This hole is sized so that pneumatic actuator 1313 can move between a raised and lowered position without considerable resistance. Pneumatic actuator 1313 is activated and deactivated by pneumatic cylinder 1312 in a piston-like manner through the use of air. Pneumatic cylinder 1312 comprises air inlet hole 1321 for connecting an air supply line. When air is supplied to pneumatic cylinder 1312, pneumatic actuator extends upward through housing flange 1319 to a raised position. When air ceases to be supplied to pneumatic cylinder 1312, pneumatic actuator retracts back into pneumatic cylinder 1312, returning to the lowered position. System controller 1210 (FIG. 22) controls the supply of air to air inlet hole 1321.

Curved wall 1317 of housing 1315 contains two slots 1322 (only one visible). Slots 1322 are located on substantially opposing sides of curved wall 1317. Slots 1322 are provided for allowing pump loop tube 1121 (FIG. 33) to pass into tube pumping region 1318. More specifically, pump inlet portion 1150 and outlet portions 1151 (FIG. 33) of pump loop tube 1121 pass through slots 1322.

Figure 30:
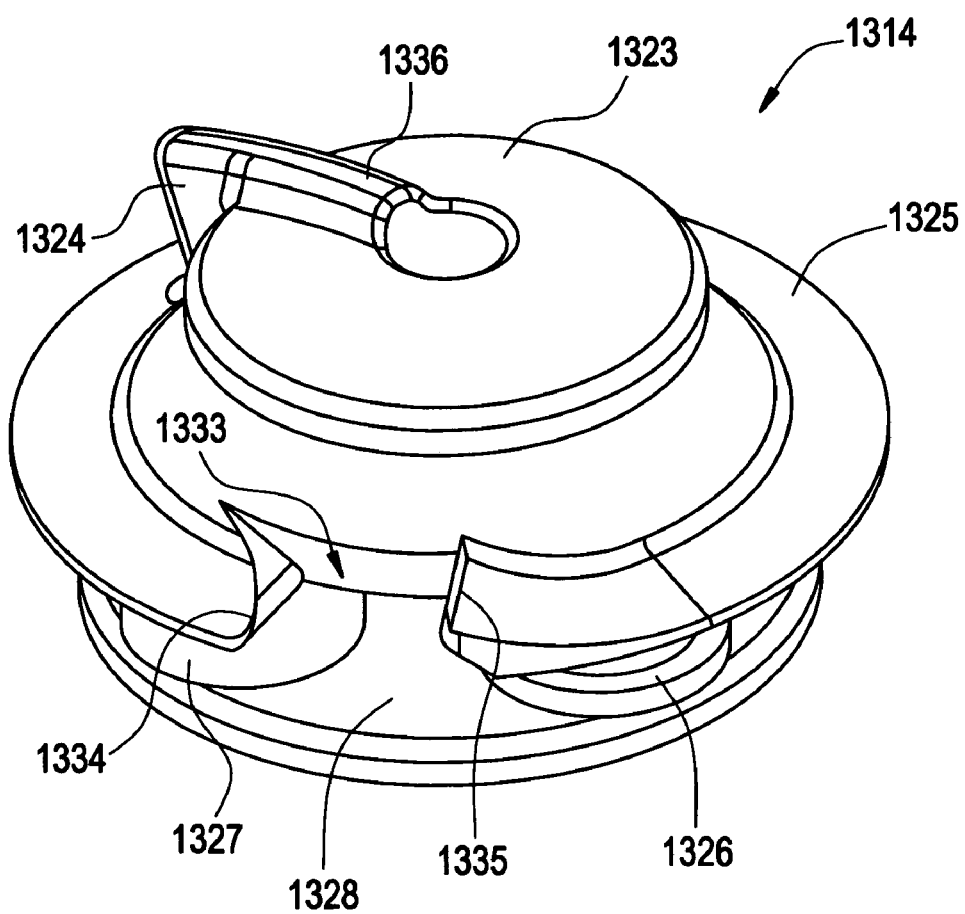
FIG. 30 is a top perspective view the rotor of the peristaltic pump of FIG. 29.
Figure 31:
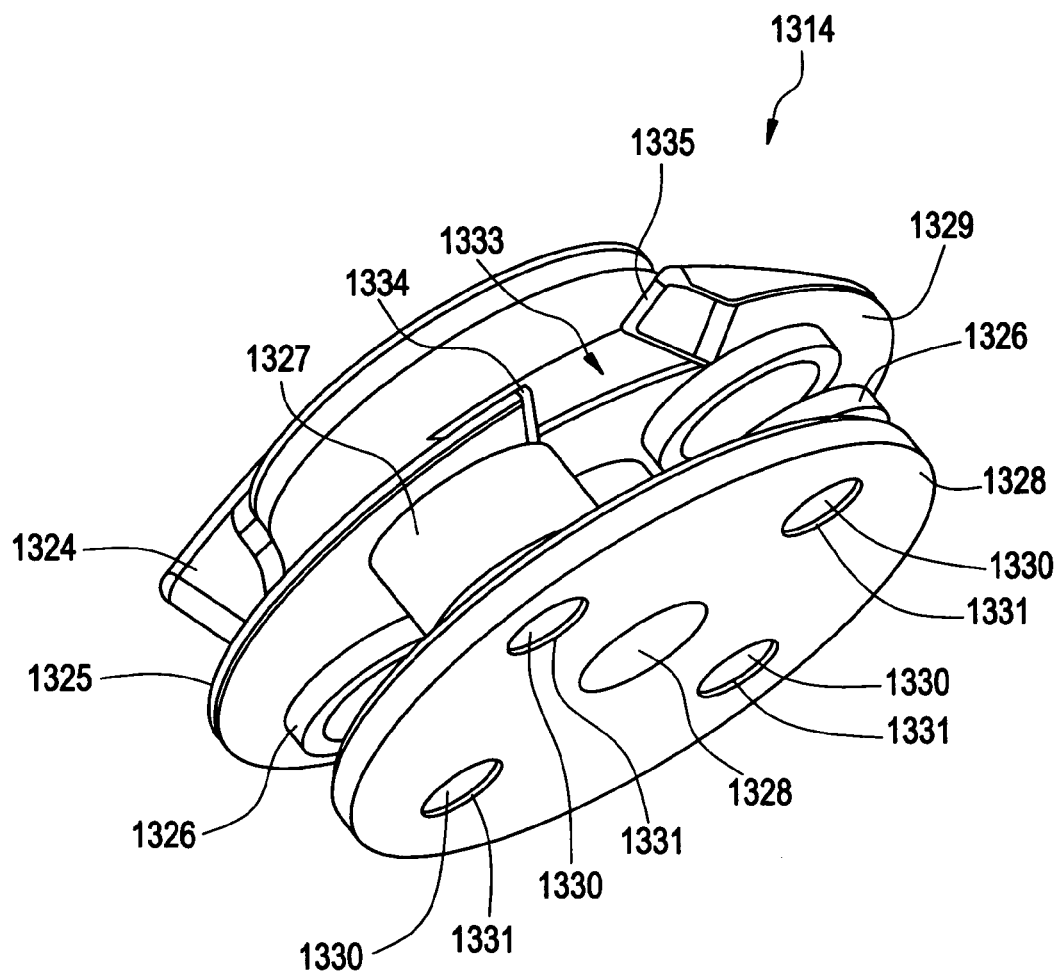
FIG. 31 is a bottom perspective view of the rotor of FIG. 30.

Turning now to FIGS. 30 and 31, rotor 1314 is illustrated as removed from housing 1315 so that its components are more clearly visible. Rotor 1314 has a top surface 1323, angled guide 1324, rotor flange 1325, two guide rollers 1326, two drive rollers 1327, and rotor floor 1328. Guide rollers 1326 and drive rollers 1327 are rotatably secured about cores 1330 between rotor floor 1328 and a bottom surface 1329 of rotor flange 1325. As is best illustrated in FIG. 29, cores 1330 fit into holes 1331 of rotor floor 1328 and recesses 1332 in bottom surface 1329. Guide rollers 1326 and drive rollers 1327 fit around cores 1330 and can rotate thereabout. Preferably, two guide rollers 1326 and two drive rollers 1327 are provided. More preferably, guide rollers 1326 and drive rollers 1327 are provided on rotor 1314 so as to be in an alternating pattern.

Referring to FIGS. 29 and 31, drive rollers 1327 are provided to compress the portion of pump loop tube 1121 that is loaded into tube pumping region 1318 against the inside of curved wall 1317 as rotor 1314 rotates about axis A-A, thereby deforming the tube and forcing fluids to flow through the tube. Changing the rotational speed of rotor 1314 will correspondingly change the rate of fluid flow through the tube. Guide rollers 1326 are provided to keep the portion of pump loop tube 1121 that is loaded into tube pumping region 1318 properly aligned during pumping. Additionally, guide rollers 1326 help to properly load pump tube loop 1121 into tube pumping region 1318. While guide rollers 1326 are illustrated as having a uniform cross-section, it is preferred that the top plate of the guide rollers be tapered so as to come to a sharper edge near its outer diameter. Tapering the top plate results in a guide roller with a non-symmetric cross-sectional profile. The tapered embodiment helps ensure proper loading of the tubing into the tube pumping region.

Rotor 1314 further includes cavity 1328 extending through its center. Cavity 1328 is designed to connect rotor 1314 to drive shaft 1316 of motor 1310.

Figure 32:
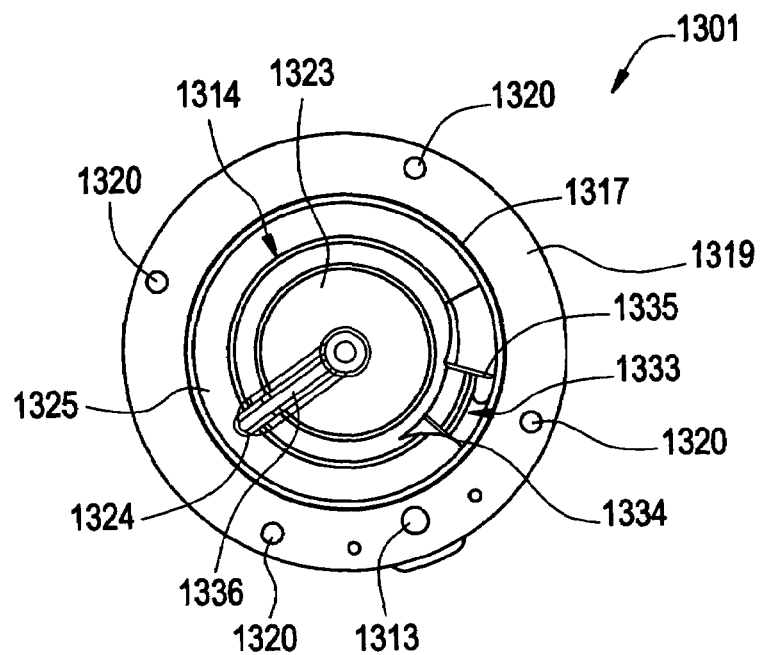
FIG. 32 is a top view of the peristaltic pump of FIG. 28.

Referring now to FIGS. 30 and 32, rotor flange has opening 1333. Opening 1333 is defined by a leading edge 1334 and a trailing edge 1335. The terms leading and trailing are used assuming that rotating rotor 1314 in the clockwise direction is the forward direction while rotating rotor 1314 in a counter-clockwise direction is the rearward direction. However, the invention is not so limited and can be modified for counter-clockwise pumps. Leading edge 1334 is beveled downward into opening 1333. Trailing edge 1335 extends upward from the top surface of rotor flange 1325 higher than the leading edge 1334. Leading edge is provide for trailing edge for capturing and feeding pump loop tube 1121 into tube pumping region 1318 upon rotor 1314 being rotated in the forward direction.

Rotor 1314 also has angled guide 1324 extending upward, at an inverted angle, from rotor flange 1325. Angled guide 1324 is provided for displacing pump loop tube 1121 toward rotor flange 1325 upon rotor 1314 being rotated in the forward direction. Preferably, angled guide 1324 has elevated ridge 1336 running along top surface 1323 for manual engagement by an operator if necessary. More preferably, angled guide 1314 is located forward of leading edge 1334.

Figure 33:
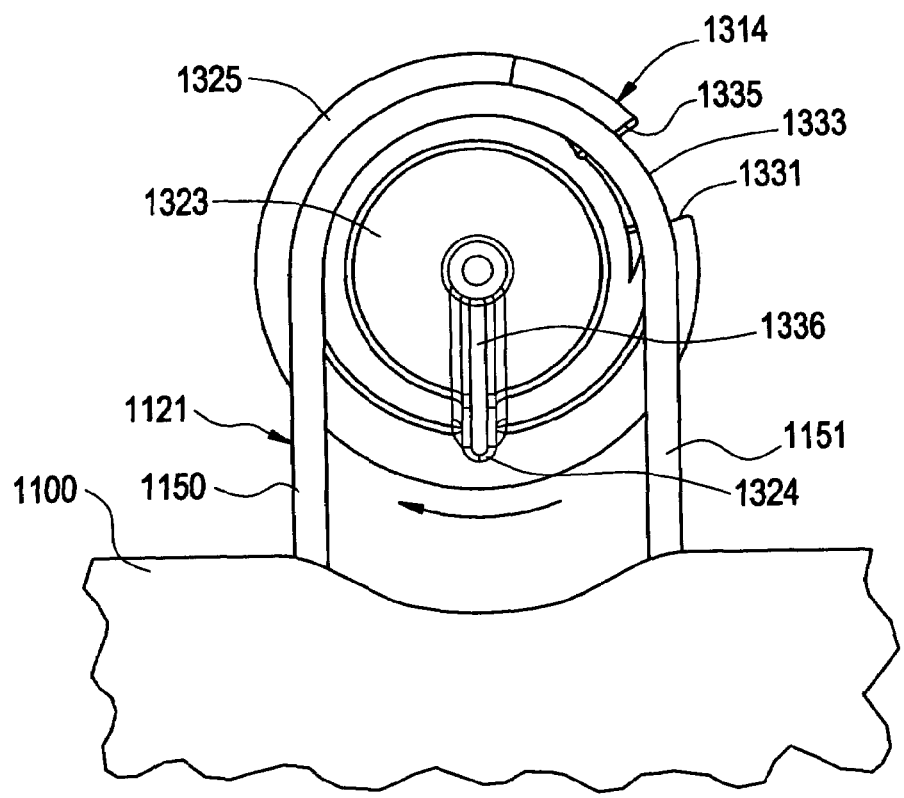
FIG. 33 is a top view of the peristaltic pump of FIG. 28 in a loading position and near the cassette of FIG. 2.

Referring now to FIGS. 28 and 33, whole blood pump 1301 can automatically load and unload pump lop tube 1121 into and out of tube pumping region 1318. Using position sensor 1311, rotor 1314 is rotated to a loading position where angled guide 1324 will face cassette 1100 when cassette 1100 is loaded onto deck 1200 (FIG. 25). More specifically, rotor 1314 is preset in a position so that angled guide 1324 is located between inlet portion 1150 and outlet portion 1151 of pump loop 1121 when cassette 1100 is secured to the deck, as is illustrated in FIG. 13. When cassette 1100 is secured to deck 1200, pump lop tube 1121 extends over and around rotor 1314. Pneumatic actuator 1313 is in the lowered position at this time.

Once cassette 1100 is properly secured and the system is ready, rotor 1314 is rotated in the clockwise direction (i.e., the forward direction). As rotor 1314 rotates, pump tube loop 1121 is contacted by angled guide 1324 and displaces against the top surface of rotor flange 1325. The portions of pump loop tube 1121 that are displaced against rotor flange 1325 are then contacted by trailing edge 1325 and fed downward into tube pumping region 1318 through opening 1333. A guide roller 1326 is provided directly after opening 1333 to further properly position the tubing within tube pumping chamber for pumping by drive rollers 1327. When loaded, inlet portion 1150 and outlet portion 1151 of pump loop tube 1121 pass through slots 1322 of curved wall 1317. One and a half revolutions are needed to fully load the tubing.

To automatically unload pump tube loop 1121 from whole blood pump 1301 after the therapy is complete, rotor 1314 is rotated to a position where opening 1333 is aligned with the slot 1322 through which outlet portion 1151 passes. Once aligned, pneumatic actuator 1313 is activated and extended to the raised position, contacting and lifting outlet portion 1151 to a height above trailing edge 1335. Rotor 1314 is then rotated in the counterclockwise direction, causing trailing edge to 1335 to contact and remove pump loop tube 1121 from tube pumping region 1318 via opening 1333.

Infra-Red Communication

Figure 34A:
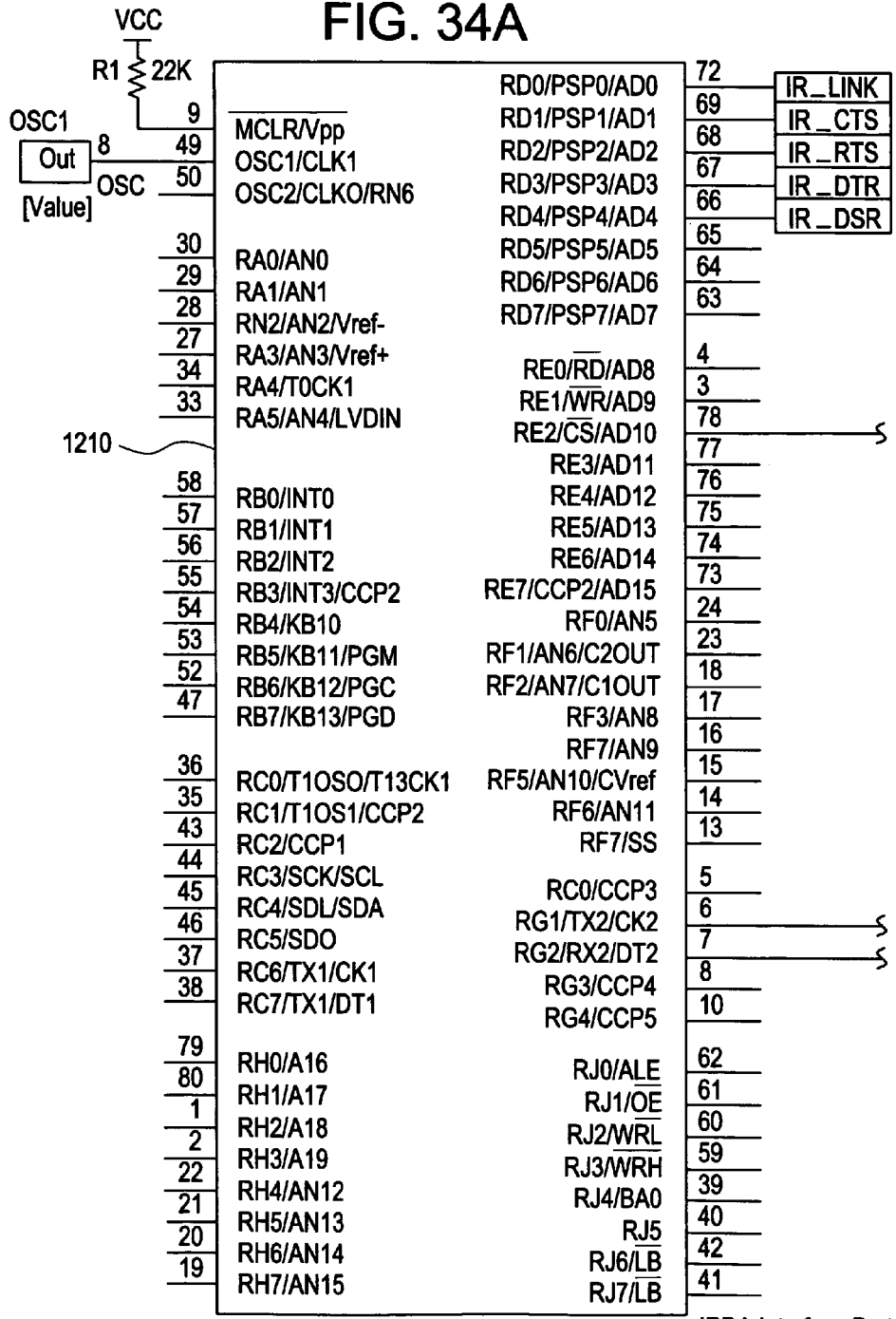
FIG. 34 is an electrical schematic of the infrared communication port circuit.
Figure 34B:
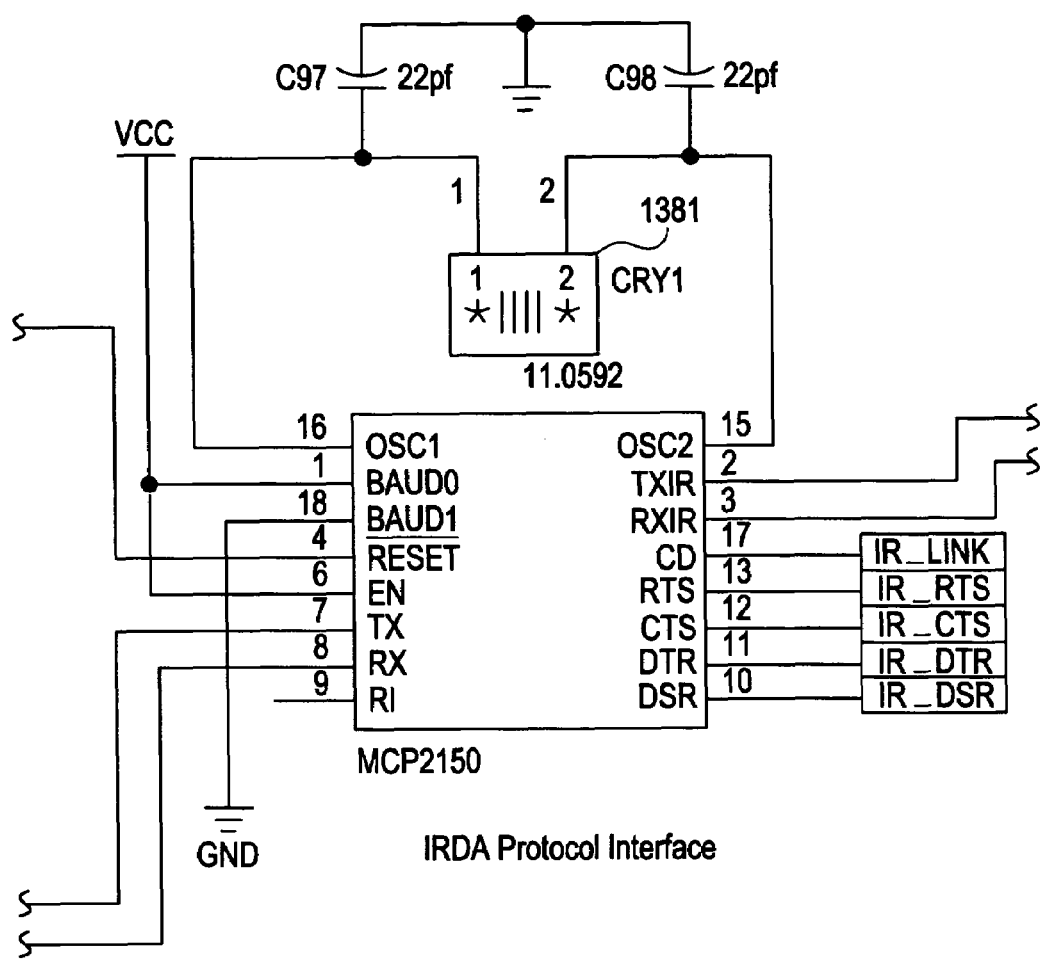
Figure 34C:
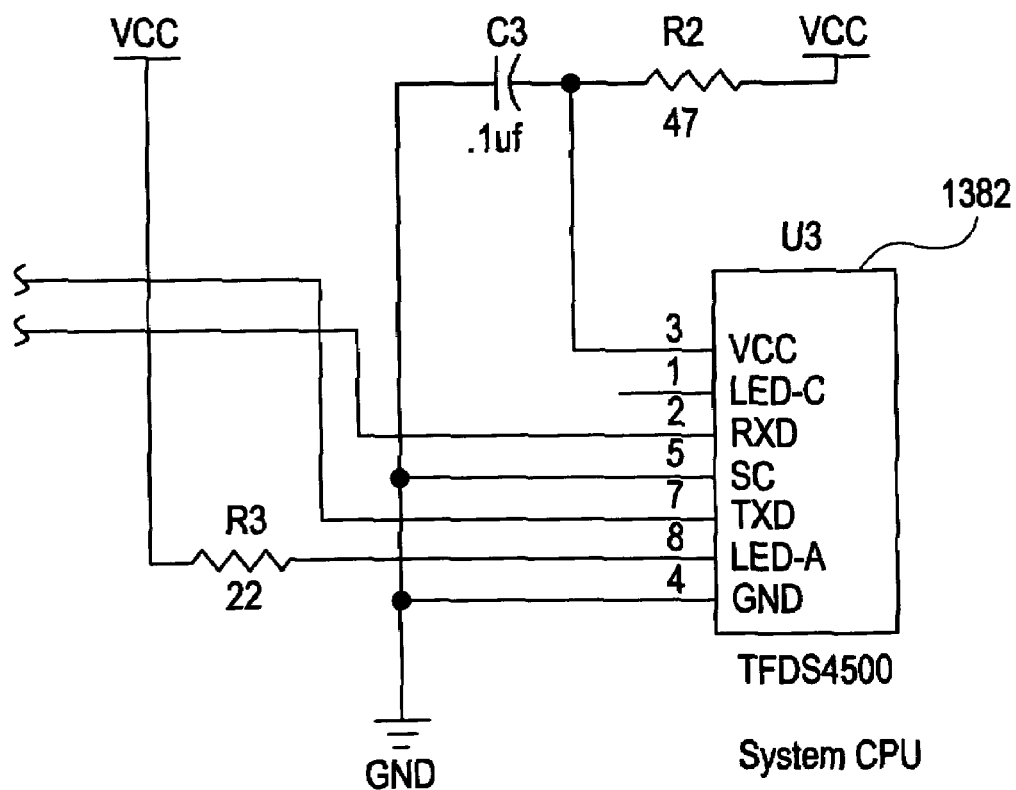

Referring to FIG. 34, tower system 2000 (FIG. 17) preferably further includes a wireless infrared ("IR") communication interface (not shown). The wireless IR interface consists of three primary elements, system controller 1210, IRDA protocol integrated circuit, 1381, and IRDA transceiver port 1382. The IR communication interface is capable of both transmitting and receiving data via IR signals from a remote computer or other device having IR capabilities. In sending data, system controller 1210 sends serial communication data to the IRDA protocol chip 1381 to buff the data. IRDA protocol chip 1381 adds additional data and other communication information to the transmit string and then sends it to IRDA transceiver 1382. Transceiver 1382 converts the electrical transmit data into encoded light pulses and transmits them to a remote device via a photo transmitter.

In receiving data, IR data pulses are received by a photo detector located on the transceiver chip 1382. The transceiver chip 1382 converts the optical light pulses to electrical data and sends the data stream to IRDA protocol chip 1381 where the electrical signal is stripped of control and additional IRDA protocol content. The remaining data is then sent to the system controller 1210 where the data stream is parsed per the communication protocol.

By incorporating an IR communication interface on tower system 2000 real time data relating to a therapy session can be transmitted to a remote device for recording, analysis, or further transmission. Data can be sent via IR signals to tower system 2000 to control the therapy or allow protocols to be changed in a blinded state. Additionally, IR signals do not interfere with other hospital equipment, like other wireless transmission methods, such as radio frequency.

Photopheresis Treatment Process

Figure 26A:
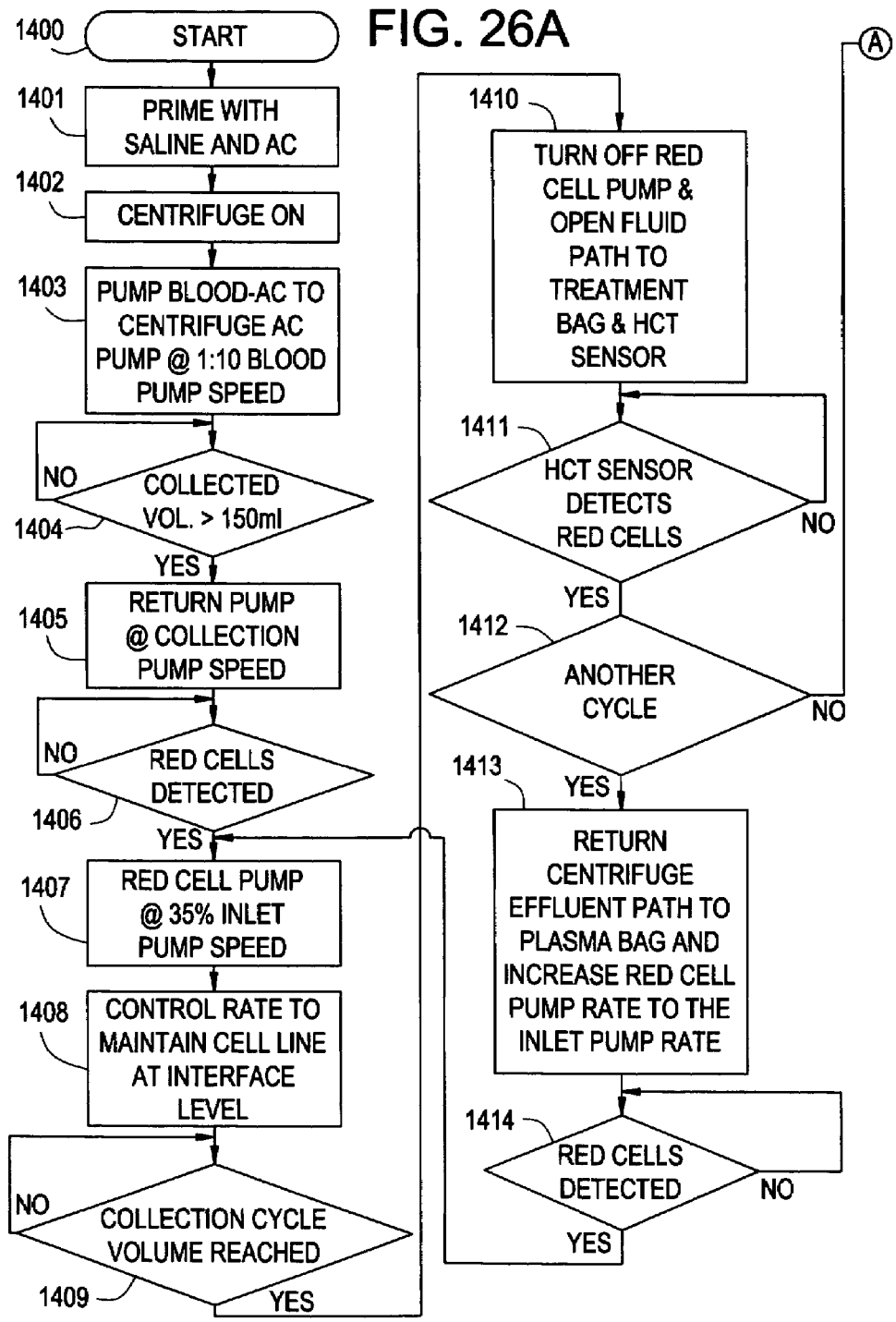
FIG. 26 is a flowchart of an embodiment of a photopheresis treatment process.
Figure 26B:
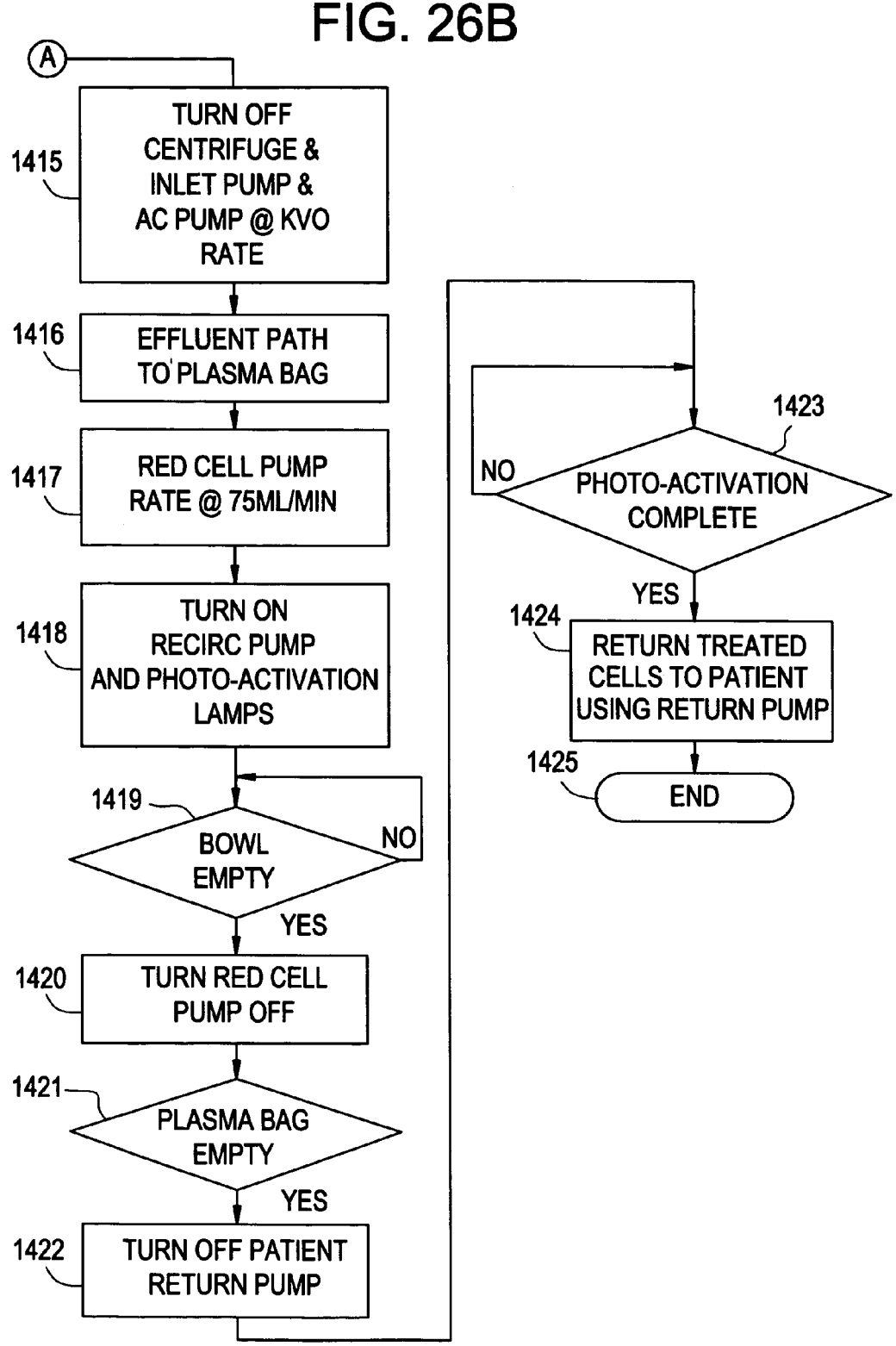

Referring together to FIG. 26, a flow chart illustrating an embodiment of the invention which includes photactivation of buffy coat, and FIG. 27, a schematic representation of apparatus which can be employed in such an embodiment, the process starts 1400 with a patient 600 connected by means of a needle adapter 1193 carrying a needle, for drawing blood, and needle adapter 1194 carrying another needle, for returning treated blood and other fragments. Saline bag 55 is connected by connector 1190 and anticoagulant bag 54 is connected by connector 1191. Actuators 1240, 1241, and 1242 are opened, anticoagulant pump 1304 is turned on, and saline actuator 1246 is opened so that the entire disposable tubing set is primed 1401 with saline 55 and anticoagulant 54. The centrifuge 10 is turned on 1402, and blood-anticoagulant mixture is pumped 1403 to the centrifuge bowl 10, with the A/C pump 1304 and WB pump 1301 controlled at a 1:10 speed ratio.

When the collected volume reaches 150 ml 1404, the return pump 1302 is set 1405 at the collection pump 1301 speed until red cells are detected 1406 at an HCT sensor (not shown) in the centrifuge chamber 1201 (FIG. 19). Packed red cells and buffy coat have at this point accumulated in the spinning centrifuge bowl and are pumped out slowly at a rate, controlled by the processor, which maintains the red cell line at the sensor interface level.

The red cell pump 1305 is then set 1407 at 35% of the inlet pump speed while controlling 1408 the rate to maintain the cell line at the interface level until the collection cycle volume is reached 1409, at which point the red cell pump 1305 is turned off 1410 and the fluid path to the treatment bag 50 via the HCT sensor 1125 is opened by lowering actuator 1244, and stops when the HCT sensor 1125 detects 1411 red cells. "Collection cycle volume" is defined as the whole blood processed target divided by the number of collection cycles, for example a white blood process target of 1500 ml may require 6 cycles, and so 1500/6 is a volume of 250 ml. With whole blood continuing at 1410 to be delivered from the patient to the bowl and the red cell pump off, red cells will accumulate and will push out the buffy coat from inside the bowl 10. The red cells are used to push out the buffy coat and will be detected by the effluent hematocrit (HCT) sensor, indicating that the buffy coat has been collected.

If another cycle is needed 1412, the centrifuge 10 effluent path is returned 1413 to the plasma bag 51 and the red cell pump 1305 rate is increased 1413 to the inlet pump 1301 pump rate until red cells are detected 1414, which is the beginning of the second cycle. If another cycle 1412 is not needed, the centrifuge 10 is turned off 1415 and inlet pump 1301 and anticoagulant pump 1304 are set at KVO rate, 10 ml/hr in this embodiment. The effluent path is directed 1416 to the plasma bag 51, the red cell pump 1305 rate is set 1417 at 75 ml/min, the recirculation pump 1303 and photoactivation lamps are turned on 1418 for sufficient period to treat the buffy coat, calculated by the controller depending on the volume and type of disease being treated.

When the bowl 10 is empty 1419, the red cell pump 1305 is turned off 1420 and the plasma bag 51 is emptied 1421 by opening actuator 1247 and continuing return pump 1302. The return pump 1302 is turned off 1422 when the plasma bag 51 is empty and when photoactivation is complete 1423, the treated cells are returned 1424 to the patient from the plate 700 by means of the return pump 1302. Saline is used to rinse the system and the rinse is returned to the patient, completing the process 1425.

The anticoagulant, blood from patient, and fluid back to patient are all monitored by air detectors 1204 and 1202, and the fluid back to the patient goes through drip chamber and filter 1500. The pumps, 1304, 1301, 1302, 1303, and 1305, the actuators 1240, 1241, 1242, 1243, 1244, 1245, 1246, and 1247, and the spinning of the bowl 10 are all controlled by the programmed processor in the tower.

The process and related apparatus have significant advantages over prior processes and apparatus in that the invention allow buffy coat to be in the bowl longer since red cells are being drawn off while collecting buffy coat in the bowl while centrifuging, keeping more buffy coat in the bowl until the desired amount of buffy coat cells are collected prior to withdrawing the collected buffy cells. Platelets, leukocytes, and other buffy coat fractions can also be separated, or red cells can be collected rather than returning them with plasma to the patient as the illustrated process does.

It has been found that increasing the time that buffy coat 810 is subjected to rotational motion in centrifuge bowl 10 yields a "cleaner cut" of buffy coat 820. A "cleaner cut" means that the hematocrit count (HCT %) is decreased. HCT % is the amount of red blood cells present per volume of buffy coat. The amount of time that buffy coat 820 is subjected to rotational motion in centrifuge bowl 10 can be maximized in the following manner. First, whole blood 800 is fed into first bowl channel 420 as centrifuge bowl 10 is rotating. As discussed above, whole blood 800 is separated into buffy coat 820 and RBC's 810 as it moves outwardly atop lower plate 300. Second bowl channel 410 and third bowl channel 740 are closed at this time. The inflow of whole blood 800 is continued until the separation volume 220 is filled with a combination of buffy coat 820 near the top and RBC's 810 near the bottom of centrifuge bowl 10. By removing RBC's 810 from centrifuge bowl 10 via second bowl channel 410 only, additional volume is created for the inflow of whole blood 800 and the unremoved buffy coat 820 is subjected to rotational forces for an extended period of time. As centrifuge bowl 10 continues to rotate, some of the RBC's 810 that may be trapped in buffy coat 820 get pulled to the bottom of centrifuge bowl 10 and away from third bowl channel 740 and buffy coat 820. Thus, when third bowl channel 740 is opened, the buffy coat 820 that is removed has a lower HCT %. By controlling the inflow rate of whole blood 800 and the outflow rates of buffy coat 820 and RBC's 810, a steady state can be reached that yields a buffy coat 820 with an approximately constant HCT %.

The elimination of batch processing and the improved yields achieved by the current invention, have reduced the treatment time necessary to properly treat patients. For an average sized adult, 90-100 milliliters of buffy coat/white blood cells must be captured in order to conduct a full photopheresis treatment. In order to collect this amount of buffy coat/white blood cells, the present invention needs to process around 1.5 liters of whole blood. The required amount of buffy coat/white blood cells can be removed from the 1.5 liters of whole blood in about 30-45 minutes using the present invention, collecting around 60% or more of the total amount of the buffy coat/white blood cells that are subjected to the separation process. The captured buffy coat/white blood cells have an HCT of 2% or less. In comparison, one existing apparatus, the UVAR XTS, takes around 90 minutes to process 1.5 liters of whole blood to obtain the sufficient amount of buffy coat/white blood cells. The UVAR XTS only collects around 50% of the total amount of the buffy coat/white blood cells that are subjected to the separation process. The HCT of the buffy coat/white blood cells collected by the UVAR XTS is around, but not substantially below, 2%. Another existing apparatus, the Cobe Spectra™ by Gambro, must process 10 liters of whole blood in order to collect the sufficient amount of buffy coat/white blood cells. This typically takes around 150 minutes, collecting only 10-15% of the total amount of the buffy coat/white blood cells that are subjected to the separation process, and having an HCT of about 2%. Thus, it has been discovered that while existing apparatus and systems require anywhere from 152 to 225 minutes to separate, process, treat, and reinfuse the requisite amount of white blood cells or buffy coat, the present invention can perform the same functions in less than 70 minutes. These times do not include the patient preparation or prime time. The times indicate only the total time that the patient is connected to the system.

Methods of Separating Buffy Coat into Components and Extracorporeal Photopheresis Treatment Process 2

The buffy coat component of blood itself has components with different densities. Cells having a higher density in a buffy coat layer may comprise myelocytes, reticulocytes, and cells having a lower density in a buffy coat comprise T-lymphocytes, B lymphocytes, promyeocytes and monocytes. As it may be desirable to perform the extracorporeal photopheresis treatment on a selected component of the buffy coat or to isolate a selected component of buffy coat for other therapeutic treatment, it is useful to be able to separate and collect only a desired component of the buffy coat layer. The desired component of the buffy coat may be separated and collected based on the differences in densities of buffy coat components. Centrifuge bowl 10 may be used to further separate the buffy coat component of blood into a higher density buffy coat layer and a lower density buffy coat layer.

A method for collecting a desired buffy coat layer comprises pumping whole blood into bowl 10 via an inlet to the first bowl channel 420A. Plasma is then separated and removed from the bowl by a first outlet, e.g. through bowl chamber 740A, and red blood cell is separated and removed via a second outlet or second bowl channel 410A through the inner lumen extends from housing floor 180A of bowl 10. When a desired volume of buffy coat is obtained, the red blood cell pump is stopped. As whole blood continues to be pumped to the bowl via the first bowl channel 420A to separation volume 220A through channel 305A, the accumulated red blood cells inside separation chamber 220A displace the buffy coat out of the bowl through the bowl chamber near the top of bowl housing. The buffy coat is then collected in the treatment bag. Subsequently, the collected buffy coat is returned it to bowl 10 for a second separation. Saline or other solution biocompatible with blood may have to be added to bowl 10 to attain the required volume for the centrifuge process. As the higher density component of buffy coat moves closer to outer housing wall 120A and to the bottom of bowl 10 where the g-force is greater than on top of the bowl and near the central axis, it is then collected via the second outlet bowl channel 410A through the inner lumen. When a desired volume or amount of higher density buffy coat layer has been collected, the pump removing the higher density buffy coat layer is stopped. Once the higher density component has been collected, the lower density component remained in bowl 10 may be removed from the bowl via the first outlet. Depending on the preferred treatment regimen, either the lower or higher density bufffy coat layer is selected for treatment with a photoactivatable compound and UVA radiation.

Bowl 10 may be operated in a different manner to enhance the separation of buffy coat. In this method of separating buffy coat, the second outlet bowl channel 410A may be used to remove not only the red blood cells but also the buffy coat component without first removing the buffy coat from bowl 10. The method comprises pumping whole blood into bowl 10 via an inlet to the first bowl channel 420A. Whole blood is then follows the first bowl channel 420A to separation volume 220A through channel 305A where it is separated into blood components. Plasma is first separated and removed from the bowl through a first outlet near the top of bowl 10, i.e. through bowl chamber 740A. Red blood cell is separated and removed via a second outlet or second bowl channel 410A through the inner lumen extends from housing floor 180A of bowl 10. A sensor may be used to determine when to stop pumping red blood cells from the bowl After the red blood cells are removed, the collected buffy coat can further be centrifuged to separate the collected buffy coat into a lower density buffy coat layer and a higher density buffy coat layer. The buffy coat is higher in density than plasma so it will now migrate towards the bottom of the bowl. Saline or other solutions compatible with blood may be added to have enough volume for the centrifuge separation process. The higher density buffy coat layer moves to closer to outer housing wall 120A and near the bottom where the g-forces are higher. The higher density buffy coat layer is then pumped out through the second bowl channel 410A.

What is claimed is:

1. An apparatus comprising a cassette for controlling movement of blood and separated blood components, the cassette comprising a housing formed by joining a rigid plastic cover and a rigid plastic base;

said rigid plastic cover having a top surface, a bottom surface, and a wall having a plurality of openings; said rigid plastic base having a top surface, a bottom surface, and a plurality of apertures through the top and bottom surfaces, and a wall having a plurality of openings adapted to overlap with the openings of the wall of the cover;

said top surface of the base comprises a first upper level and a first lower level, wherein the first lower level has a plurality of first flexible tubings, secured by raceways, for one or more of a) connecting to other tubings through multitube connectors, b) extending out of or entering the housing, or c) forming first flexible tube loops having one end extending out of the housing and one end entering the housing;

said plurality of apertures are located on the first lower level and expose at least one section of the first flexible tubing inside the housing so that fluid flow through the exposed section can be prevented when an actuator exerts pressure on the exposed section through the apertures against a first occluder bar located above the first lower level surface;

said bottom surface of the base comprises a second upper level and a second lower level, wherein the second lower level has a plurality of second flexible tubings outside of the housing and secured by raceways on said second lower level for one or more of extending through or entering the openings of the wall of the base or forming second flexible tube loops having one end extending out of the wall and one end entering the wall of the base; and wherein fluid flowing through the second flexible tubing can be prevented when another actuator exerts pressure on the tubing against a second occluder bar located on the second lower level of the bottom surface of the base.

2. The apparatus of claim 1 further comprises a filter in fluid communication with one first flexible tubing and one second flexible tubing, and a recordable smartcard on which are electronically recorded identification data.

3. The apparatus of claim 1 wherein the cassette has three first tube loops extend from inside the housing, two second tube loops extends from the lower level of the bottom surface of the base and five apertures on the base.

4. The apparatus of claim 1 wherein the apparatus further comprises a pressure dome that is connected in series between the cassette and a centrifuge bowl for measuring a pressure of a fluid inside a flexible tubing connecting the cassette to the centrifuge bowl, and a pressure dome which is configured to be connected in series between a blood donor or patient and the cassette for measuring a pressure of a blood or blood component in a flexible tubing configured to connect the patient to the cassette; and said flexible tubings having fluid communications with said pressure domes.

5. An apparatus according to claim 1 further comprises a centrifuge bowl for separating the components of a fluid, and flexible tubes fluidly connecting between the bowl and the cassette, the bowl comprising an outer housing having a housing outlet, said outer housing adapted for rotation about a center axis; said outer housing containing a core providing a separation volume between said core and said outer housing; said core has a core end and is connected with said outer housing for rotation therewith, said core end having a lumen connector;

a first lumen for providing fluid communication from the housing outlet through the lumen connector and then radially outward through the core to the fluid separation volume; a second lumen providing fluid communications from the housing outlet extending axially along center axis to housing floor;

a connection sleeve which forms with the lumen connector a chamber and provide fluid communications between the housing outlet and the separation volume; and the flexible tubes comprising a first flexible tube for inflowing of the fluid from the cassette to the first bowl channel; a second flexible tube for removing a the first separated fluid component of the second bowl channel; and a third flexible tube for removing a second separated fluid component from the bowl chamber to the cassette.

6. An apparatus according to claim 5 wherein the connection sleeve is adapted to be secured to the centrifuge bowl near said housing outlet of said outer housing for rotation therewith, said connection sleeve adapted to fluidly connect a first bowl channel, a second bowl channel, and a bowl chamber.

7. The apparatus of claim 6 wherein the first separated fluid component comprises red blood cells.

8. The apparatus of claim 6 wherein the second separated fluid component comprises buffy coat.

9. The apparatus of claim 1 further comprising an irradiation chamber having
- a first port connected to a flexible tube for carrying buffy coat from the cassette to the irradiation chamber;
- a second port connected to a flexible tube for carrying irradiated buffy coat from the irradiation chamber to the cassette;
- the irradiation chamber having a rigid first plate having a first surface and a second surface the second surface having a groove boundary formed by two ridges surrounding a plurality of groove partitions formed by two ridges;
- a rigid second plate having a first surface and a second surface, the second surface having a ridge boundary surrounding a plurality of ridge partitions;
- wherein the groove boundary and groove partitions of the second surface of the rigid first plate is contacted with the ridge boundary and ridge partitions of the second surface of the rigid second plate thereby forming a chamber;
- the chamber defined by a boundary formed by the joining of the groove boundary and the ridge boundary surrounding the plurality of partitions formed by the joining of the groove partitions and the ridge partition wherein a plurality of channels are formed by the partitions providing fluid communication with the first port and second port.

10. The apparatus of claim 1 wherein the first and second flexible tube loops of the cassette comprise an anticoagulant pump loop, a whole blood pump loop, a return to patient pump loop, a red blood pump loop, and a buffy coat recirculation pump loop.

11. The apparatus of claim 10 wherein the cassette comprises a recordable, removable smartcard having electronically stored unique identification information.

* * * * *